(12) United States Patent
Ahmad

(10) Patent No.: US 8,278,316 B2
(45) Date of Patent: Oct. 2, 2012

(54) AZA PYRIDONE ANALOGS USEFUL AS MELANIN CONCENTRATING HORMONE RECEPTOR-1 ANTAGONISTS

(75) Inventor: Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 22 days.

(21) Appl. No.: 13/255,170

(22) PCT Filed: Mar. 9, 2010

(86) PCT No.: PCT/US2010/026604
§ 371 (c)(1),
(2), (4) Date: Sep. 7, 2011

(87) PCT Pub. No.: WO2010/104818
PCT Pub. Date: Sep. 16, 2010

(65) Prior Publication Data
US 2011/0319439 A1    Dec. 29, 2011

Related U.S. Application Data

(60) Provisional application No. 61/158,531, filed on Mar. 9, 2009.

(51) Int. Cl.
*A01N 43/54* (2006.01)
*A61K 31/505* (2006.01)

(52) U.S. Cl. ............... 514/274; 514/252.02; 514/252.03; 544/309; 544/310; 544/316; 544/238; 544/224

(58) Field of Classification Search .............. 514/274, 514/252.02, 252.03; 544/309, 310, 316, 544/318, 238, 224
See application file for complete search history.

(56) References Cited

U.S. PATENT DOCUMENTS

| | | | |
|---|---|---|---|
| 2003/0069425 A1* | 4/2003 | Spohr et al. | 544/295 |
| 2007/0093509 A1 | 4/2007 | Washburn et al. | |
| 2007/0208046 A1 | 9/2007 | Otake et al. | |
| 2008/0085884 A1 | 4/2008 | Armour et al. | |
| 2009/0011994 A1 | 1/2009 | Stein et al. | |
| 2010/0087460 A1* | 4/2010 | Chereze et al. | 514/269 |
| 2011/0183981 A1* | 7/2011 | Marlow et al. | 514/237.2 |
| 2011/0251169 A1* | 10/2011 | Green et al. | 514/210.09 |
| 2011/0263582 A1* | 10/2011 | Claremon et al. | 514/228.8 |

FOREIGN PATENT DOCUMENTS

| | | |
|---|---|---|
| EP | 1 741 703 A1 | 1/2007 |
| WO | WO2005/042541 A1 | 5/2005 |
| WO | WO2007/141200 A1 | 12/2007 |
| WO | WO2007/142217 A1 | 12/2007 |

OTHER PUBLICATIONS

Borowsky, B. et al., "Antidepressant, anxiolytic and anorectic effects of a melanin-concentrating hormone-1 receptor antagonist", Nature Medicine, vol. 8(8), pp. 825-830 (2002).
Gehlert, D. et al., "Preclinical Evaluation of Melanin-Concentrating Hormone Receptor 1 Antagonism for the Treatment of Obesity and Depression", The J. of Pharmacology and Experimental Therapeutics, vol. 329(2), pp. 429-438 (2009).
Kokkotou, E. et al., "Melanin-concentrating hormone as a mediator of intestinal inflammation", PNAS, vol. 105(30), pp. 10613-10618 (2008).
Kowalski, T. et al., "Melanin-concentrating hormone-1 receptor antagonism decreases feeding by reducing meal size", European J. of Pharmacology, vol. 497, pp. 41-47 (2004).
Takekawa, S. et al., "T-226296: a novel, orally active and selective melanin-concentrating hormone receptor antagonist", European J. of Pharmacology, vol. 438, pp. 129-135 (2002).

* cited by examiner

*Primary Examiner* — James O Wilson
*Assistant Examiner* — Alexander R Pagano
(74) *Attorney, Agent, or Firm* — Maureen S. Gibbons; Jing G. Sun

(57) ABSTRACT

MCHR1 antagonists are provided having the following Formula I:

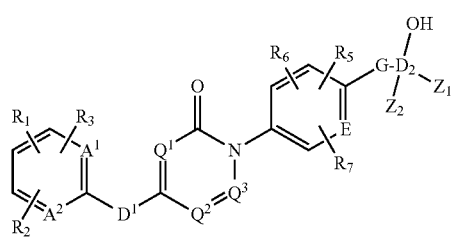

wherein all of the variables are defined herein. Such compounds are useful for the treatment of MCHR1 mediated diseases, such as obesity, diabetes, IBD, depression, and anxiety.

15 Claims, No Drawings

AZA PYRIDONE ANALOGS USEFUL AS MELANIN CONCENTRATING HORMONE RECEPTOR-1 ANTAGONISTS

CROSS-REFERENCE TO RELATED APPLICATIONS

The present application is a 371 application of PCT/US2010/026604 filed Mar. 9, 2010, which claims priority benefit of U.S. provisional application Ser. No. 61/158,531, filed Mar. 9, 2009, each of which is incorporated by reference herein.

FIELD OF THE INVENTION

The present invention relates to pyridone compounds which act as melanin concentrating hormone receptor-1 (MCHR1) antagonists, pharmaceutical compositions containing such compounds, and methods for using such compounds for the treatment of MCHR1 mediated diseases such as diabetes, obesity and inflammatory bowel disease.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol.*, 438:129-135 (2002), *Nat. Med.*, 8:825-830 (2002), *Eur. J. Pharmacol.*, 497:41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *PNAS*, 105(30):10613-10618 (Jul. 29, 2008).

In addition, MCH and MCHR1 has also been reported to play a role in the endocrine and behavioral responses to stress. Treatment of rats and mice with MCHR antagonists produce a robust anti-depressant and anti-anxiolytic effect. (JPET DOI:10.1124/jpet.108.143362)

Small molecule MCHR1 antagonists have been reported in the literature. See, for example, United States Patent Application Publication No. US 2009/0011994, which discloses compounds having the following Formula:

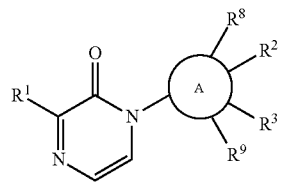

wherein

is a phenylene ring or a heteroaryl ring which is a monocyclic ring or a bicyclic ring which contains one or two nitrogen atoms or one oxygen atom;

$R^1$ is Z—Y—X—, wherein
X is O, S,

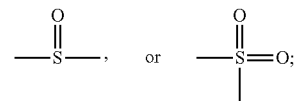

Y is a bond, a 3- to 6-membered cycloalkyl, or an alkyl chain; and

Z is aryl such as phenyl and naphthyl, or heteroaryl such as pyridinyl, pyridimidinyl, pyrazinyl, benzimidazolyl, benzothiazolyl, benzoxazolyl, or other "heteroaryl"; $R^2$ is -E-G-$(J)_m$, with m being an integer from 1 to 3;

E is O, S, or a bond; G is lower alkyl, phenylalkyl, cycloalkyl, cycloalkylalkyl, alkylcycloalkyl, cycloalkoxy, alkylcycloalkoxy, or cycloalkoxyalkyl;

each J is independently hydrogen, hydroxyl, CN, —$SO_2R^7$, —$SR^7$, —$SOR^7$, lower alkyl, lower alkoxy, $CF_3$, $CF_3O$—, —$COOR^5$ (wherein $R^5$ is H, $C_{1-3}$ alkyl, or cycloalkyl), or —CO—$NR^{5a}R^6$ wherein $R^{5a}$ and $R^6$ are each independently selected from H, $C_{1-3}$ alkyl, or cycloalkyl, or $R^{5a}$ and $R^6$ taken together can be propanediyl, butanediyl or pentanediyl to form with the N atom to which they are attached a 4-, 5- or 6-membered cyclic amine, such as azetidinyl, pyrrolidinyl, piperidinyl, morpholinyl, or piperazinyl, optionally substituted with substituents as set out for "heterocyclo";

$R^7$ is lower alkyl;
$R^3$ is $C_{1-6}$ alkyl, cycloalkyl, $C_{1-6}$ alkoxy, halogen, hydrogen, —S—$C_{1-6}$ alkyl, CN, $CF_3O$, or $CF_3$;

and wherein $R^2$ and $R^3$ can be taken together to form a 5- to 7-membered ring which is saturated, unsaturated, or partially unsaturated and may include an E heteroatom, which is O, or 0, 1 or 2 N atoms, which ring is substituted with one or two of —O-G-$(J)_m$ groups, wherein at least one J is OH, and optionally other substituents as set out for "alkyl", "aryl", or "heteroaryl", such as alkyl and/or OH;

with the proviso that where

is a phenylene ring, E-G and $R^3$ are not identical unsubstituted lower alkoxy groups, and when G is lower alkyl and J is H, $R^3$ is not hydrogen; and $R^8$ and $R^9$ are each independently hydrogen, halogen, or lower alkyl;

including esters thereof, prodrugs thereof, solvates thereof, and all stereoisomers thereof.

Specific examples include compounds having the following structures:

3-(benzylthio)-1-(4-(2-hydroxy-2-methylpropoxy)-3-methoxyphenyl)pyrazin-2(1H)-one 3-(4-fluorophenethylthio)-1-(4-(2-hydroxy-2-methylpropoxy)-3-methylphenyl)pyrazin-2(1H)-one United States Patent Application Publication No. US 2007/0093509 also discloses small molecule inhibitors of MCHR1 having the following Formula:

wherein,

A is selected from the group consisting of phenyl and a monocyclic heteroaryl;

D is selected from the group consisting of $CH_2$ and a direct bond;

$R^1$ is independently selected from the group consisting of hydrogen, halogen, lower alkyl, lower cycloalkyl, $CF_3$, $OR^6$ and $SR^6$;

$R^2$ is selected from the group consisting of hydrogen and lower alkyl;

$R^4$ is selected from the group consisting of hydroxyl or $G-D^2-Z_n$;

n is an integer from 1 to 3;

$R^5$ is selected from the group consisting of hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;

G is selected from the group consisting of O, S and $CR^7R^7$;

$D^2$ is selected from the group consisting of a direct bond, lower alkyl, lower cycloalkyl and a 4 to 6-membered non-basic heterocycle;

Z is selected from the group consisting of hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ and $COR^6$;

$R^6$ is independently selected from the group consisting of lower alkyl and lower cycloalkyl; and $R^7$ is independently selected from the group consisting of hydrogen, lower alkyl and lower cycloalkyl, wherein two $R^7$ and the atom to which they are attached may optionally form a ring of 4 to 7 atoms.

Other reported MCHR1 antagonists include those disclosed in the following published patent applications:

US 2008/0085884 (Pfizer), for example:

US 2007/0208046 (Banyu), for example:

and WO 2007142217 (Banyu), disclosing, for example:

There is a need in the art for novel MCHR1 antagonists that are useful as pharmaceuticals, for example, in the treatment of obesity and inflammatory bowel disease.

SUMMARY OF THE INVENTION

The following invention is directed to novel MCHR1 antagonists, methods for using them for the treatment of disease states such as obesity and inflammatory bowel disease, pharmaceutical compositions comprising such antagonists, and pharmaceutical combinations. The present invention is directed to compounds having the following Formula I:

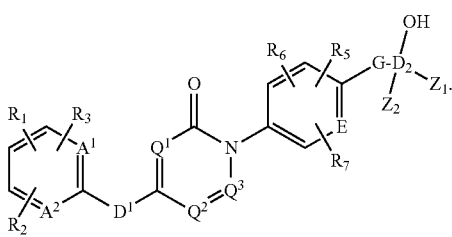

A compound having the following Formula I, or pharmaceutically acceptable salt thereof:

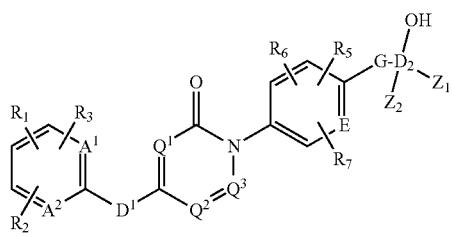

wherein, $A^1$ and $A^2$ are independently C or N;

E is C or N;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, $-CR^8R^9X-$, $-XCR^8R^9-$, $-CHR^8CHR^9-$, $-CR^{10}=CR^{10'}-$, $-C\equiv C-$, or 1,2-cyclopropyl;

X is O, S or $NR^{11}$;

$R^1$, $R^2$, and $R^3$ are independently selected from the group consisting of hydrogen, halogen, substituted or unsubstituted $C_1$ to $C_4$ alkyl, substituted or unsubstituted $C_3$ to $C_5$ cycloalkyl, $-CF_3$, $-OCF_3$, $-OR^{12}$, substituted or unsubstituted phenyl and $-SR^{12}$;

G is O, S or $-NR^{15}$;

$D^2$ is substituted or unsubstituted $C_2$ to $C_4$ alkyl, substituted or unsubstituted substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-substituted or unsubstituted $C_3$ to $C_5$ cycloalkoxy or when G is $-NR^{15}$, G and $D^2$ together may optionally form an azetidine, pyrrolidine or piperidine ring;

$Z_1$ and $Z_2$ are independently hydrogen, halogen, substituted or unsubstituted $C_1$ to $C_3$ alkyl, substituted or unsubstituted $C_3$ to $C_5$ cycloalkyl, $-OCH_3$, substituted or unsubstituted $C_3$ to $C_5$ cycloalkoxy, halo, $-CF_3$, $-OCONR^{14}R^{14'}$, $-CN$, $-CONR^{14}R^{14'}$, $-SOR^{12}$, $-SO_2R^{12}$, $-NR^{14}COR^{14'}$, $-NR^{14}CO_2R^{14'}$, $-CO_2^{12}$, $NR^{14}SO_2R^{12}$ or $-COR^{12}$;

$R^5$, $R^6$, and $R^7$ are independently selected from the group consisting of hydrogen, halogen, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, $-CF_3$, $-SR^{12}$, $-OCH_3$, $-OCH_2CH_3$, $-CN$, $-CONR^{14}R^{14'}$, $SOR^{12}$, $SO_2R^{12}$, $NR^{14}COR^{14'}$, $NR^{14}CO_2R^{12}$, $CO_2R^{12}$, $NR^{14}SO_2R^{12}$ and $-COR^{12}$;

$R^8$, $R^9$, $R^{10}$, $R^{11}$ are independently hydrogen or $-CH_3$;

$R^{12}$ is substituted or unsubstituted $C_1$ to $C_4$ alkyl or substituted or unsubstituted $C_3$ to $C_5$ cycloalkyl;

$R^{14}$ and $R^{14'}$ are independently H, substituted or unsubstituted $C_1$ to $C_3$ alkyl, substituted or unsubstituted $C_3$ to $C_5$ cycloalkyl or $R^{14}$ and $R^{14'}$ together with the N to which they are attached form a ring having 4 to 7 atoms;

$R^{15}$ is independently selected from the group consisting of hydrogen and substituted or unsubstituted $C_1$ to $C_4$ alkyl; and wherein said prodrugs of Formula I are selected from the group consisting of amino acid esters, monoesters of dicarboxylic acids and monoesters of phosphoric acid and incorporate the hydroxyl group that is attached to D.

According to one aspect of the present invention, compounds have the Formula I as described above, wherein $R^1$, $R^2$, and $R^3$ are each independently H, halo, substituted or unsubstituted $C_3$ to $C_5$ cycloalkoxy, $-CF_3$, or $-CH_2F_5$.

According to one aspect of the present invention, G is O.

According to one aspect of the present invention, $D^2$ is $-CH_2C-$.

According to one aspect of the present invention, $Z_1$ and $Z_2$ are both $-CH_3$ or halo, or $Z_1$ is H and $Z_2$ is $C_3$ to $C_5$ cycloalkyl, preferably cyclopropyl.

According to one aspect of the present invention, $D^1$ is a bond, $-CR^8R^9X-$, $-XCR^8R^9-$, $-CR^{10}=CR^{10}-$, or $-C\equiv C-$ and X is O, S, $-SO_2$ or $-NR^{11}$.

In one embodiment of the present invention, the compounds have the following Formula I:

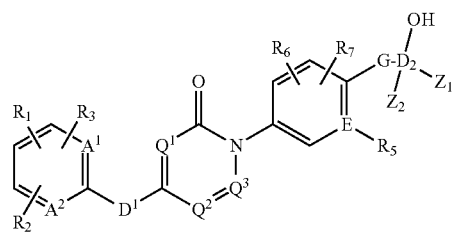

wherein $R_1$, $R_2$, and $R_3$ are independently H, halo, $C_1$ to $C_6$ alkyl, or $CF_3$;

$A^1$ is C or N;

$A^2$ is C;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, $-CR^8R^9X-$, $-XCR^8R^9-$, 1,2 cyclopropyl, $-CR^{10}=CR^{10'}-$ or $-C\equiv C-$;

X is O, S, $-NR^{11}$;

$R^8$, $R^9$, $R^{10}$, $R^{10'}$, and $R^{11}$ are each independently H or $C_1$ to $C_6$ alkyl;

$R^5$ is $-CH_3$ or $-OCH_3$, and $R^6$ and $R^7$ are H;

G is O or S;

$D^2$ is $-CH_2C-$ or $-CH_2$-cyclobutyl;

$Z^1$ and $Z^2$ are both —CH$_3$, halo, or $Z^1$ is H and $Z^2$ is cyclopropyl wherein said prodrugs of Formula I are selected from the group consisting of amino acid esters, monoesters of dicarboxylic acids and monoesters of phosphoric acid and incorporate the hydroxyl group that is attached to D.

DETAILED DESCRIPTION OF THE INVENTION

The present invention is directed to compounds, including all stereoisomers, salts, solvates, prodrugs, isotopes, and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression, anxiety or intestinal inflammation by administration of a therapeutically effective dose of a compound according to Formula I.

The present invention is directed to compounds according to Formula I, or a prodrug thereof or a pharmaceutically acceptable salt thereof:

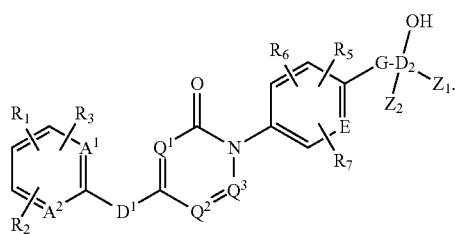

A compound having the following Formula I, or pharmaceutically acceptable salt thereof:

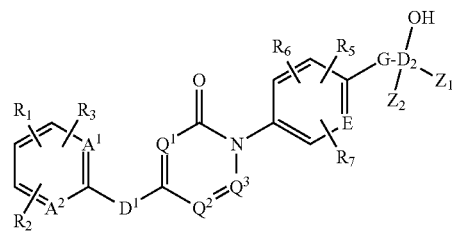

wherein, $A^1$ and $A^2$ are independently C or N;

E is C or N;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, —CR$^8$R$^9$X—, —XCR$^8$R$^9$—, —CHR$^8$CHR$^9$—, —CR$^{10}$=CR$^{10'}$—, —C≡C—, or 1,2-cyclopropyl;

X is O, S or NR$^{11}$;

$R^1$, $R^2$, and $R^3$ are independently selected from the group consisting of hydrogen, halogen, substituted or unsubstituted $C_1$ to $C_4$ alkyl, substituted or unsubstituted $C_3$ to $C_5$ cycloalkyl, —CF$_3$, —OCF$_3$, —OR$^{12}$, substituted or unsubstituted phenyl and —SR$^{12}$;

G is O, S or —NR$^{15}$;

$D^2$ is substituted or unsubstituted $C_2$ to $C_4$ alkyl, substituted or unsubstituted substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-substituted or unsubstituted $C_3$ to $C_5$ cycloalkoxy or when G is —NR$^{15}$, G and $D^2$ together may optionally form an azetidine, pyrrolidine or piperidine ring;

$Z_1$ and $Z_2$ are independently hydrogen, halogen, substituted or unsubstituted $C_1$ to $C_3$ alkyl, substituted or unsubstituted $C_3$ to $C_5$ cycloalkyl, —OCH$_3$, substituted or unsubstituted $C_3$ to $C_5$ cycloalkoxy, halo, —CF$_3$, —OCONR$^{14}$R$^{14'}$, —CN, —CONR$^{14}$R$^{14'}$, —SOR$^{12}$, —SO$_2$R$^{12}$, —NR$^{14}$COR$^{14'}$, —NR$^{14}$CO$_2$R$^{14'}$, —CO$_2$R$^{12}$, NR$^{14}$SO$_2$R$^{12}$ or —COR$^{12}$;

$R^5$, $R^6$, and $R^7$ are independently selected from the group consisting of hydrogen, halogen, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, —CF$_3$, —SR$^{12}$, —OCH$_3$, —OCH$_2$CH$_3$, —CN, —CONR$^{14}$R$^{14'}$, SOR$^{12}$, SO$_2$R$^{12}$, NR$^{14}$COR$^{14'}$, NR$^{14}$CO$_2$R$^{12}$, CO$_2$R$^{12}$, NR$^{14}$SO$_2$R$^{12}$ and —COR$^{12}$;

$R^8$, $R^9$, $R^{10}$, $R^{10'}$, $R^{11}$ are independently hydrogen or —CH$_3$;

$R^{12}$ is substituted or unsubstituted $C_1$ to $C_4$ alkyl or substituted or unsubstituted $C_3$ to $C_5$ cycloalkyl;

$R^{14}$ and $R^{14'}$ are independently H, substituted or unsubstituted $C_1$ to $C_3$ alkyl, substituted or unsubstituted $C_3$ to $C_5$ cycloalkyl or $R^{14}$ and $R^{14'}$ together with the N to which they are attached form a ring having 4 to 7 atoms;

$R^{15}$ is hydrogen or substituted or unsubstituted $C_1$ to $C_4$ alkyl; and further provided that prodrugs of Formula I are selected from the group consisting of amino acid esters, monoesters of dicarboxylic acids or monoesters of phosphoric acid incorporating the hydroxyl group that is attached to D.

According to one preferred embodiment of the present invention, $R^1$, $R^2$, and $R^3$ are each independently H, halo, —OCH$_3$, —OCF$_3$ or —CF$_3$.

According to one preferred embodiment of the present invention, G is O.

According to one preferred embodiment of the present invention, $D^2$ is —CH$_2$C—.

According to one preferred embodiment of the present invention, $D^2$ is —CH$_2$-cyclobutyl.

According to one preferred embodiment of the present invention, $D^1$ is a bond, —CR$^8$R$^9$X—, —XCR$^8$R$^9$—, —CR$^{10}$=CR$^{10'}$—, or —C≡C— and X is O, S, —SO$_2$ or —NR$^{11}$.

According to one preferred embodiment of the present invention, $Z^1$ and $Z^2$ are each —CH$_3$.

According to one preferred embodiment of the present invention, $Z^1$ and $Z^2$ are each —F.

According to one preferred embodiment of the present invention, $Z^1$ is H and $Z^2$ is cyclopropyl.

According to one preferred embodiment of the present invention, compounds of the present invention have the following Formula Ia, and include pharmaceutically acceptable salts and prodrugs thereof:

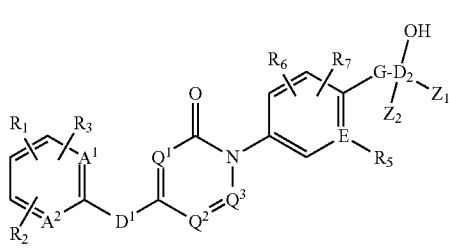

wherein $R_1$, $R_2$, and $R_3$ are independently H, halo, substituted or unsubstituted $C_1$ to $C_4$ alkyl, or $CF_3$;

$A^1$ is C or N;

$A^2$ is C;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, —$CR^8R^9X$—, —$XCR^8R^9$—, —$CR^{10}$=$CR^{10'}$ or —C≡C—;

X is O, S, —$NR^{11}$;

$R^8$, $R^9$, $R^{10}$, $R^{10'}$ and $R^{11}$ are each independently H;

$R^5$ is —$CH_3$ or —$OCH_3$;

$R^6$ and $R^7$ are H;

G is O or S;

$D^2$ is —$CH_2C$— or —$CH_2$-cyclobutyl;

$Z^1$ and $Z^2$ are both —$CH_3$ or $Z^1$ is H and $Z^2$ is cyclopropyl; and

Wherein said prodrugs of Formula I are selected from the group consisting of amino acid esters, monoesters of dicarboxylic acids and monoesters of phosphoric acid and incorporate the hydroxyl group that is attached to D.

According to another aspect of the present invention, pharmaceutical compositions that are useful for the treatment of obesity and obesity related illnesses are provided, comprising a therapeutically effective amount of a compound according to Formula I, as defined herein, together with a pharmaceutically acceptable carrier or diluent.

According to one aspect of the present invention, methods are provided for treating a patient suffering from an MCHR1 modulated disease or disorder such as, for example, obesity, diabetes, depression, anxiety or intestinal inflammation such as inflammatory bowel disease, colitis or Crohn's disease by administration of a therapeutically effective dose of a compound according to Formula I, optionally in combination with other therapeutic agents, such as those described below.

In preferred embodiments of the present invention, methods are provided for treating obesity in a patient in need of such treatment, comprising administering to a patient in need of such treatment, a therapeutically effective amount of a compound according to Formula I, optionally in combination with another anti-obesity agent.

In one preferred embodiment of the present invention, pharmaceutical combinations are provided, comprising a compound according to Formula I and at least one additional therapeutic agent selected from the group consisting of an acetyl-cholinesterase inhibitor; a muscarinic receptor-1 agonist, a nicotinic agonist, a glutamic acid receptor (AMPA and NMDA) modulator, a nootropic agent, an agent for Alzheimer's disease, an agent for treatment of Parkinson's disease, anti-hyperlipidemia agent, an anti-obesity agent; anti-diabetic agent, appetite suppressant; HDL-raising agent, cognition enhancing agent, an agent used to treat neurodegeneration, an agent used to treat bowel disorders, an anti-inflammatory agent; anti-anxiety agent; an anti-depressant; and an anti-sleep disorder agent.

The present invention is further directed to methods for treating diabetes comprising administering to a patient in need of such treatment a pharmaceutically effective amount of a compound according to Formula I, optionally in combination with a further anti-diabetic agent as described herein.

The present invention is further directed to the use of a compound according to Formula I in the manufacture of a medicament for the treatment of obesity.

The present invention is further directed to the use of compound according to Formula I in the manufacture of a medicament for the treatment of diabetes.

The present invention is further directed to the use of a compound according to Formula I in the manufacture of a medicament for the treatment of inflammatory bowel disease.

The present invention is further directed to the use of a compound according to Formula I in the manufacture of a medicament for the treatment of depression.

The present invention is further directed to the use of a compound according to Formula I in the manufacture of a medicament for the treatment of anxiety.

DEFINITIONS

Unless otherwise indicated, the term alkyl as employed herein alone or as part of another group includes both straight and branched chain hydrocarbons containing the terms "alkyl" and "alk" as employed herein alone or as part of another group includes both straight and branched chain hydrocarbons. Preferred alkyl groups of the present invention include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and may also be substituted with groups including halo, preferably F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Preferred alkyl groups of the present invention include $C_1$, $C_2$, $C_3$ and $C_4$ alkyl groups that are optionally substituted with F, such as —$CF_3$, —$C_2F_5$, or —$C_3F_7$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

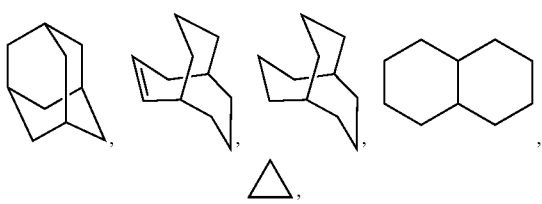

any of which groups may be optionally substituted with substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents. Preferred "cycloalkyl" groups of the present invention include $C_3$ to $C_5$ carbon atoms, such as cyclopropyl, or cyclobutyl, or cyclopentyl.

Unless otherwise indicated, the term "cycloalkoxy" as employed herein alone or as part of another group, represents a 4-, 5- or 6-membered saturated ring containing an oxygen in the ring and includes

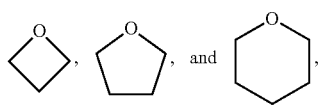

and which may be optionally substituted with 1 or 2 of any of the substituents as set out for cycloalkyl.

The term alkylcycloalkyl, wherein the number of carbon atoms may be specified, e.g., "$C_2$ to $C_3$ alkyl-$C_3$ to $C_5$ cycloalkyl" refers to a group bonded through the cycloalkyl portion. For example, "$C_1$ alkyl-$C_6$ cycloalkyl" refers to the group

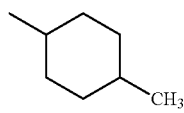

while the term "cycloalkylalkyl" refers to a cycloalkyl group bonded through the alkyl portion, such as

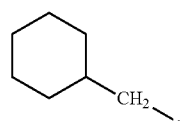

The term "alkylcycloalkoxy" refers to an alkyl group bonded to the rest of the molecule via the cycloalkoxy portion.

The terms "heterocyclo", "heterocyclyl" or "heterocyclic" as used herein, alone or as part of another group, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, or oxadiazolyl or other heterocycles described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. The heterocycloalkyl may optionally be substituted with at least one of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "halogen" or "halo" as used herein alone or as part of another group refers to chlorine, bromine, fluorine, and iodine, with chlorine or fluorine being preferred.

The term "aryl" herein alone or as part of another group refers to monocyclic or bicyclic aromatic rings, e.g., phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds. *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. Further, "heteroaryl", as defined herein, may optionally be substituted with one or more substituents such as the substituents included above in the definition of "substituted alkyl" and "substituted aryl". Examples of heteroaryl groups include the following:

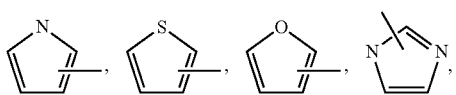

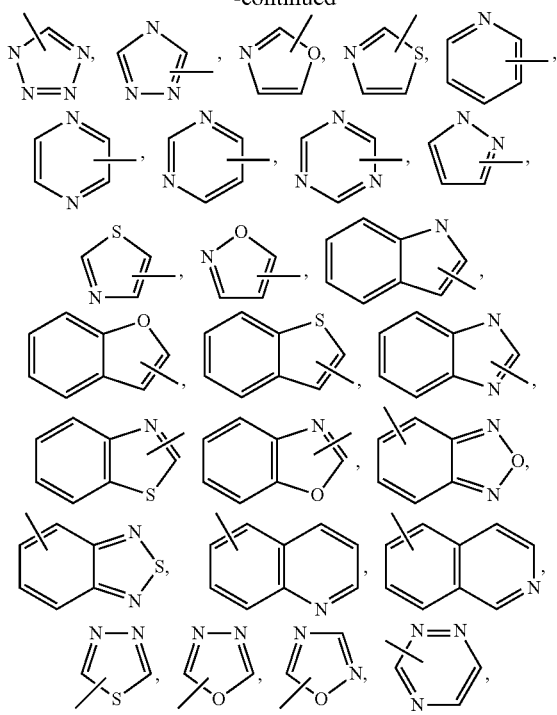

and the like.

Unless otherwise indicated, the term "alkoxy", "aryloxy" or "aralkoxy" as employed herein alone or as part of another group includes any of the above alkyl, aralkyl or aryl groups linked to an oxygen atom.

METHODS OF USE

According to one embodiment of the present invention, methods are provided for treating obesity in a patient in need of such treatment, which includes the step of administering a therapeutically effective amount of at least one compound according to Formula I alone or in combination with one or more additional anti-obesity agents, wherein the obesity agent is selected from those described herein.

According to one embodiment of the present invention, methods are provided for treating diabetes, especially Type II diabetes, which includes the step of administering a therapeutically effective amount of at least one compound according to Formula I alone or in combination with one or more additional anti-diabetic agents to a patient in need of such treatment, wherein the anti-diabetic agent is described herein.

According to one embodiment of the present invention, methods for treating depression are provided, which includes the step of administering a therapeutically effective amount of at least one compound according to Formula I to a patient in need of such treatment.

According to one embodiment of the present invention, methods are provided for treating anxiety, which includes the step of administering to a patient in need of such treatment a therapeutically effective amount of a compound having Formula I.

According to another embodiment of the present invention, methods are provided for treating intestinal inflammatory conditions, such as inflammatory bowel disease (IBD), colitis and Crohn's disease (CD) in a patient in need of such treatment which includes the step of administering a therapeutically effective amount of a compound of Formula I.

UTILITY

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

DOSAGE FORMS

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed.

Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

DOSAGES

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

PHARMACEUTICAL COMBINATIONS

The present invention includes within its scope pharmaceutical compositions comprising a therapeutically effective amount of at least one of the compounds of Formula I, together with a pharmaceutically acceptable carrier or diluent. Optionally, compounds of the present invention can be used alone, in combination with other suitable therapeutic agents useful in the treatment of the aforementioned disorders including: anti-obesity agents; anti-diabetic agents, appetite suppressants; lipid-lowering agents, HDL-raising agents, cognition enhancing agents, agents used to treat neurodegeneration, agents used to treat bowel disorders, anti-inflammatory agents; anti-anxiety agents; and anti-depressants.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, such as dapagliflozin, DPP4 inhibitors, triple monoamine reuptake inhibitors, CCK agonists, GLP-1 agonists, and other Pre-proglucagon-derived peptides; NPY1 or NPY5 antagonist, NPY2 and NPY4 modulators, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

Examples of suitable anti-diabetic agents for use in combination with the compounds of the present invention include: oral antihypergycemic agents, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glucokinase inhibitors, glycogen phosphorylase inhibitors, and/or meglitinides, as well as insulin, and/or glucagon-like peptide-1 (GLP-1), GLP-1 agonist, a PTP-1B inhibitor (protein tyrosine phosphatase-1B inhibitor), and/or a histone deacetylase modulator such as a SIRT1 activator.

The compounds of the present invention may be employed in combination with anti-hyperlipidemia agents, or agents used to treat arteriosclerosis. An example of an hypolipidemic agent would be a fabric acid derivatives, bile acid sequestrants, nicotinic acid, aspirin, poly(diallylmethylamine) derivatives, quaternary amine poly(diallyldimethylammonium chloride) and ionenes and other known serum cholesterol lowering agents.

Hypolipidemic agents include ACAT inhibitors, an upregulator of LDL receptor activity, and cholesterol absorption inhibitors.

Lipid agent or lipid-modulating agents include cholesteryl transfer protein inhibitors (CETP) The hypolipidemic agent may be an ileal $Na^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compounds, a beta-lactam cholesterol absorption inhibitor, a PPAR α-agonist and/or an FXR agonist; an LDL catabolism promoter, a sodium-proton exchange inhibitor; an LDL-receptor inducer or a steroidal glycoside; an anti-oxidant, an antihomocysteine agent, a cholesterol absorption inhibitor, an HMG-CoA synthase inhibitor, or a lanosterol demethylase inhibitor, a sterol regulating element binding protein-I (SREBP-1).

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of MCHR1 modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines, 5HT1A receptor agonists, and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs), monoamine oxidase inhibitors, reversible inhibitors of monoamine oxidase (RIMAs), serotonin and norepinephrine reuptake inhibitors (SNRIs) (venlafaxine), corticotropin releasing factor (CRF) receptor antagonists, alpha-adrenoreceptor antagonists, and atypical antidepressants.

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazines thioxanthine, heterocyclic dibenzazepines, butyrophenone, diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

METHODS OF PREPARATION

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

It will be understood that $R^4$ may be present in its final form throughout the synthesis or can be introduced at any point in the following synthetic sequences particularly if $R^4$ contains an hydroxyl. Specifically, $R^4$ may be carried along as a truncated moiety $R^{4'}$ such as GH that may be protected as a SEM ether, SEM thioether, BOC amine or etc. and then elongated whenever appropriate. Likewise compounds of Formula I for which $D^1$ is $SOCH_2$ or $SO_2CH_2$ can be prepared by treatment of compounds of Formula I where $D^1$ is $SCH_2$ with one or two equivalents respectively of an oxidant such as m-chloroperbenzoic acid in a solvent such as $CH_2Cl_2$.

Scheme 1 below portrays a generalized reaction sequence for the synthesis of compounds of Formula IA for which $Q^1$ is nitrogen and $Q^2$ and $Q^3$ are CH and $D^1$ is $CH_2O$, $CH_2S$, or $CH_2NR^{11}$. Compounds of Formula V may be prepared by N-arylation of the readily available S-methylthiouracil derivative II with aryl or heteroaryl bromides III or alternatively with aryl or heteroaryl boronic acids IV. Treatment of II with aryl or heteroaryl bromides III in the presence of catalytic amounts of Cu(I)iodide, potassium phosphate and an amine ligand (e.g., N1,N2-dimethylcyclohexane-1,2-diamine, N1,N2-dimethylethylenediamine) in solvents such as dioxane or DMF at 50 to 150° C. affords V. Alternatively, V can be prepared by coupling compound of Formula II with aryl or heteroaryl boronic acids IV in the presence of catalytic amounts of $CuOAc_2$ and an amine (e.g., triethylamine, N1,N1,N2,N2-tetramethylethylenediamine) or pyridine in solvents such as $CH_2Cl_2$ or MeOH etc. Treatment of V with thiols of Formula VI at elevated temperatures (50-150° C.) affords the corresponding compounds of Formula 1A. This condensation reaction can be carried out in neat thiols or in solvents (e.g., DMF, NMP, THF or DME and the like) with or without the presence of a base (e.g., TEA, potassium carbonate etc.). A similar condensation proceeds readily with the amine counterpart VII whereas the corresponding condensation with alcohols of Formula VIII generally requires the presence of an above mentioned base.

Scheme 1

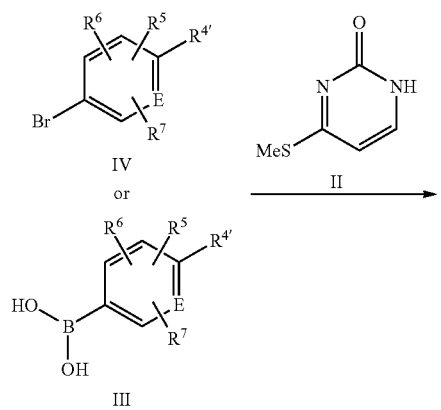

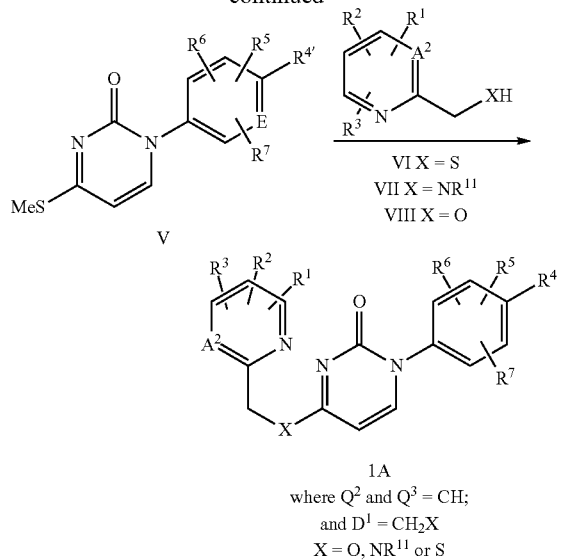

Scheme 2 depicts a generalized synthetic route for preparation of compounds of formula IB (wherein $Q^1$=N, $Q^2$=CH and $Q^3$=CH, $D^1$=CH=CH, ethinyl and

from uracil (IX). Thus, treatment of uracil with trityl chloride in the presence of a base (e.g., sodium or potassium carbonate) in solvents such as DMF, NMP or DMSO affords X. Optionally, one may use other protecting groups such as benzyl, p-methoxybenzyl and the like. The trityl uracil intermediate X can be converted to the sulfonate XI by treatment with 2,4,6-triisopropylbenzenesulfonyl chloride in the presence a base such as sodium or potassium hydride in DMF, THF etc. Alternatively, one may choose to prepare a different sulfonate derivative by using appropriate sulfonyl halides. Compound XI can be converted to compounds of Formula XII via a Stille or Suzuki-Miyaura coupling reactions with suitable tin compounds of Formula XIII or boronic acid derivatives of Formula XIV. The pyrimidinones of Formula XII can be transformed to the compounds of formula IF by N-arylation with compounds of Formula III or Formula IV as described for Scheme 1. Similarly N-arylation of compounds of Formula XV, prepared by coupling compounds of Formula XI with compounds of Formula XVI, generates compounds of Formula IB where $D^1$ is ethinyl.

Scheme 2

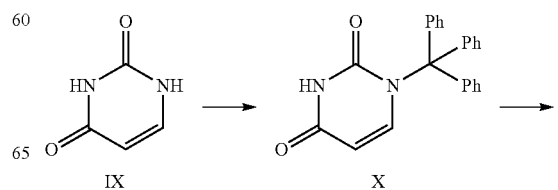

-continued

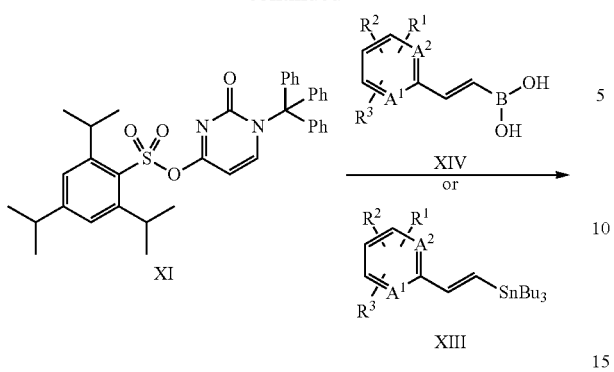

XI

XIV
or

XIII

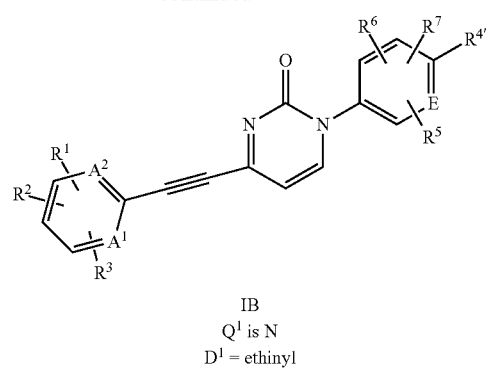

IB
$Q^1$ is N
$D^1$ = ethinyl

Compounds of formula IC (wherein $Q^1$=N, $Q^2$ and $Q^3$=CH, and $D^1$ is $OCH_2$) can be prepared as outlined in Scheme 3. Those compounds of Formula 1C where $A^1$ and $A^2$=CH can be prepared from the readily available pyrimidine XVII via a Mitsunobu reaction (DEAD/$Ph_3P$, DIAD/$Ph_3P$ in THF or DME etc.) with various phenols XVIII to afford XIX. Oxidation of the sulfide XIX (using mCPBA, OXONE® etc.) in solvents such as $CH_2Cl_2$ or 1,2-dichloroethane affords sulfone XX which can be converted to the pyrimidinone XXI via hydrolysis with aqueous sodium or potassium hydroxide, or potassium carbonate in solvents such as THF, dioxane and the like. N-arylation of compounds of Formula XXI with compounds of Formula III or IV as described in Scheme 1 generates compounds of formula IC. Similarly compounds of formula IC (wherein one or both of $A^1$ and $A^2$=N) can be prepared upon sequential treatment of pyrimidine XVII with NaH in a solvent such as DMF followed by addition of compounds of Formula XXII to generate compounds of formula XXIII. Subsequent oxidation, hydrolysis of the resultant sulfone and N-arylation completes the transformation to 1C.

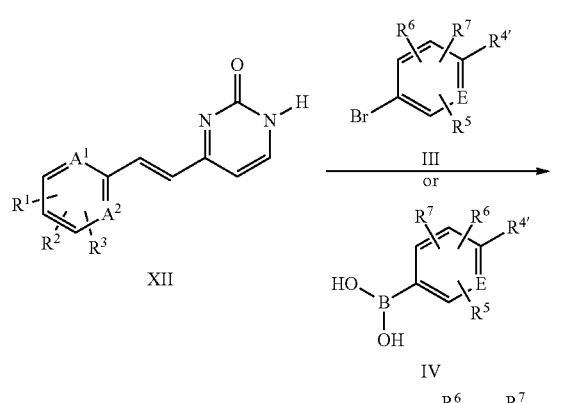

XII

III or IV

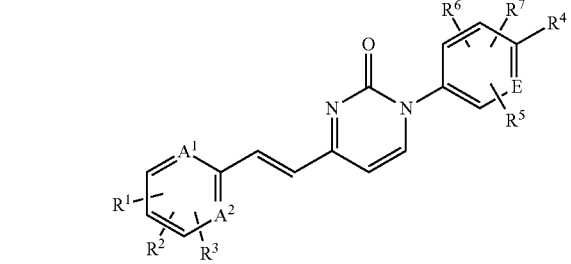

IB
$Q^1$ is N
$D^1$ = vinyl

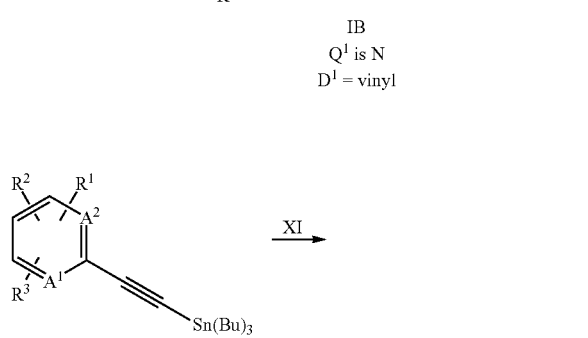

XVI

XI

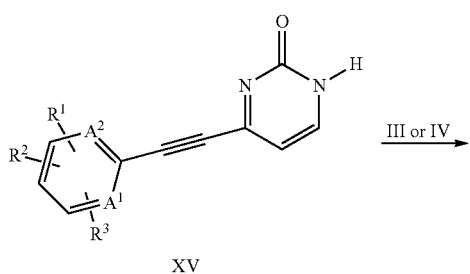

XV

III or IV

Scheme 3

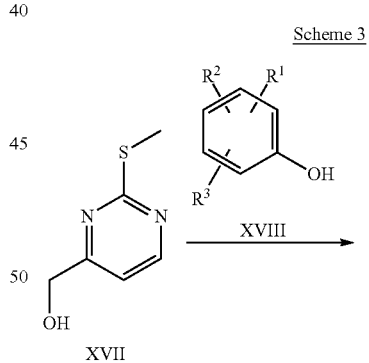

XVII

XVIII

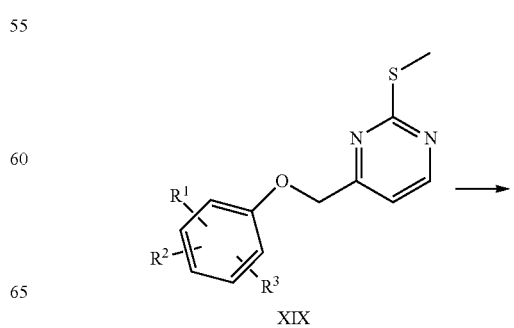

XIX

-continued

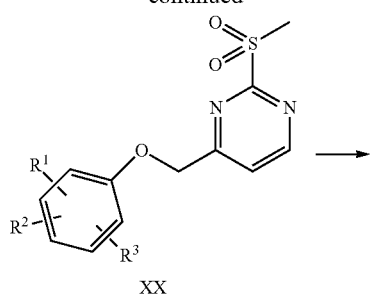
XX

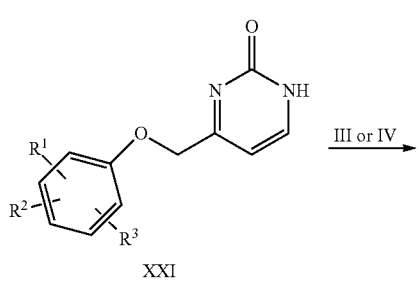
XXI

III or IV →

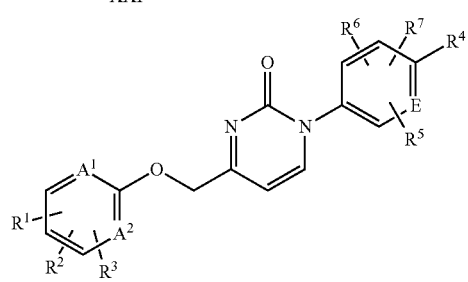
1C
$A^1$, $A^2$ = CH
$D^1$ is $OCH_2$

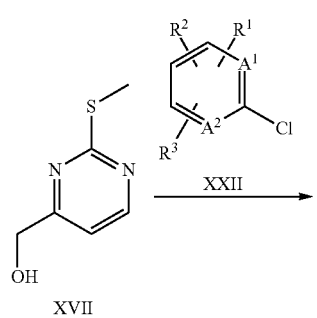
XVII

XXII →

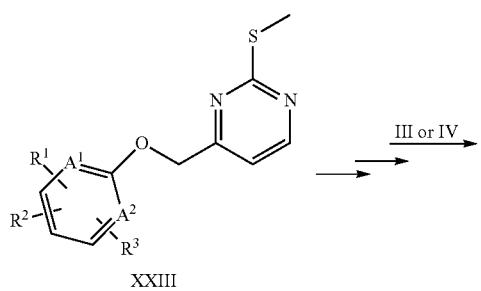
XXIII

III or IV →

-continued

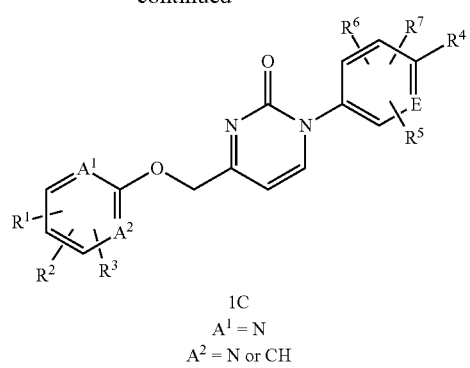
1C
$A^1$ = N
$A^2$ = N or CH
$D^1$ is $OCH_2$

Compounds of formula 1D (wherein $Q^1$ and $Q^2$ are CH and $Q^3$ is nitrogen, $D^1$=CH=CH, ethinyl and

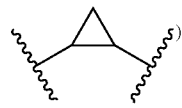

can be prepared from the known 5-iodopyridazine XXIV as shown in Scheme 4. Thus, treatment of XXIV with trityl chloride in the presence of a base (e.g., sodium or potassium carbonate) in solvents such as DMF, NMP or DMSO affords XXV. Optionally, one may use other protecting groups such as benzyl, p-methoxybenzyl and the like. Compounds of formula XXVI can be prepared by coupling XXV to suitable tin compounds of Formula XIV or boronic acid derivatives of formula XIII as previously described in Scheme 2. The pyridazines of Formula XXVI can be transformed to the compounds of formula 1D by reaction with compounds of formula III or formula IV as described for Scheme 1. Similar N-arylation of compounds of formula XXVII, prepared by coupling compounds of formula XXVI with compounds of formula XXVIII, generates compounds of formula ID where $D^1$ is ethinyl. Compounds of 1D where $D^1$ is 1,2-cyclopropyl can be prepared from 5-iodopyridazine XXIV. Treatment of XXIV with a strong base such as lithium, sodium or potassium bis(trimethylsilyl)amide and $(Boc)_2O$ in THF, DMF and the like affords XXIX. Compounds of formula XXXI can be obtained by heating XXIX with compounds of Formula XXX in a solvent such as toluene/water containing a catalyst such as palladium(II) acetate and a metal ligand such as tricyclohexylphosphine. Subsequent N-arylation of compounds of Formula XXXI as previously described in Scheme 1 with compounds of formula III or formula IV generates compounds of Formula 1D where $D^1$ is 1,2-cyclopropyl.

Scheme 4

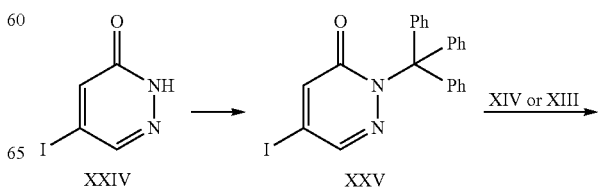
XXIV    XXV

XIV or XIII →

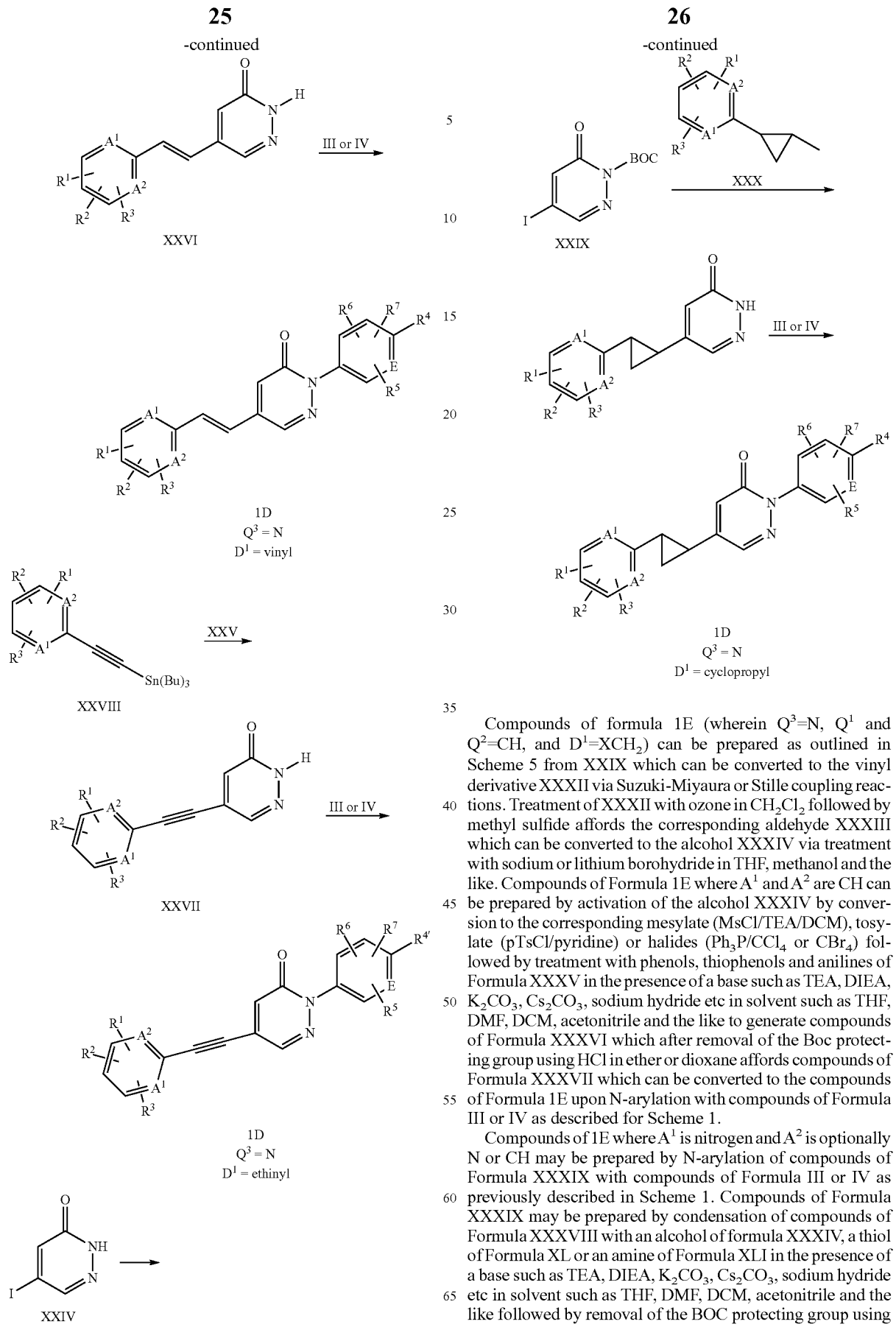

Compounds of formula 1E (wherein $Q^3$=N, $Q^1$ and $Q^2$=CH, and $D^1$=XCH$_2$) can be prepared as outlined in Scheme 5 from XXIX which can be converted to the vinyl derivative XXXII via Suzuki-Miyaura or Stille coupling reactions. Treatment of XXXII with ozone in CH$_2$Cl$_2$ followed by methyl sulfide affords the corresponding aldehyde XXXIII which can be converted to the alcohol XXXIV via treatment with sodium or lithium borohydride in THF, methanol and the like. Compounds of Formula 1E where $A^1$ and $A^2$ are CH can be prepared by activation of the alcohol XXXIV by conversion to the corresponding mesylate (MsCl/TEA/DCM), tosylate (pTsCl/pyridine) or halides (Ph$_3$P/CCl$_4$ or CBr$_4$) followed by treatment with phenols, thiophenols and anilines of Formula XXXV in the presence of a base such as TEA, DIEA, K$_2$CO$_3$, Cs$_2$CO$_3$, sodium hydride etc in solvent such as THF, DMF, DCM, acetonitrile and the like to generate compounds of Formula XXXVI which after removal of the Boc protecting group using HCl in ether or dioxane affords compounds of Formula XXXVII which can be converted to the compounds of Formula 1E upon N-arylation with compounds of Formula III or IV as described for Scheme 1.

Compounds of 1E where $A^1$ is nitrogen and $A^2$ is optionally N or CH may be prepared by N-arylation of compounds of Formula XXXIX with compounds of Formula III or IV as previously described in Scheme 1. Compounds of Formula XXXIX may be prepared by condensation of compounds of Formula XXXVIII with an alcohol of formula XXXIV, a thiol of Formula XL or an amine of Formula XLI in the presence of a base such as TEA, DIEA, K$_2$CO$_3$, Cs$_2$CO$_3$, sodium hydride etc in solvent such as THF, DMF, DCM, acetonitrile and the like followed by removal of the BOC protecting group using HCl in ether or dioxane. The thiol of Formula XL can be prepared from alcohol of Formula XXXIV by a variety of methods by those skilled in the arts; similarly the amine of Formula XLI can be prepared by reductive amination of aldehyde XXXIII.

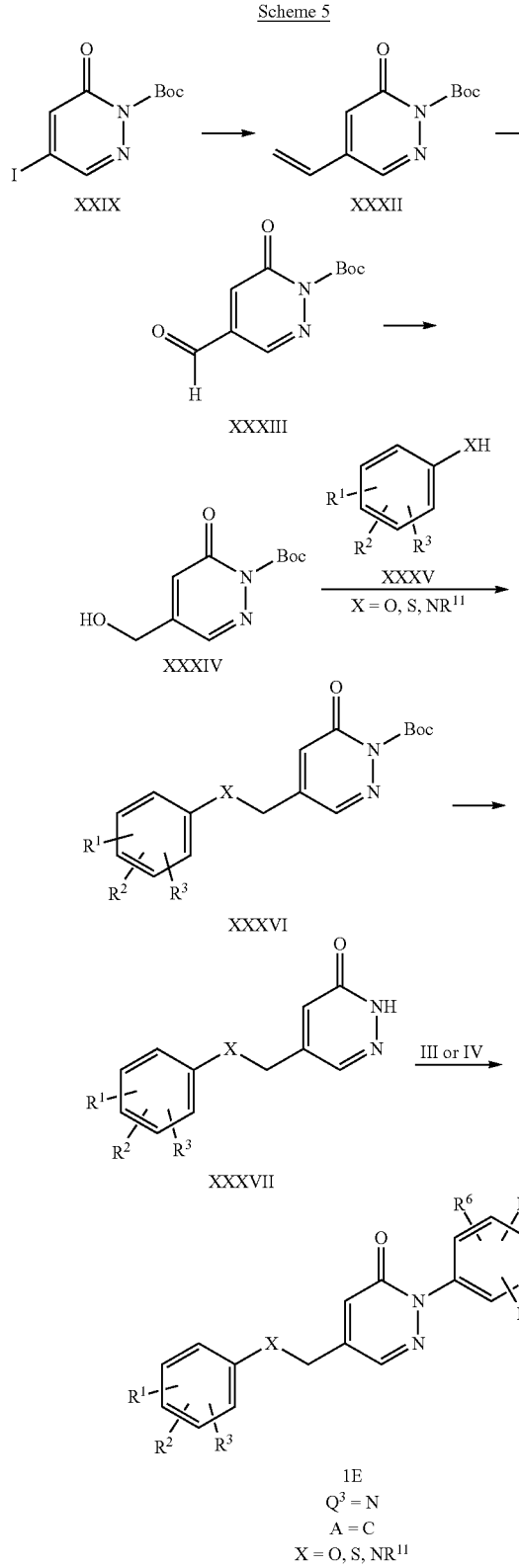

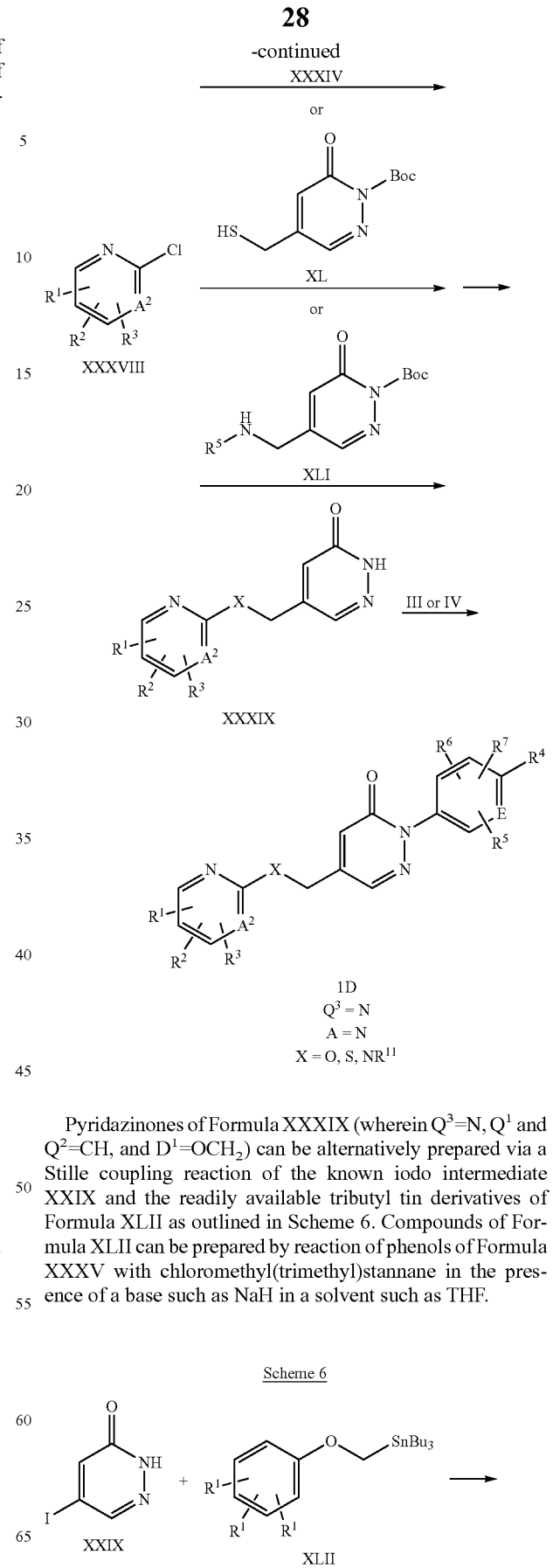

Pyridazinones of Formula XXXIX (wherein $Q^3$=N, $Q^1$ and $Q^2$=CH, and $D^1$=OCH$_2$) can be alternatively prepared via a Stille coupling reaction of the known iodo intermediate XXIX and the readily available tributyl tin derivatives of Formula XLII as outlined in Scheme 6. Compounds of Formula XLII can be prepared by reaction of phenols of Formula XXXV with chloromethyl(trimethyl)stannane in the presence of a base such as NaH in a solvent such as THF.

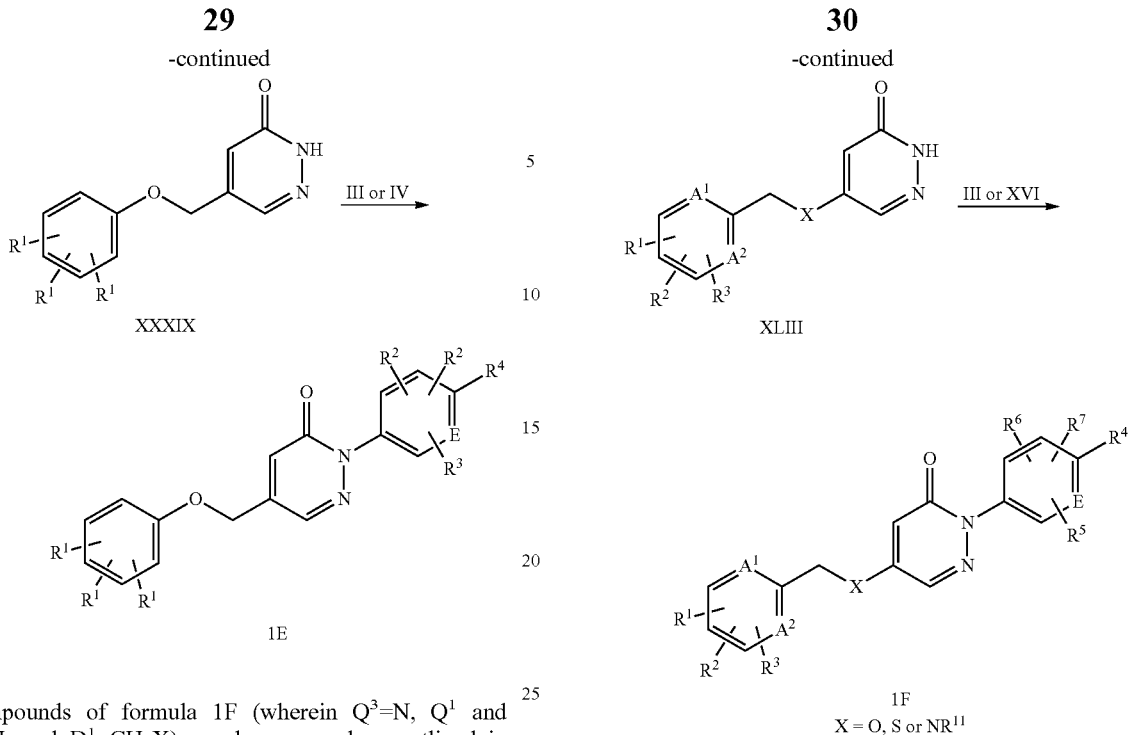

Compounds of formula 1F (wherein $Q^3$=N, $Q^1$ and $Q^2$=CH, and $D^1$=CH$_2$X) can be prepared as outlined in Scheme 7 by direct displacement of the iodo group of the known iodo intermediate XXIV. Treatment of XXIV with thiols of Formula VI or amines of Formula VII in solvents such as DMF, NMP etc. at temperatures ranging from 50 to 150° C. affords compounds of Formula XLIII where X is S or NR$^5$. Optionally, the displacements can be carried out in the presence of a base such as TEA, sodium hydride or potassium carbonate etc. Compounds of Formula XLIII where X is O can be prepared by heating XXIV with alcohols of Formula VIII in the presence of a base such as TEA, sodium hydride or potassium carbonate etc in solvents such as DMF, NMP etc. N-arylation of the resulting pyridazinones of Formula XLIII with Compounds of Formula III or IV as described in Scheme 1 generates compounds of Formula 1F.

Compounds of formula 1G (wherein $Q^2$=N, $Q^1$ and $Q^3$=CH, and $D^1$=XCH$_2$) can be prepared as outlined in Scheme 8 from the commercially available keto ester XLIV via nucleophilic displacement with thiolphenols, phenols or anilines of Formula XXXV in the presence of a base (e.g., potassium carbonate, sodium hydride etc.) in solvents such as DMF, THF, NMP and the like. The resulting keto ester XLV can be converted to the pyrimidinone XLVI via treatment with formamidine acetate in neat phenol at temperatures ranging from 50 to 150° C. The pyrimidinone XLVI can be transformed by N-arylation with compounds of Formula III or IV as described for Scheme 1 to the compounds of formula 1G.

Scheme 7

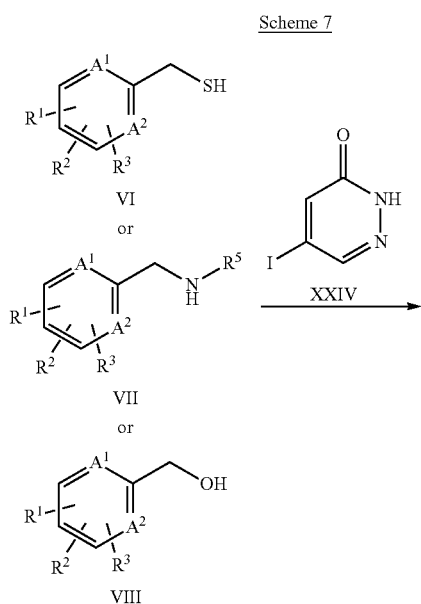

Scheme 8

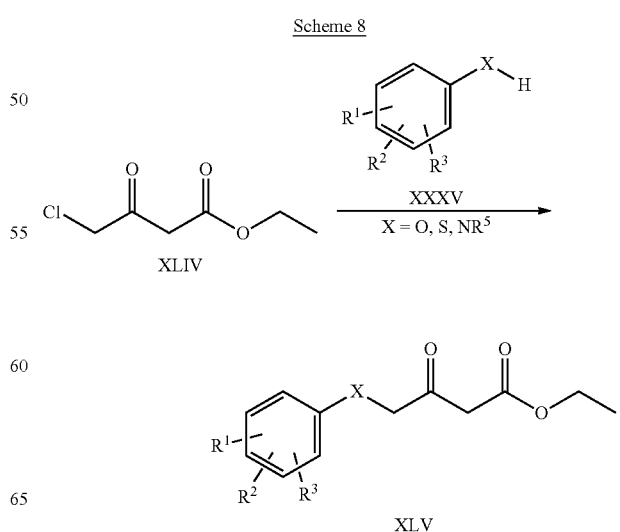

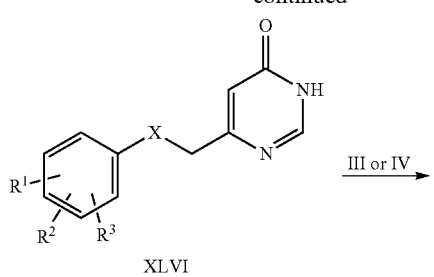

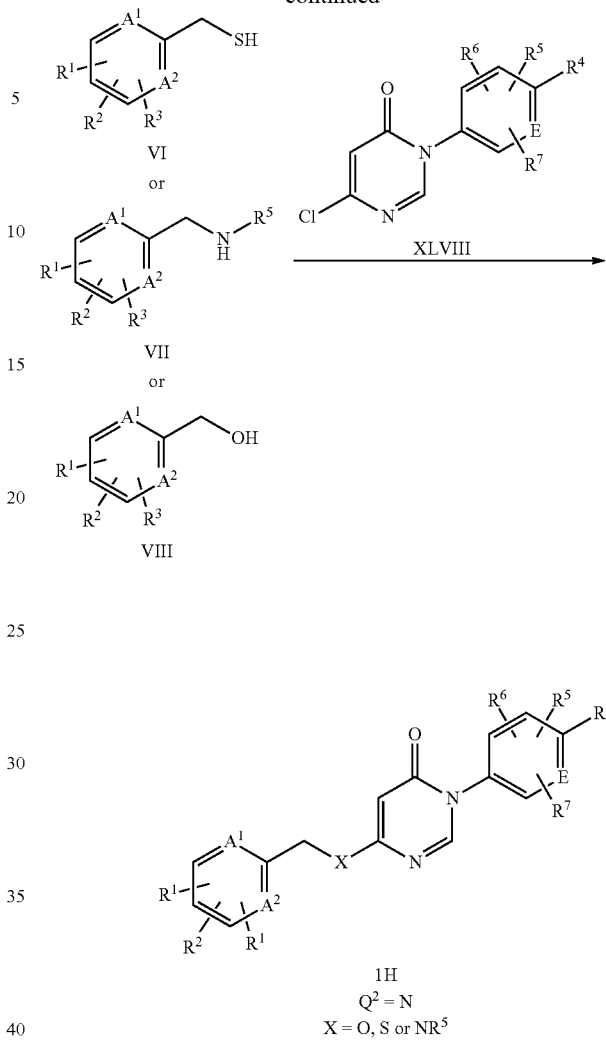

Compounds of formula 1H wherein $Q^2=N$, $Q^1$ and $Q^3=CH$, and $D^1=CH_2X$) can be prepared as outlined in Scheme 9 from the commercially available chloropyrimidinone XLVII. N-arylation of XLVII with compounds of Formula II or IV as described in Scheme 1 generates compounds of Formula XLVIII. Heating of compounds of Formula XLVIII with thiols of Formula VI, alcohols of Formula VIII or amines of Formula VII in the presence of a base (e.g. potassium carbonate, sodium hydride etc.) in solvents such as DMF, THF, NMP generates compounds of Formula 1H.

Scheme 9

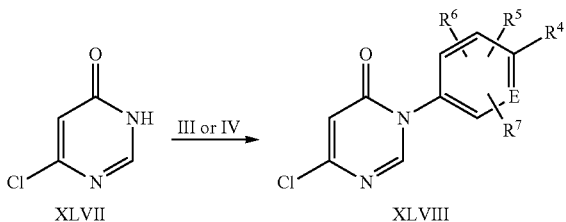

Compounds of formula 1H wherein $Q^2=N$, $Q^1$ and $Q^3=CH$, and $D^1=CH_2O$) can be prepared as outlined in Scheme 10 from the commercially available dihydroxypyridine XLVIII. Alkylation of XLVIII in solvents like DMF or THF in the presence of a base such as potassium carbonate or sodium hydride with compounds of Formula XLIX for which the leaving group is mesylate, tosylate, bromide etc. Compounds of Formula XLIX can be obtained from alcohols of Formula VIII by a variety of methods known to those skilled in the arts. For those instances where the alkylation is not regioselective, the desired alkylated intermediate L can be isolated in pure form by methods known in the art (e.g., chromatography, recrystallization). N-arylation of pyridones of Formula L with compounds of Formula III or IV as described in scheme 1 will generate compounds of formula 1J for which $D^1=CH_2O$.

Scheme 10

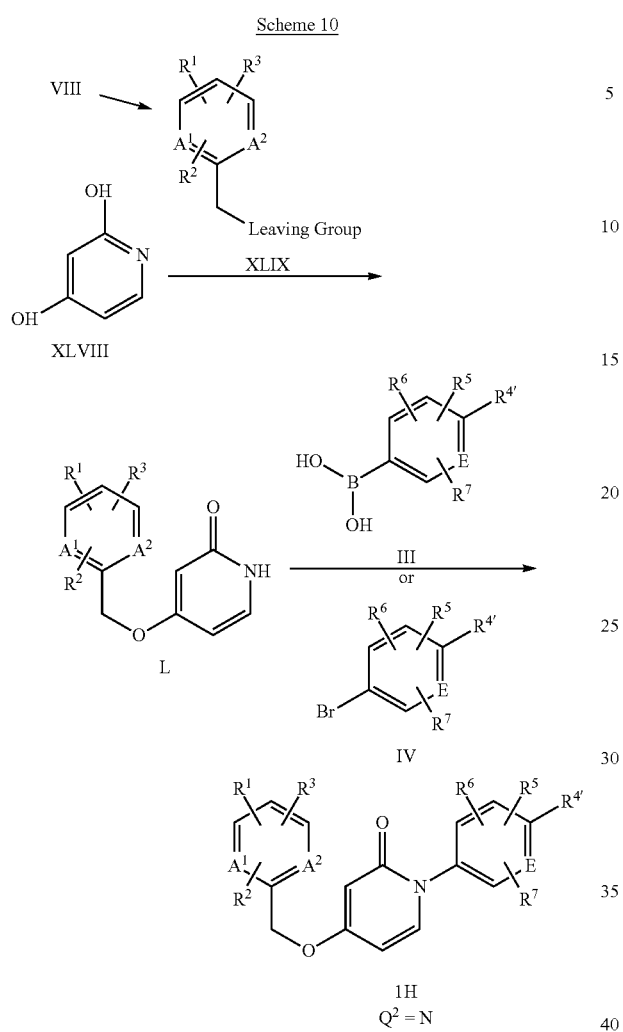

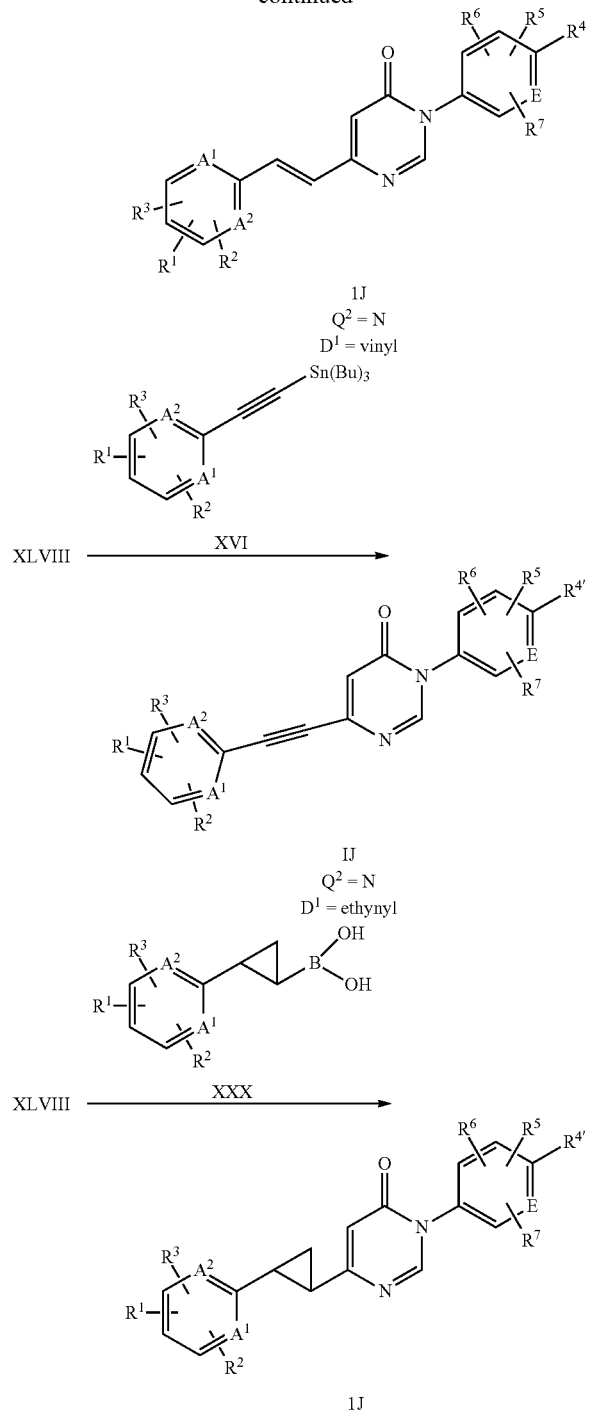

Compounds of formula 1J wherein $Q^2=N$, $Q^1$ and $Q^3=CH$, and $D^1=$vinyl, ethynyl or cyclopropyl can be prepared as outlined in Scheme 11 from compounds of Formula LI. Treatment of LI with readily available boronic acids XIV or tin reagents XIII under the Suzuki-Miyaura or Stille coupling conditions as described in Scheme 2 affords compounds of formula 1J for which $Q^2=N$, $Q^1$ and $Q^3=CH$, and $D^1=$vinyl, ethynyl or cyclopropyl.

Scheme 11

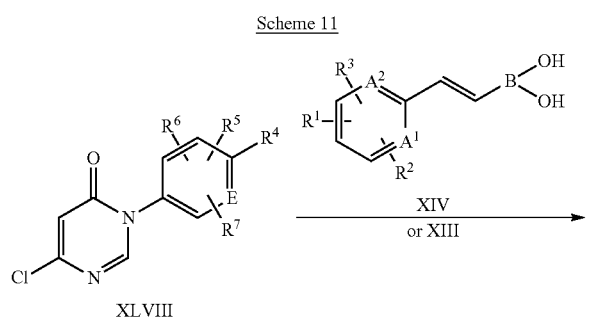

PRODRUGS, SALTS AND STEREOISOMERS

The term "prodrug" encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

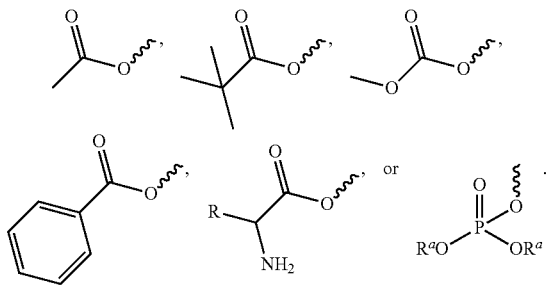

The term "prodrug ethers" include both phosphate acetals and O-glucosides. Representative examples of such prodrug ethers include

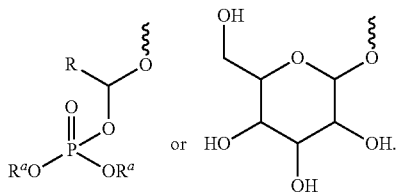

In the above formulae, R is alkyl or H and $R^a$ is H, alkyl, or benzyl.

The compounds of Formula I can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

ABBREVIATIONS

The following abbreviations are employed herein:
Ph=phenyl
Bn=benzyl
t-Bu=tertiary butyl
Me=methyl
NBS=N-bromosuccinimide
NCS=N-chlorosuccinimide
EDC=1-(3-dimethylaminopropyl)-3-ethylcarbodiimide HCl
DIC=2-dimethylaminoisopropyl chloride HCl
PyBop=purum
BOP-Cl=bis(2-oxo-3-oxazolidinyl)-phosphinic chloride
MCPBA=
OTs=Otosyl
OMs=Omesyl
Tf=triflate
AIBN=2,2'-azobisisobutyronitrile
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Palladium tetrakis=Tetrakis(triphenylphosphine)palladium (0)
Ar=argon
$N_2$=nitrogen min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The present invention is illustrated by but not restricted to the examples contained in Tables A-M. The tables also indicate for each example which of nine synthetic methods was employed as well as which of seven analytical methods was utilized. Detailed synthetic procedures as well as analytical HPLC conditions, solvent and column are described in the section after the Tables

TABLE A

| Ex. No. | Structure | Experimental Procedure Used | HPLC Method ($t_R$ Min) | MS (M + H) | NMR Data |
|---|---|---|---|---|---|
| A-1 | 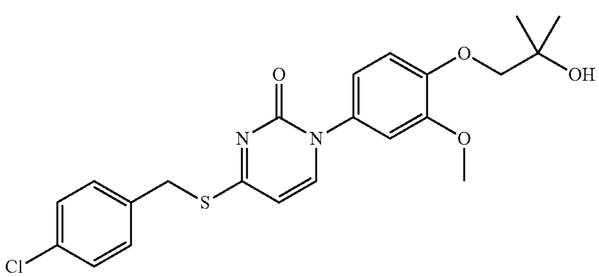 | #1 & #2 | #5 0.93 min | 447 | $^1$H NMR (400 MHz, Chloroform-D) δ ppm 7.33-7.44 (3H, m), 7.24-7.31 (2H, m), 6.91-6.99 (2H, m), 6.86 (1H, dd, J = 8.53, 2.51 Hz), 6.24 (1H, d, J = 7.03 Hz), 4.48 (2H, s), 3.86 (3H, s), 3.85 (2H, s), 1.35 (6H, s). |
| A-2 | 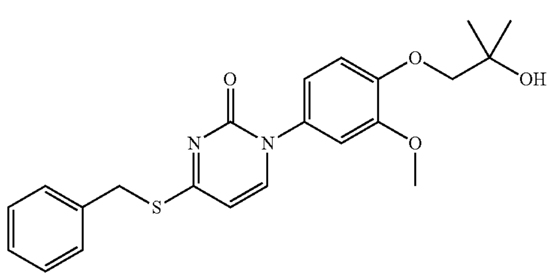 | #2 | #5 0.88 min | 413 | $^1$H NMR (400 MHz, Chloroform-D) δ 7.27-7.52 (6H, m), 6.92-7.02 (2H, m), 6.86 (1H, dd, J = 8.53, 2.51 Hz), 6.24 (1H, d, J = 6.78 Hz), 4.53 (2H, s), 3.87 (3H, s), 3.85 (2H, s), 1.35 (6H, s). |
| A-3 | 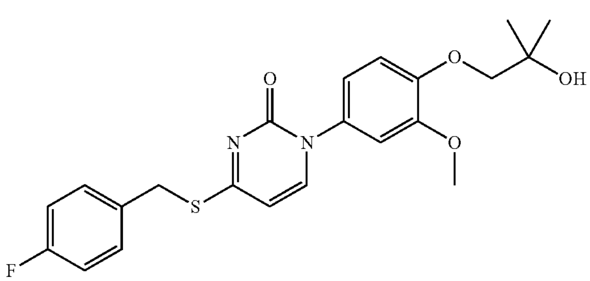 | #2 | #5 0.88 min | 431 | $^1$H NMR (400 MHz, Chloroform-D) δ ppm 7.34-7.46 (3H, m), 6.90-7.06 (4H, m), 6.86 (1H, dd, J = 8.53, 2.51 Hz), 6.24 (1H, d, J = 7.03 Hz), 4.50 (2H, s), 3.87 (3H, s), 3.85 (2H, s), 1.36 (6H, s). |

TABLE A-continued

| Ex. No. | Structure | Experimental Procedure Used | HPLC Method ($t_R$ Min) | MS (M + H) | NMR Data |
|---|---|---|---|---|---|
| A-4 | (3,4-dichlorobenzyl thio pyrimidinone with 3-methoxy-4-(2-hydroxy-2-methylpropoxy)phenyl) | #2 | #5 0.98 min | 481 | $^1$H NMR (400 MHz, Chloroform-D) δ ppm 7.51 (1H, d, J = 2.26 Hz), 7.42 (1H, d, J = 6.78 Hz), 7.39 (1H, d, J = 8.28 Hz), 7.30 (1H, dd, J = 8.28, 2.01 Hz), 6.96 (1H, d, J = 8.53 Hz), 6.94 (1H, d, J = 2.51 Hz), 6.86 (1H, dd, J = 8.28, 2.51 Hz), 6.25 (1H, d, J = 7.03 Hz), 4.47 (2H, s), 3.87 (3H, s), 3.85 (2H, s), 1.36 (6H, s). |
| A-5 | (2-chlorobenzyl thio pyrimidinone with 3-methoxy-4-(2-hydroxy-2-methylpropoxy)phenyl) | #2 | #5 0.93 min | 447 | $^1$H NMR (400 MHz, Chloroform-D) δ 7.57-7.71 (1H, m), 7.34-7.44 (2H, m), 7.21-7.25 (2H, m), 6.91-7.02 (2H, m), 6.86 (1H, dd, J = 8.28, 2.26 Hz), 6.23 (1H, d, J = 7.03 Hz), 4.65 (2H, s), 3.87 (3H, s), 3.85 (2H, s), 1.36 (6H, s). |
| A-6 | (4-methylbenzyl thio pyrimidinone with 3-methoxy-4-(2-hydroxy-2-methylpropoxy)phenyl) | #2 | #5 0.92 min | 427 | $^1$H NMR (400 MHz, Chloroform-D) δ 7.38 (1H, d, J = 7.03 Hz), 7.31 (2H, d, J = 8.03 Hz), 7.14 (2H, d, J = 7.78 Hz), 6.90-7.05 (2H, m), 6.86 (1H, dd, J = 8.53, 2.51 Hz), 6.23 (1H, d, J = 6.78 Hz), 4.50 (2H, s), 3.86 (3H, s), 3.85 (2H, s), 2.34 (3H, s), 1.35 (6H, s). |
| A-7 | (3-chloro-4-fluorobenzyl thio pyrimidinone with 3-methoxy-4-(2-hydroxy-2-methylpropoxy)phenyl) | #2 | #5 0.94 min | 465 | $^1$H NMR (400 MHz, Chloroform-D) δ 7.46 (1H, dd, J = 6.90, 2.13 Hz), 7.42 (1H, d, J = 7.03 Hz), 7.32 (1H, ddd, J = 8.53, 4.52, 2.26 Hz), 7.08 (1H, t, J = 8.66 Hz), 6.96 (1H, d, J = 8.53 Hz), 6.94 (1H, d, J = 2.26 Hz), 6.87 (1H, dd, J = 8.53, 2.51 Hz), 6.25 (1H, d, J = 7.03 Hz), 4.47 (2H, s), 3.87 (3H, s), 3.85 (2H, s), 1.36 (6H, s). |

TABLE A-continued

| Ex. No. | Structure | Experimental Procedure Used | HPLC Method ($t_R$ Min) | MS (M + H) | NMR Data |
|---|---|---|---|---|---|
| A-8 | 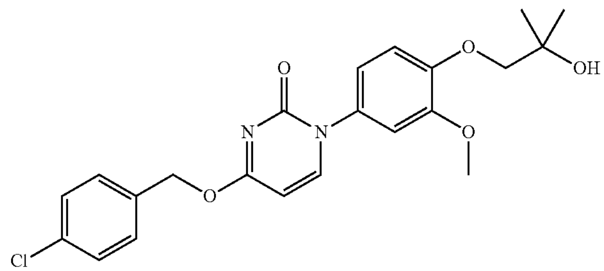 | #2 | #5 0.90 min | 431 | $^1$H NMR (400 MHz, chloroform-D) δ 7.53 (1H, d, J = 7.03 Hz), 7.40 (2H, d, J = 8.53 Hz), 7.37 (2H, d, J = 8.78 Hz), 6.96 (1H, d, J = 8.53 Hz), 6.91 (1H, d, J = 2.26 Hz), 6.85 (1H, dd, J = 8.53, 2.51 Hz), 6.00 (1H, d, J = 7.03 Hz), 5.45 (2H, s), 3.86 (3H, s), 3.85 (2H, s), 1.35 (6H, s). |
| A-9 | 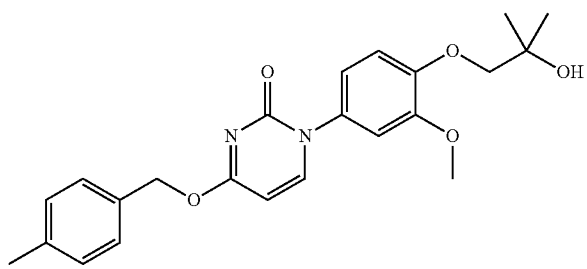 | #3 | #5 0.89 min | 411 | $^1$H NMR (400 MHz, Chloroform-D) δ 7.51 (1H, d, J = 7.28 Hz), 7.35 (2H, d, J = 7.78 Hz), 7.21 (2H, d, J = 8.03 Hz), 6.96 (1H, d, J = 8.53 Hz), 6.91 (1H, d, J = 2.51 Hz), 6.86 (1H, dd, J = 8.53, 2.51 Hz), 5.99 (1H, d, J = 7.28 Hz), 5.43 (2H, s), 3.86 (3H, s), 3.85 (2H, s), 2.38 (3H, s), 1.35 (6H, s). |
| A-10 | 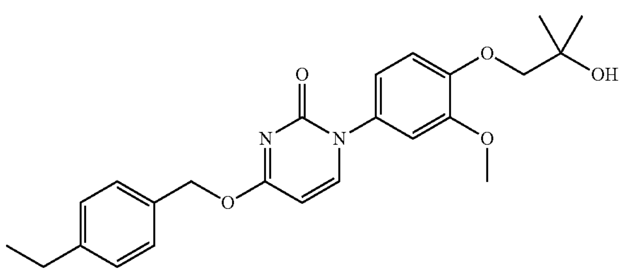 | #3 | #5 0.94 min | 447 (M + Na)$^+$ | $^1$H NMR (400 MHz, Chloroform-D) δ 7.51 (1H, d, J = 7.28 Hz), 7.38 (2H, d, J = 7.78 Hz), 7.24 (2H, d, J = 8.03 Hz), 6.96 (1H, d, J = 8.53 Hz), 6.92 (1H, d, J = 2.51 Hz), 6.86 (1H, dd, J = 8.53, 2.51 Hz), 5.99 (1H, d, J = 7.28 Hz), 5.44 (2H, s), 3.86 (3H, s), 3.85 (2H, s), 2.67 (2H, q, J = 7.53 Hz), 1.35 (6H, s), 1.25 (3H, t, J = 7.65 Hz). |
| A-11 | 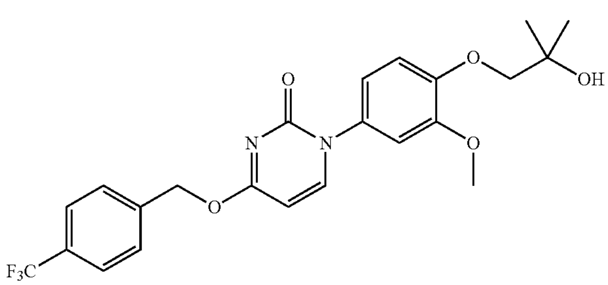 | #3 | #5 0.93 min | 465 | $^1$H NMR (400 MHz, Chloroform-D) δ 7.66 (1H, d, J = 8.03 Hz), 7.51-7.61 (2H, m), 6.96 (1H, d, J = 8.28 Hz), 6.91 (1H, d, J = 2.51 Hz), 6.86 (1H, dd, J = 8.28, 2.51 Hz), 6.04 (1H, d, J = 7.28 Hz), 5.54 (2H, s), 3.86 (3H, s), 3.85 (2H, s), 1.35 (6H, s). |

TABLE A-continued

| Ex. No. | Structure | Experimental Procedure Used | HPLC Method ($t_R$ Min) | MS (M + H) | NMR Data |
|---|---|---|---|---|---|
| A-12 | 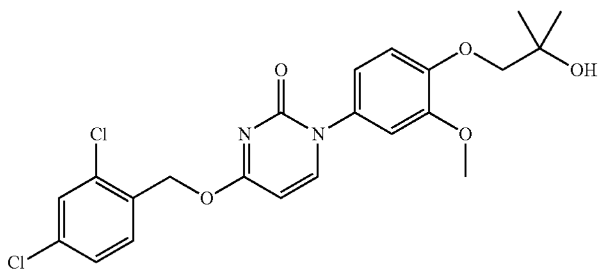 | #3 | #5 0.96 min | 465 | $^1$HNMR(400 MHz, Chloroform-D) δ 7.55 (1H, d, J = 7.03 Hz), 7.48 (1H, d, J = 8.28 Hz), 7.45 (1H, d, J = 2.01 Hz), 7.30 (1H, d, J = 2.01 Hz), 7.28 (1H, d, J = 2.26 Hz), 6.96 (1H, d, J = 8.28 Hz), 6.92 (1H, d, J = 2.51 Hz), 6.86 (1H, dd, J = 8.53, 2.51 Hz), 6.03 (1H, d, J = 7.28 Hz), 5.54 (2H, s), 3.86 (3H, s), 3.85 (2H, s), 1.35 (6H, s). |
| A-13 | 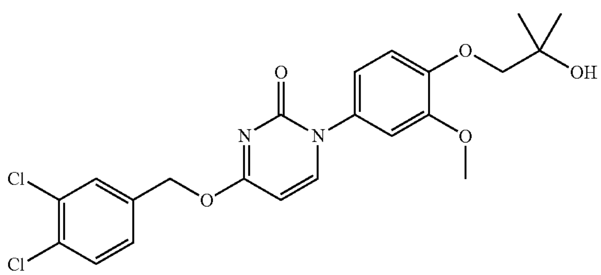 | #3 | #5 0.96 min | 488 (M + Na)$^+$ | $^1$H NMR (400 MHz, Chloroform-D) δ 7.64 (1H, d, J = 1.51 Hz), 7.37-7.39 (2H, m), 7.28 (1H, s), 6.95 (1H, d, J = 9.04 Hz), 6.78-6.86 (2H, m), 5.87 (1H, d, J = 8.03 Hz), 5.09 (2H, s), 3.86 (3H, s), 3.84 (2H, s), 1.35 (6H, s). |
| A-14 | 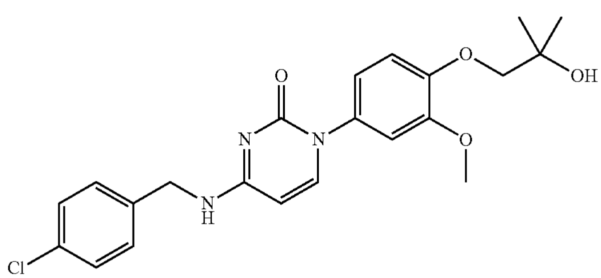 | #1 | #5 0.71 min | 430 | $^1$H NMR (400 MHz, CD$_3$OD) δ 7.54 (1H, dd, J = 7.28, 1.51 Hz), 7.30-7.44 (4H, m), 6.98-7.10 (2H, m), 6.88 (1H, d, J = 8.28 Hz), 5.97 (1H, dd, J = 7.28, 1.51 Hz), 4.63 (2H, s), 3.88 (3H, s), 3.83 (2H, s), 1.33 (6H, s). |
| A-15 | 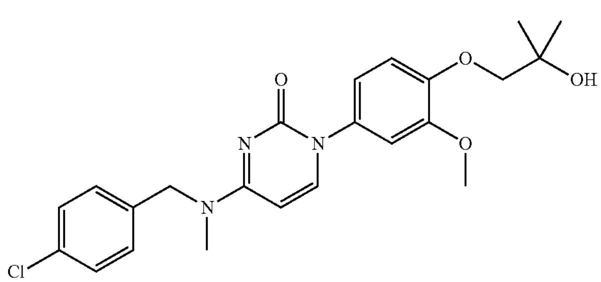 | #1 | #5 0.77 min | 444 | Mixture of conformational isomers |

TABLE A-continued

| Ex. No. | Structure | Experimental Procedure Used | HPLC Method ($t_R$ Min) | MS (M + H) | NMR Data |
|---|---|---|---|---|---|
| A-16 | 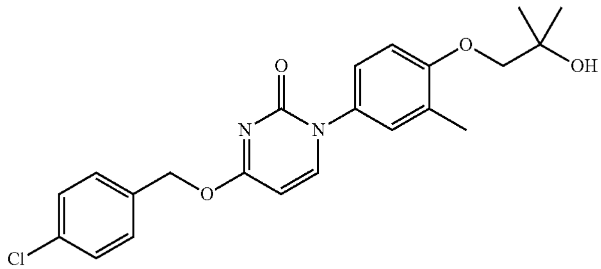 | #3 | #5 0.96 min | 415 | $^1$H NMR (500 MHz, CD$_3$OD) δ 7.86 (1H, d, J = 7.15 Hz), 7.48 (2H, d, J = 8.25 Hz), 7.39 (2H, d, J = 8.25 Hz), 7.05-7.37 (2H, m), 6.99 (1H, d, J = 8.52 Hz), 6.18 (1H, d, J = 7.15 Hz), 5.43 (2H, s), 3.84 (2H, s), 2.30 (3H, s), 1.36 (6H, s). |
| A-17 | 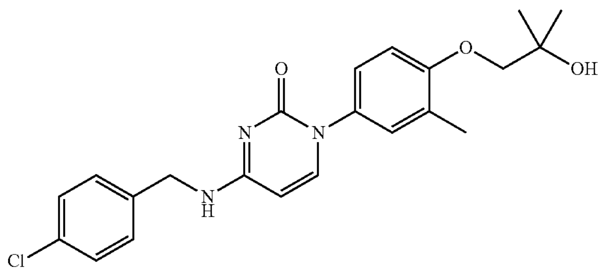 | #1 | #5 0.75 min | 414 | $^1$H NMR (500 MHz, CD$_3$OD) δ 7.49 (1H, dd), 7.36 (2H, d, J = 8.25 Hz), 7.33 (2H, d, J = 8.25 Hz), 7.02-7.22 (2H, m), 6.95 (1H, d, J = 8.52 Hz), 5.95 (1H, dd, J = 7.29, 1.24 Hz), 4.61 (2H, s), 3.82 (2H, s), 2.28 (3H, s), 1.35 (6H, s). |
| A-18 | 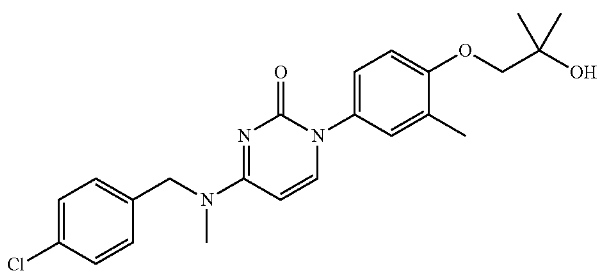 | #1 | #5 0.77 min | 428 | Mixture of conformational isomers |
| A-19 | 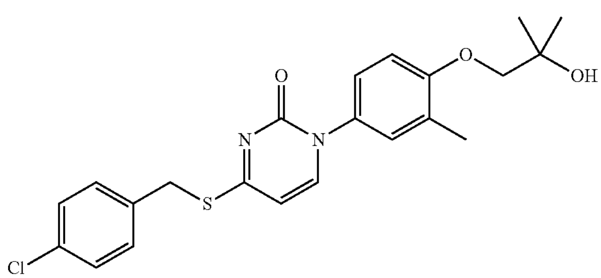 | #1 | #5 0.99 min | 431 | $^1$H NMR (500 MHz, CD$_3$OD) δ 7.72 (1H, d, J = 7.15 Hz), 7.45 (2H, td, J = 8.52 Hz), 7.30 (2H, d, J = 8.52 Hz), 7.06-7.27 (2H, m), 6.99 (1H, d, J = 8.52 Hz), 6.49 (1H, d, J = 6.87 Hz), 4.46 (2H, s), 3.83 (2H, s), 2.29 (3H, s), 1.35 (6H, s). |
| A-20 | 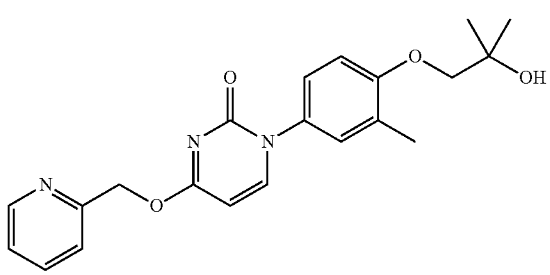 | #1 | #2 1.21 min | 382 | Mixture of conformational isomers |

TABLE A-continued

| Ex. No. | Structure | Experimental Procedure Used | HPLC Method ($t_R$ Min) | MS (M + H) | NMR Data |
|---|---|---|---|---|---|
| A-21 | 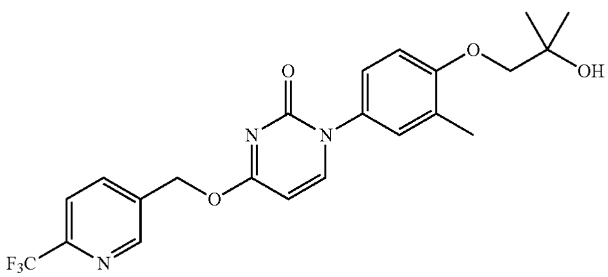 | #1 | #5 0.89 min | 450 | $^1$H NMR (500 MHz, Chloroform-D) δ 8.90 (1H, s), 8.06 (1H, d, J = 7.70 Hz), 7.63 (1H, d, J = 7.70 Hz), 7.29 (1H, s), 7.07-7.11 (2H, m), 6.87 (1H, d, J = 8.25 Hz), 5.88 (1H, d, J = 7.70 Hz), 5.23 (2H, s), 3.83 (2H, s), 2.29 (3H, s), 1.39 (6H, s) |

TABLE B

| Ex. No. | Structure | Experimental Procedure Used | HPLC Method ($t_R$ Min) | MS (M + H) | NMR Data |
|---|---|---|---|---|---|
| B-1 | 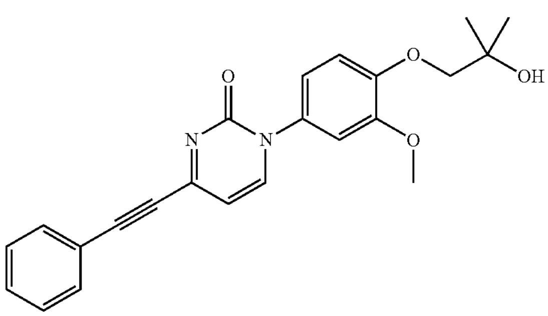 | #4 | #5 0.82 min | 391 | $^1$H NMR (400 MHz, chloroform-D) δ 7.70 (1 H, d, J = 6.78 Hz), 7.51-7.66 (2 H, m), 7.37-7.47 (3 H, m), 6.95-7.12 (2 H, m), 6.90 (1 H, dd, J = 8.53, 2.51 Hz), 6.54 (1 H, d, J = 6.78 Hz), 3.88 (3 H, s), 3.85 (2 H, s), 1.36 (6 H, s). |

TABLE B-continued

| Ex. No. | Structure | Experimental Procedure Used | HPLC Method ($t_R$ Min) | MS (M + H) | NMR Data |
|---|---|---|---|---|---|
| B-2 | 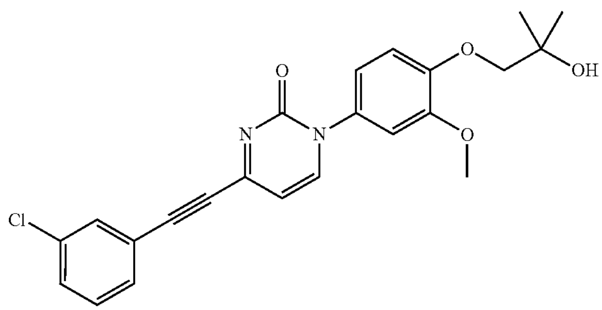 | #4 | #5 0.89 min | 425 | $^1$H NMR (400 MHz, Chloroform-D) δ 7.72 (1 H, d), 7.58-7.63 (1 H, m), 7.51 (1 H, d, J = 7.53 Hz), 7.41-7.47 (1 H, m), 7.36 (1 H, d, J = 7.78 Hz), 6.99 (1 H, s), 6.97 (1 H, d, J = 6.53 Hz), 6.90 (1 H, dd, J = 8.53, 2.51 Hz), 6.53 (1 H, d, J = 6.78 Hz), 3.88 (3 H, s), 3.86 (2 H, s), 1.36 (6 H, s). |
| B-3 | 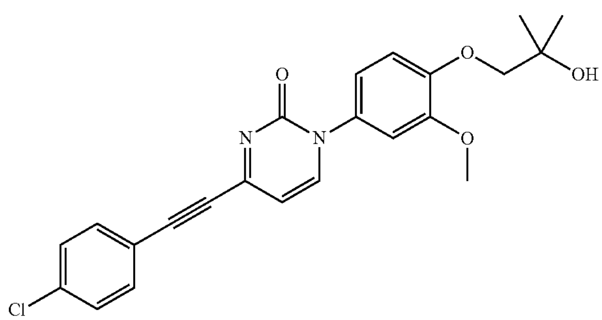 | #4 | #5 0.89 min | 425 | $^1$H NMR (400 MHz, Chloroform-D) δ 7.71 (1 H, d, J = 6.78 Hz), 7.56 (2 H, d, J = 8.53 Hz), 7.39 (2 H, d, J = 8.53 Hz), 6.98 (1 H, s), 6.97 (1 H, d, J = 6.78 Hz), 6.89 (1 H, dd, J = 8.53, 2.51 Hz), 6.52 (1 H, d, J = 6.78 Hz), 3.88 (3 H, s), 3.85 (2 H, s), 1.36 (6 H, s). |
| B-4 | 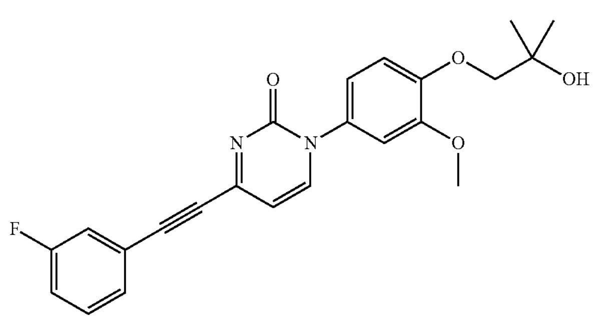 | #4 | #5 0.84 min | 409 | $^1$H NMR (400 MHz, Chloroform-D) δ 7.72 (1 H, d, J = 6.78 Hz), 7.34-7.45 (2 H, m), 7.31 (1 H, d, J = 9.03 Hz), 7.13-7.22 (1 H, m), 6.98 (1 H, s), 6.97 (1 H, d, J = 6.78 Hz), 6.89 (1 H, dd, J = 8.53, 2.26 Hz), 6.54 (1 H, d, J = 6.78 Hz), 3.88 (3 H, s), 3.85 (2 H, s), 1.36 (6 H, s). |

TABLE B-continued

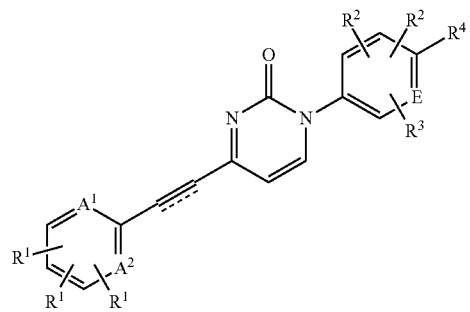

| Ex. No. | Structure | Experimental Procedure Used | HPLC Method ($t_R$ Min) | MS (M + H) | NMR Data |
|---|---|---|---|---|---|
| B-5 | 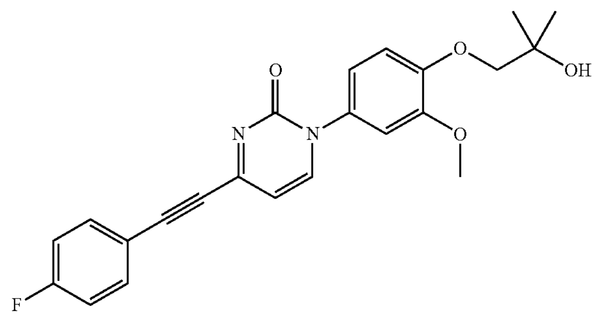 | # 4 | # 5 0.83 min | 409 | $^1$H NMR (400 MHz, Chloroform-D) δ 7.70 (1 H, d, J = 6.78 Hz), 7.59-7.67 (2 H, m), 7.11 (2 H, t, J = 8.66 Hz), 6.98 (1 H, s), 6.97 (1 H, d, J = 7.03 Hz), 6.89 (1 H, dd, J = 8.53, 2.26 Hz), 6.52 (1 H, d, J = 6.78 Hz), 3.88 (3 H, s), 3.85 (2 H, s), 1.36 (6 H, s). |
| B-6 | 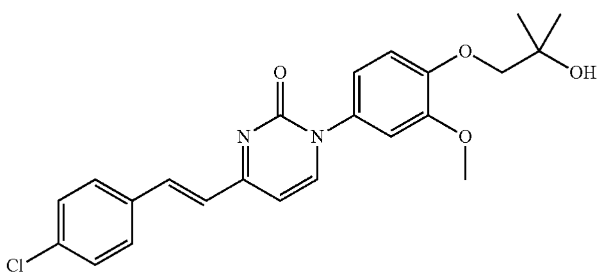 | # 5 | # 5 0.84 min | 427 | $^1$H NMR (400 MHz, chloroform-D) δ 7.91 (1 H, d, J = 16.06 Hz), 7.69 (1 H, d, J = 6.78 Hz), 7.54 (2 H, d, J = 8.28 Hz), 7.39 (2 H, d, J = 8.53 Hz), 6.87-7.01 (4 H, m), 6.49 (1 H, d, J = 6.78 Hz), 3.87 (3 H, s), 3.85 (2 H, s), 1.36 (6 H, s). |

TABLE C

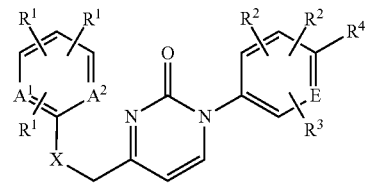

| Ex. No. | Structure | Experimental Procedure Used | HPLC Method ($t_R$ Min) | MS (M + H) | NMR Data |
|---|---|---|---|---|---|
| C-1 | 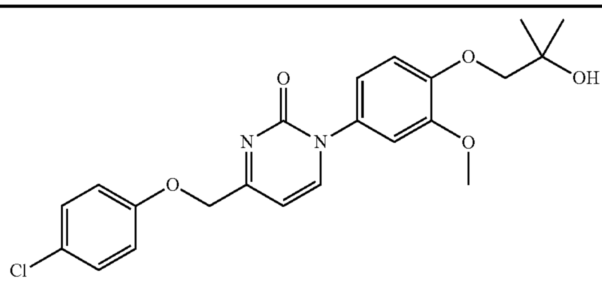 | # 6 | # 5 0.81 min | 431 | $^1$H NMR (400 MHz, Chloroform-D) δ 7.73 (1 H, d, J = 6.78 Hz), 7.28-7.31 (2 H, m), 6.94-7.03 (2 H, m), 6.86-6.94 (3 H, m), 6.66 (1 H, d, J = 7.03 Hz), 5.02 (2 H, s), 3.87 (3 H, s), 3.86 (2 H, s), 1.36 (6 H, s). |

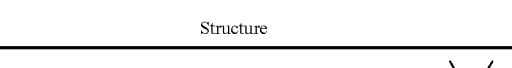

TABLE C-continued

| Ex. No. | Structure | Experimental Procedure Used | HPLC Method ($t_R$ Min) | MS (M + H) | NMR Data |
|---|---|---|---|---|---|
| C-2 | 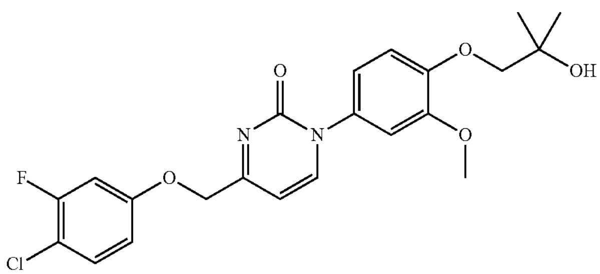 | # 6 | # 5 0.88 min | 449 | $^1$H NMR (500 MHz, Chloroform-D) δ 7.72 (1 H, d, J = 6.60 Hz), 7.29 (1 H, t), 6.91-6.97 (2 H, m), 6.84 -6.88 (1 H, m), 6.77 (1 H, dd), 6.68-6.72 (1 H, m), 6.60 (1 H, d, J = 7.15 Hz), 4.98 (2 H, s), 3.84 (3 H, s), 3.83 (2 H, s), 1.33 (6 H, s) |
| C-3 | 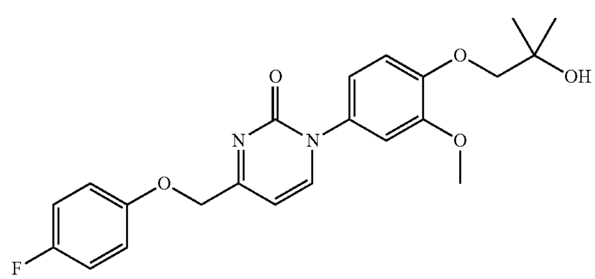 | # 6 | # 5 0.81 min | 415 | $^1$H NMR (400 MHz, Chloroform-D) δ 7.74 (1 H, d, J = 6.78 Hz), 6.97-7.05 (2 H, m), 6.86-6.97 (5 H, m), 6.68 (1 H, d, J = 6.78 Hz), 5.00 (2 H, s), 3.87 (3 H, s), 3.85 (2 H, s), 1.36 (6 H, s) |
| C-4 | 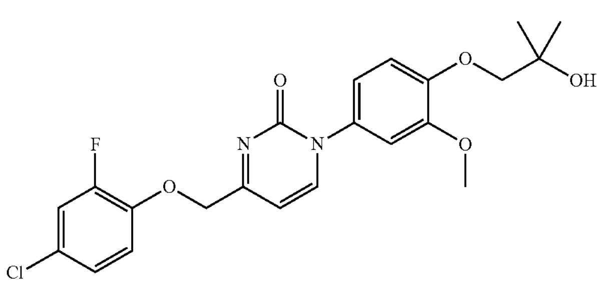 | # 6 | # 5 0.88 min | 449 | $^1$H NMR (400 MHz, Chloroform-D) δ 7.77 (1 H, d, J = 6.78 Hz), 7.17 (1 H, dd), 6.94-7.00 (3 H, m), 6.88-6.93 (2 H, m), 6.75 (1 H, d, J = 6.78 Hz), 5.07 (2 H, s), 3.87 (3 H, s), 3.86 (2 H, s), 1.36 (6 H, s) |
| C-5 | 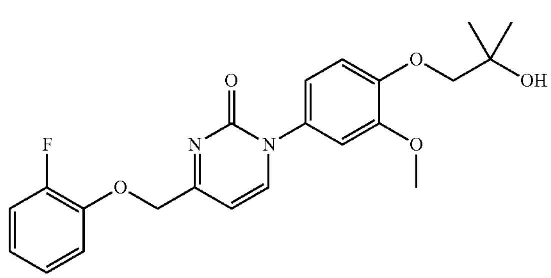 | # 6 | # 5 0.81 min | 415 | $^1$H NMR (400 MHz, CD$_3$OD) δ 8.18 (1 H, d), 7.07-7.21 (5 H, m), 6.96-7.03 (2 H, m), 6.90 (1 H, d), 5.12 (2 H, s), 3.88 (3 H, s), 3.84 (2 H, s), 1.33 (6 H, s) |

TABLE C-continued

| Ex. No. | Structure | Experimental Procedure Used | HPLC Method ($t_R$ Min) | MS (M + H) | NMR Data |
|---|---|---|---|---|---|
| C-6 | (2,4-dichlorophenoxymethyl-pyrimidinone with 4-(2-hydroxy-2-methylpropoxy)-3-methoxyphenyl) | # 6 | # 5 0.93 min | 465 | $^1$H NMR (400 MHz, Chloroform-D) δ 7.78 (1 H, d, J = 6.78 Hz), 7.44 (1 H, d, J = 2.51 Hz), 7.23 (1 H, dd, J = 8.78, 2.51 Hz), 6.94-7.00 (2 H, m), 6.88-6.93 (2 H, m), 6.81 (1 H, d, J = 6.78 Hz), 5.07 (2 H, s), 3.88 (3 H, s), 3.86 (2 H, s), 1.36 (6 H, s) |

TABLE D

| Ex. No. | Structure | Experimental Procedure Used$^a$ | HPLC Method ($t_R$ Min) | MS (M + H) | NMR Data |
|---|---|---|---|---|---|
| D-1 | (5-(phenylethynyl)pyridazinone with 4-(2-hydroxy-2-methylpropoxy)-3-methoxyphenyl) | # 4 | # 5 0.95 min | 391 | $^1$H NMR (400 MHz, Chloroform-D) δ 7.91 (1 H, d, J = 2.01 Hz), 7.59 (2 H, dd, J = 7.91, 1.63 Hz), 7.39-7.48 (3 H, m), 7.15-7.21 (2 H, m), 7.12 (1 H, d, J = 2.01 Hz), 6.99 (1 H, d, J = 9.29 Hz), 3.89 (3 H, s), 3.88 (2 H, s), 1.36 (6 H, s) |

TABLE D-continued

| Ex. No. | Structure | Experimental Procedure Used[a] | HPLC Method (t_R Min) | MS (M + H) | NMR Data |
|---|---|---|---|---|---|
| D-2 | 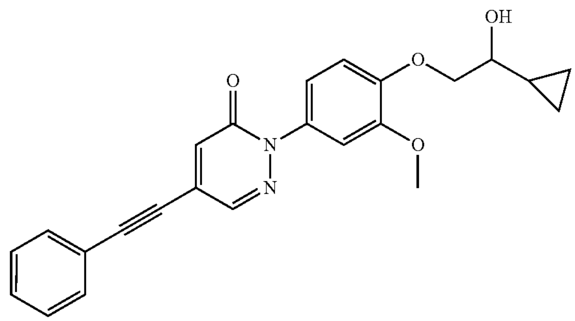 | #4 | #5 0.96 min | 403 | $^1$H NMR (400 MHz, Chloroform-D) δ 7.91 (1 H, d, J = 2.01 Hz), 7.59 (2 H, d), 7.37-7.52 (2 H, m), 7.15-7.22 (2 H, m), 7.12 (1 H, d, J = 2.01 Hz), 7.03 (1 H, d, J = 8.53 Hz), 4.22 (1 H, dd, J = 9.91, 2.89 Hz), 3.98-4.08 (1 H, m), 3.90 (3 H, s), 3.21-3.41 (1 H, m), 2.74 (1 H, d, J = 2.76 Hz), 0.92-1.04 (1 H, m), 0.51-0.69 (2 H, m), 0.39-0.51 (1 H, m), 0.21-0.37 (1 H, m) |
| D-3 | 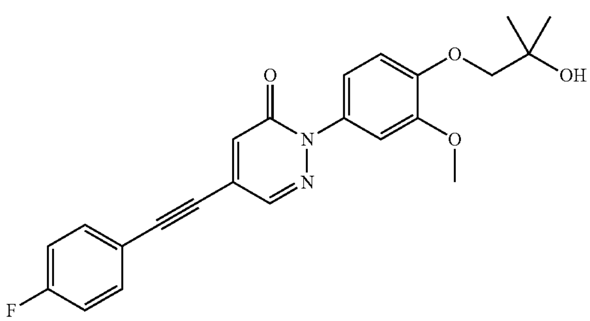 | #4 | #5 0.96 min | 409 | $^1$H NMR (400 MHz, Chloroform-D) δ 7.90 (1 H, d, J = 2.01 Hz), 7.59 (2 H, dd, J = 8.78, 5.27 Hz), 7.08-7.20 (5 H, m), 6.99 (1 H, d, J = 9.29 Hz), 3.89 (3 H, s), 3.88 (2 H, s), 1.36 (6 H, s) |
| D-4 | 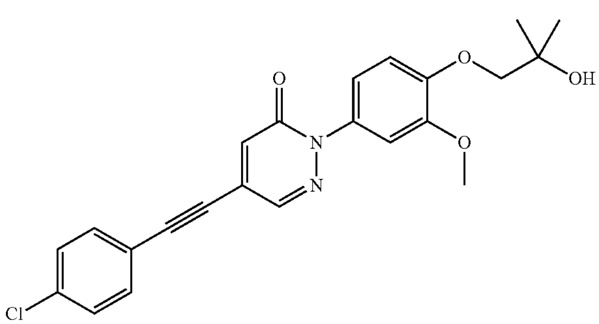 | #4 | #5 1.02 min | 425 | $^1$H NMR (400 MHz, Chloroform-D) δ 7.89 (1 H, d, J = 1.76 Hz), 7.52 (2 H, d, J = 8.28 Hz), 7.40 (2 H, d, J = 8.53 Hz), 7.09-7.21 (3 H, m), 6.98 (1 H, d, J = 9.03 Hz), 3.89 (3 H, s), 3.87 (2 H, s), 1.36 (6 H, s) |

TABLE D-continued

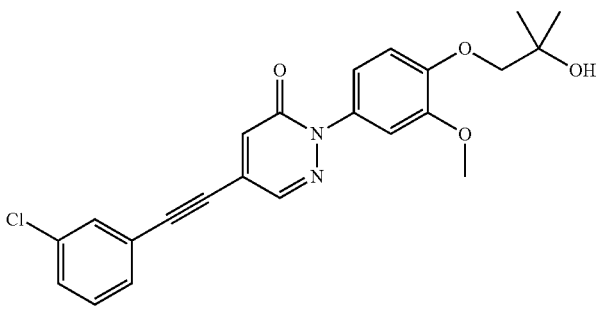

| Ex. No. | Structure | Experimental Procedure Used[a] | HPLC Method ($t_R$ Min) | MS (M + H) | NMR Data |
|---|---|---|---|---|---|
| D-5 | 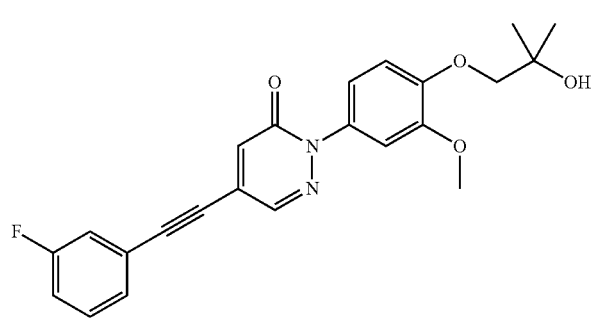 | # 4 | # 5 1.02 min | 425 | $^1$H NMR (400 MHz, Chloroform-D) δ 7.90 (1 H, d, J = 2.01 Hz), 7.59 (1 H, s), 7.42-7.50 (2 H, m), 7.33-7.39 (1 H, m), 7.15-7.21 (2 H, m), 7.13 (1 H, d, J = 2.01 Hz), 6.96-7.02 (1 H, m), 3.89 (3 H, s), 3.88 (2 H, s), 1.36 (6 H, s) |
| D-6 | 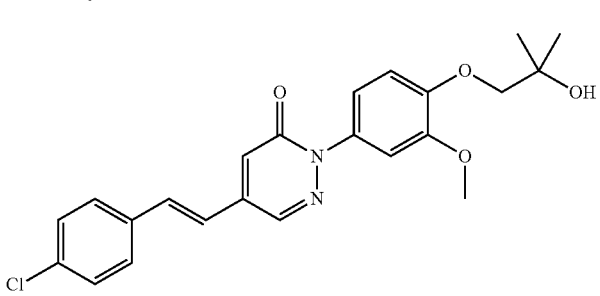 | # 4 | 0.96 min | 409 | $^1$H NMR (400 MHz, Chloroform-D) ppm 7.90 (1 H, d, J = 2.01 Hz), 7.36-7.43 (2 H, m), 7.28-7.32 (1 H, m), 7.15-7.21 (3 H, m), 7.13 (1 H, d, J = 2.26 Hz), 6.99 (1 H, d, J = 9.03 Hz), 3.89 (3 H, s), 3.88 (2 H, s), 1.36 (6 H, s) |
| D-7 | 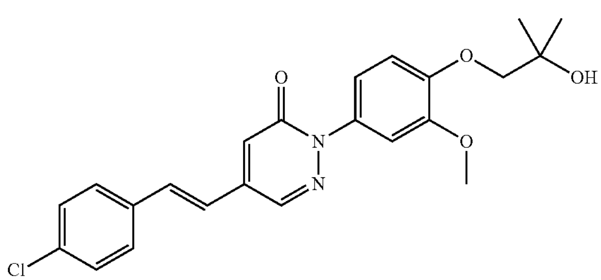 | # 5 | # 5 0.98 min | 427 | $^1$H NMR (400 MHz, Chloroform-D) δ 8.12 (1 H, d, J = 2.01 Hz), 7.50 (2 H, d, J = 8.53 Hz), 7.40 (2 H, d, J = 8.53 Hz), 7.26 (1 H, d, J = 16.56 Hz), 7.17 (1 H, dq, J = 4.55, 2.33 Hz), 6.99 (1 H, d, J = 9.29 Hz), 6.95 (1 H, d, J = 2.26 Hz), 6.88 (1 H, d, J = 16.56 Hz), 3.89 (3 H, s), 3.87 (2 H, s), 1.36 (6 H, s). |
| D-8 | 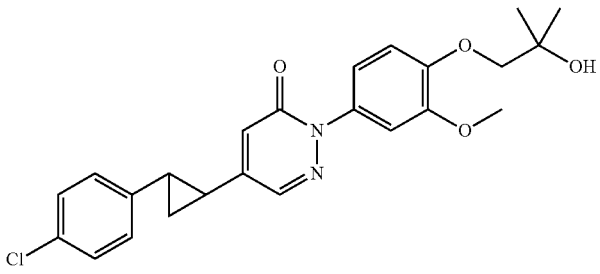 | # 15 | # 5 0.98 | 441 | $^1$H NMR (400 MHz, CDCl3-d) δ ppm 7.78 (1 H, d, J = 2.26 Hz), 7.30 (2 H, d, J = 8.53 Hz), 7.05-7.16 (4 H, m), 6.97 (1 H, d, J = 9.03 Hz), 6.72 (1 H, d, J = 2.26 Hz), 3.87 (5 H, d, J = 2.26 Hz), 2.33 (1 H, ddd, J = 8.91, 6.15, 4.52 Hz), 1.91-2.08 (1 H, m), 1.53-1.71 (2 H, m), 1.35 (6 H, s). |

[a]4-iodo-6-oxo-pyridazine was converted to indicated following the method specified

TABLE E

| Ex. No. | Structure | Experimental Procedure Used | HPLC Method ($t_R$ Min) | MS (M + H) | NMR Data |
|---|---|---|---|---|---|
| E-1 | 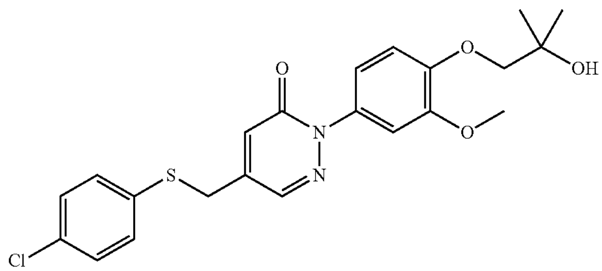 | #7 | #5 0.95 min | 447 | $^1$H NMR (400 MHz, Chloroform-D) δ ppm 7.85 (1 H, d, J = 2.26 Hz), 7.30 (4 H, s), 7.09-7.14 (2 H, m), 6.96 (1 H, d, J = 9.29 Hz), 6.68-6.72 (1 H, m), 3.87 (7 H, t, J = 5.40 Hz), 1.35 (6 H, s) |
| E-2 | 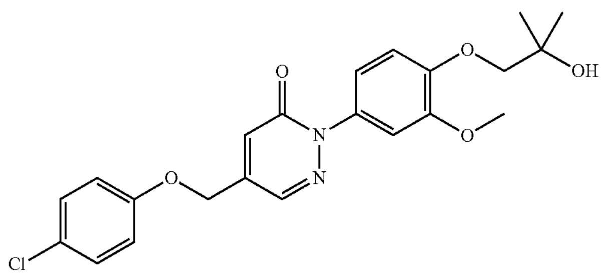 | #8 | #5 0.93 min | 431 | 1H NMR (500 MHz, Chloroform-D) δ ppm 7.94 (1 H, d, J = 1.92 Hz), 7.30 (2 H, d), 7.12-7.17 (2 H, m), 7.09 (1 H, br. s.), 6.98 (1 H, d, J = 8.25 Hz), 6.91 (2 H, d), 4.97 (2 H, s), 3.82-3.92 (5 H, m), 1.35 (6 H, s) |
| E-3 | 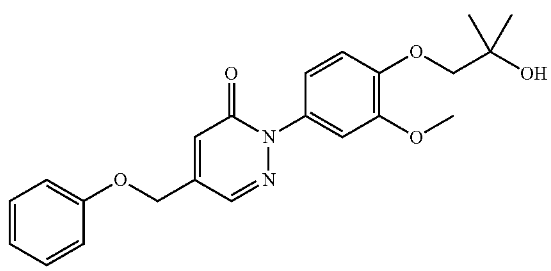 | #8 | #3 3.07 min | 397 | 1H NMR (400 MHz, Chloroform-D) δ ppm 7.96 (1 H, d, J = 2.01 Hz), 7.34 (2 H, t, J = 8.03 Hz), 7.09-7.18 (3 H, m), 6.94-7.08 (4 H, m), 5.01 (2 H, s), 3.79-3.94 (5 H, m), 1.35 (6 H, s) |
| E-4 | 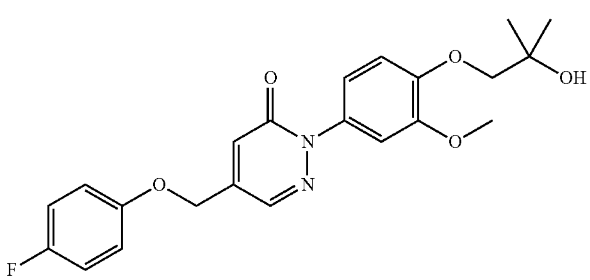 | #8 | #3 3.06 Min | 415 | 1H NMR (400 MHz, Chloroform-D) δ ppm 7.94 (1 H, d, J = 2.01 Hz), 6.84-7.21 (8 H, m), 4.96 (2 H, s), 3.76-3.98 (5 H, m), 1.35 (6 H, s) |

TABLE F

| Ex. No. | Structure | Experimental Procedure Used | HPLC Method ($t_R$ Min) | MS (M + H) | NMR Data |
|---|---|---|---|---|---|
| F-1 | 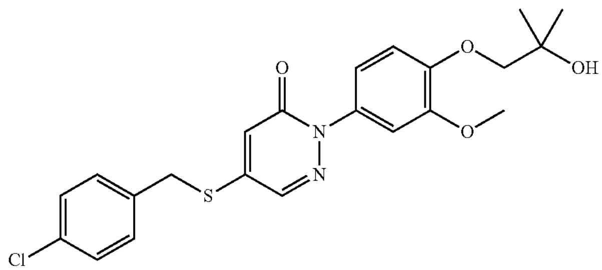 | #9 | #3 4.14 min | 447 | $^1$H NMR (500 MHz, Chloroform-D) δ ppm 7.65 (1 H, d, J = 2.20 Hz), 7.35 (4 H, s), 7.07-7.13 (2 H, m), 6.96 (1 H, d, J = 8.80 Hz), 6.66 (1 H, d, J = 2.20 Hz), 4.15 (2 H, s), 3.81-3.91 (5 H, m), 1.35 (6 H, s) |
| F-2 | 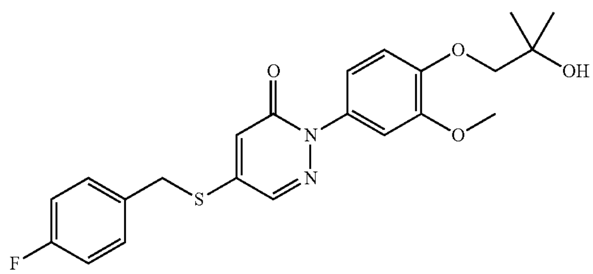 | #9 | #5 0.93 min | 431 | $^1$H NMR (400 MHz, Chloroform-D) δ ppm 7.65 (1 H, d, J = 2.26 Hz), 7.39 (2 H, dd, J = 8.66, 5.14 Hz), 7.02-7.15 (4 H, m), 6.95 (1 H, d, J = 9.03 Hz), 6.68 (1 H, d, J = 2.26 Hz), 4.16 (2 H, s), 3.79-3.92 (5 H, m), 1.35 (6 H, s) |
| F-3 | 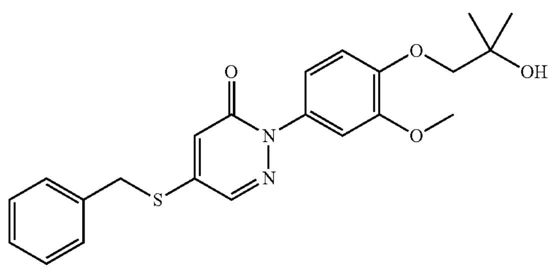 | #9 | #5 0.92 min | 413 | $^1$H NMR (400 MHz, Chloroform-D) δ ppm 7.65 (1 H, d, J = 2.26 Hz), 7.29-7.45 (5 H, m), 7.06-7.14 (2 H, m), 6.96 (1 H, d, J = 9.03 Hz), 6.70 (1 H, d, J = 2.51 Hz), 4.19 (2 H, s), 3.79-3.91 (5 H, m), 1.34 (6 H, s) |
| F-4 | 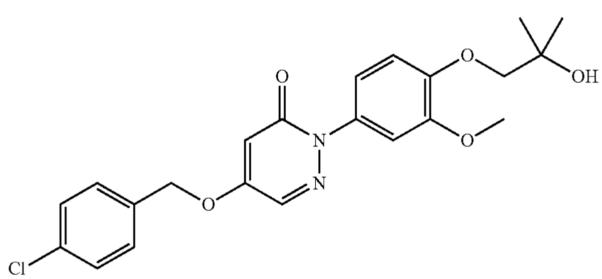 | #9 | #5 0.94; | 431 | $^1$H NMR (400 MHz, Chloroform-d) δ ppm 7.75 (1 H, d, J = 2.86 Hz), 7.32-7.45 (4 H, m), 7.03-7.12 (2 H, m), 6.96 (1 H, d, J = 9.23 Hz), 6.31 (1 H, d, J = 2.86 Hz), 5.04 (2 H, s), 3.79-3.93 (5 H, m), 1.35 (6 H, s) |
| F-5 | 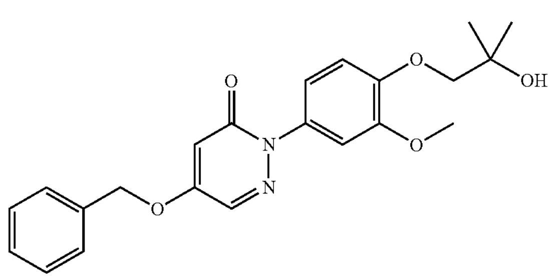 | #8 | #5 0.88 min | 397 | $^1$H NMR (400 MHz, Chloroform-d) δ ppm 7.80 (1 H, d, J = 2.86 Hz), 7.36-7.47 (5 H, m), 7.03-7.10 (2 H, m), 6.93-6.99 (1 H, m), 6.46 (1 H, d, J = 2.86 Hz), 5.09 (2 H, s), 3.78-3.92 (5 H, m), 1.35 (6 H, s) |

TABLE F-continued

| Ex. No. | Structure | Experimental Procedure Used | HPLC Method ($t_R$ Min) | MS (M + H) | NMR Data |
|---|---|---|---|---|---|
| F-6 | 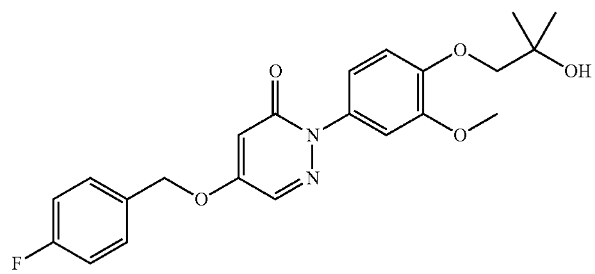 | # 8 | # 5 0.89 min | 415 | $^1$H NMR (400 MHz, Chloroform-d) δ ppm 7.75 (1 H, d, J = 2.64 Hz), 7.35-7.45 (2 H, m), 7.04-7.17 (4 H, m), 6.96 (1 H, d, J = 9.23 Hz), 6.35 (1 H, d, J = 2.86 Hz), 5.03 (2 H, s), 3.80-3.92 (5 H, m), 1.35 (6 H, s) |
| F-7 | 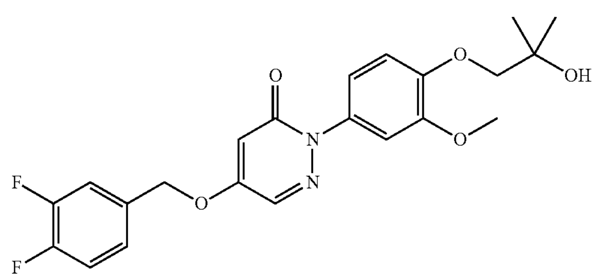 | # 8 | # 5 0.92 min | 433 | $^1$H NMR (400 MHz, Chloroform-d) δ ppm 7.80 (1 H, d, J = 2.64 Hz), 7.29-7.42 (1 H, m), 7.16-7.29 (2 H, m), 7.03 (1 H, s), 6.90-6.99 (2 H, m), 6.34 (1 H, d, J = 2.86 Hz), 5.07 (2 H, s), 3.68-3.83 (5 H, m), 1.23 (6 H, s) |
| F-8 | 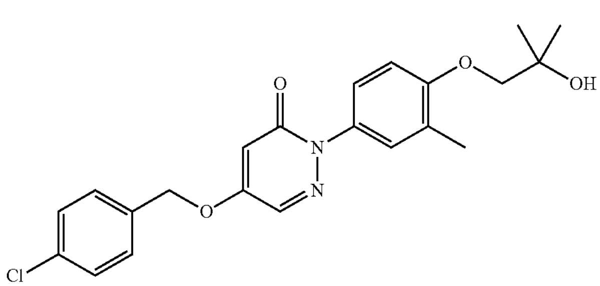 | # 8 | # 5 0.94 min | 431 | $^1$H NMR (400 MHz, Chloroform-d) δ ppm 7.75 (1 H, d, J = 2.86 Hz), 7.32-7.46 (4 H, m), 7.04-7.12 (2 H, m), 6.96 (1 H, d, J = 9.23 Hz), 6.31 (1 H, d, J = 2.86 Hz), 5.04 (2 H, s), 3.78-3.92 (5 H, m), 1.35 (6 H, s) |

TABLE G

| Ex. No. | Structure | Experimental Procedure Used | HPLC Method ($t_R$ Min) | MS (M + H) | NMR Data |
|---|---|---|---|---|---|
| G-1 | 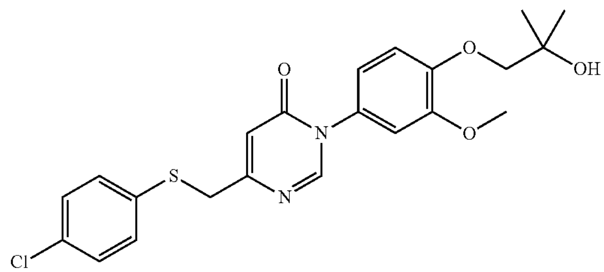 | #10 | #5 0.92 min | 447 | $^1$H NMR (500 MHz, Chloroform-D) δ ppm 8.14 (1 H, br. s.), 7.27-7.36 (4 H, m), 6.99 (1 H, d, J = 8.25 Hz), 6.79-6.88 (2 H, m), 6.45 (1 H, s), 3.96 (2 H, s), 3.82-3.90 (5 H, m), 1.36 (6 H, s) |
| G-2 | 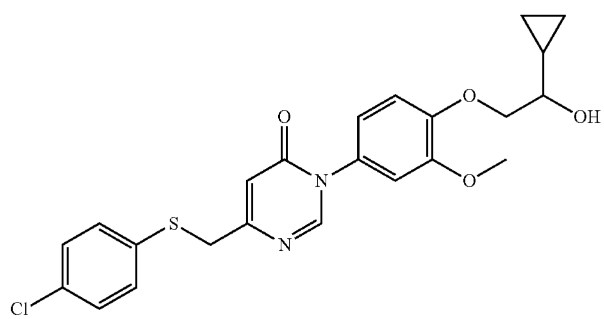 | #16 | #5 0.97 min | 459 | $^1$H NMR (400 MHz, Chloroform-D) δ ppm 8.14 (1 H, s), 7.26-7.40 (4 H, m), 7.03 (1 H, d), 6.80-6.91 (2 H, m), 6.45 (1 H, s), 4.20 (1 H, dd, J = 9.54, 2.76 Hz), 4.03 (1 H, t, J = 8.91 Hz), 3.96 (2 H, s), 3.87 (3 H, s), 3.36 (1 H, td, J = 8.34, 2.64 Hz), 0.91-1.06 (1 H, m), 0.51-0.67 (2 H, m), 0.40-0.50 (1 H, m), 0.26-0.37 (1 H, m) |
| G-3 | 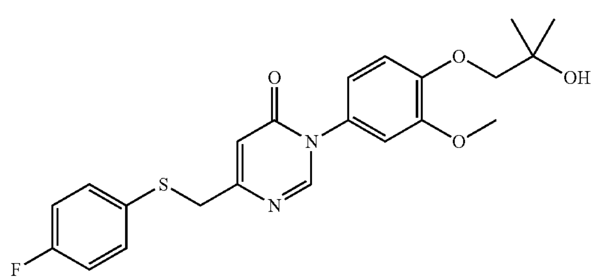 | #10 | #5 0.87 min | 431 | $^1$H NMR (400 MHz, Chloroform-D) δ ppm 8.14 (1 H, s), 7.41 (2 H, dd, J = 8.91, 5.14 Hz), 6.94-7.10 (3 H, m), 6.79-6.90 (2 H, m), 6.37 (1 H, s), 3.81-3.95 (7 H, m), 1.36 (6 H, s) |

TABLE H
| Ex. No. | Structure | Experimental Procedure Used | HPLC Method ($t_R$ Min) | MS (M + H) | NMR Data |
|---|---|---|---|---|---|
| H-1 | 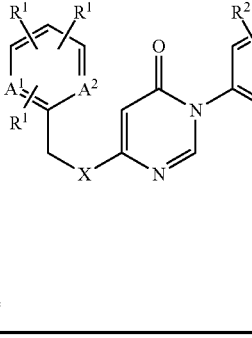 | # 11 | # 5 0.95 min | 425 | $^1$H NMR (400 MHz, Chloroform-d) δδ.04 (1 H, s), 7.38 (4 H, s), 7.00 (1 H, d), 6.79-6.89 (2 H, m), 5.85 (1 H, s), 5.27 (2 H, s), 3.87 (3 H, s), 3.86 (2 H, s), 1.36 (6 H, s). |
| H-2 | 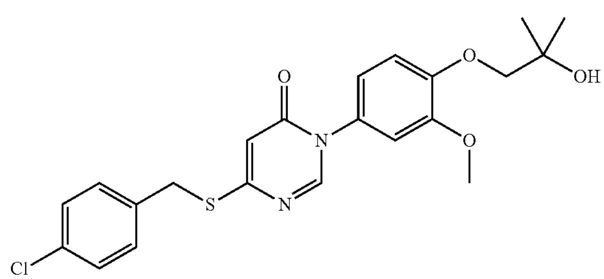 | # 11 | # 5 0.96 min | 447 | $^1$H NMR (400 MHz, Chloroform-d) δ 8.04 (1 H, s), 7.30-7.40 (4 H, m), 6.99 (1 H, d, J = 8.03 Hz), 6.81-6.88 (2 H, m), 6.34 (1 H, s), 4.26 (2 H, s), 3.87 (3 H, s), 3.86 (2 H, s), 1.36 (6 H, s) |
| H-3 | 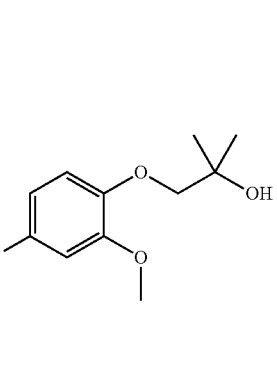 | # 17 | # 5 0.91 min | 431 | $^1$H NMR (400 MHz, Chloroform-d) δ 8.14 (1 H, s), 7.35-7.45 (2 H, m), 6.95-7.09 (3 H, m), 6.80-6.90 (2 H, m), 6.49 (1 H, s), 4.28 (2 H, s), 3.88 (5 H, s), 1.39 (6 H, s) |
| H-4 | 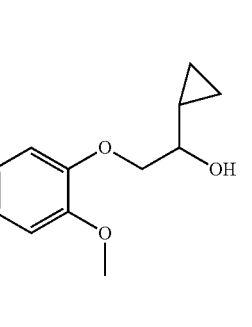 | # 17 | # 5 0.91 min | 425 | $^1$H NMR (400 MHz, Chloroform-d) δ 8.09 (1 H, s), 7.41-7.47 (2 H, m), 7.29-7.40 (3 H, m), 6.99-7.08 (1 H, m), 6.82-6.90 (2 H, m), 6.43 (1 H, s), 4.30 (2 H, s), 4.18-4.25 (1 H, m), 4.05 (1 H, t), 3.87 (3 H, s), 3.34-3.41 (1 H, m), 0.94-1.06 (1 H, m), 0.54-0.68 (2 H, m), 0.43-0.52 (1 H, m), 0.26-0.36 (1 H, m) |

TABLE H-continued

| Ex. No. | Structure | Experimental Procedure Used | HPLC Method ($t_R$ Min) | MS (M + H) | NMR Data |
|---|---|---|---|---|---|
| H-5 | 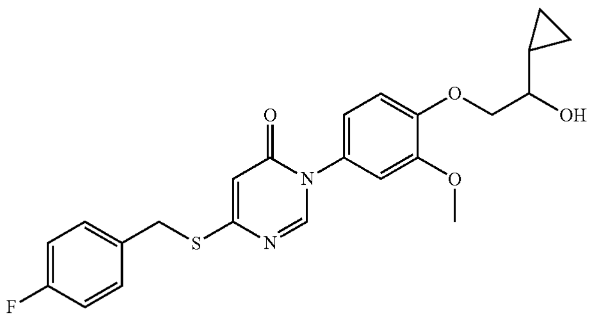 | #17 | #5 0.91 min | 443 | $^1$H NMR (400 MHz, Chloroform-d) δ 8.07 (1 H, s), 7.37-7.44 (2 H, m), 7.00-7.08 (3 H, m), 6.83-6.90 (2 H, m), 6.38 (1 H, s), 4.27 (2 H, s), 4.19-4.24 (1 H, m), 3.99-4.09 (1 H, m), 3.87 (3 H, s), 3.29-3.42 (1 H, m), 0.93-1.04 (1 H, m), 0.51-0.69 (2 H, m), 0.42-0.52 (1 H, m), 0.26-0.36 (1 H, m) |
| H-6 | 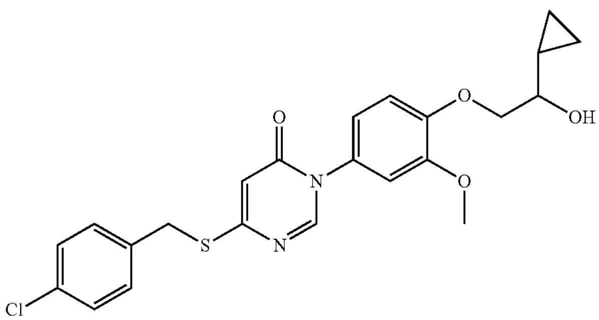 | #17 | #5 0.97 min | 459 | $^1$H NMR (400 MHz, Chloroform-d) δ 8.13 (1 H, s), 7.30-7.39 (4 H, m), 7.03 (1 H, d, J = 9.29 Hz), 6.83-6.91 (2 H, m), 6.49 (1 H, s), 4.27 (2 H, s), 4.22 (1 H, dd, J = 9.79, 2.76 Hz), 4.01-4.10 (1 H, m), 3.86 (3 H, s), 3.33-3.42 (1 H, m), 0.97-1.08 (1 H, m), 0.56-0.68 (2 H, m), 0.42-0.51 (1 H, m), 0.26-0.36 (1 H, m) |
| H-7 | 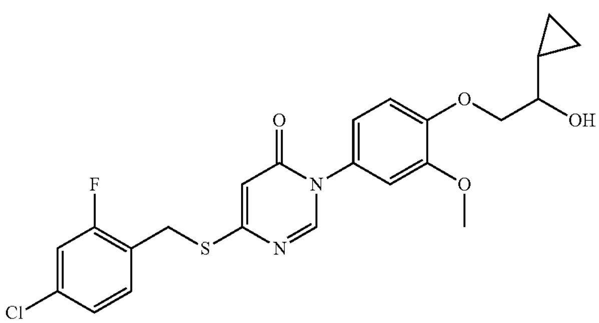 | #11 | #5 0.99 min | 477 | $^1$H NMR (400 MHz, Chloroform-d) δ 8.12 (1 H, s), 7.41 (1 H, t), 7.13 (2 H, d, J = 8.28 Hz), 7.03 (1 H, d, J = 9.03 Hz), 6.80-6.94 (2 H, m), 6.47 (1 H, s), 4.32 (2 H, s), 4.19-4.24 (1 H, m), 4.05 (1 H, t), 3.87 (3 H, s), 3.33-3.44 (1 H, m), 0.95-1.04 (1 H, m), 0.55-0.69 (2 H, m), 0.42-0.52 (1 H, m), 0.27-0.37 (1 H, m) |
| H-8 | 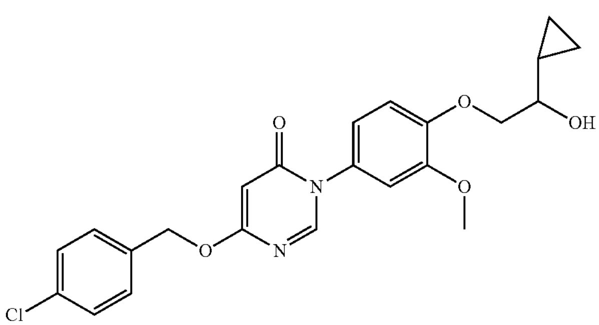 | #11 | #5 0.92 min | 443 | $^1$H NMR (400 MHz, Chloroform-d) δ 8.05 (1 H, s), 7.38 (4 H, s), 7.03 (1 H, d, J = 8.28 Hz), 6.81-6.90 (2 H, m), 5.85 (1 H, s), 5.28 (2 H, s), 4.18-4.25 (1 H, m), 4.00-4.09 (1 H, m), 3.87 (3 H, s), 3.31-3.43 (1 H, m), 0.91-1.04 (1 H, m), 0.52-0.69 (2 H, m), 0.41-0.51 (1 H, m), 0.27-0.39 (1 H, m) |

TABLE J
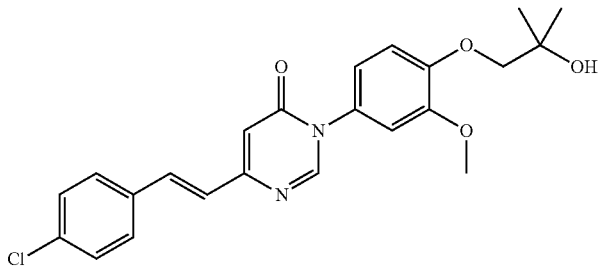
| Ex. No. | Structure | Experimental Procedure Used | HPLC Method ($t_R$ Min) | MS (M + H) | NMR Data |
|---|---|---|---|---|---|
| J-1 | 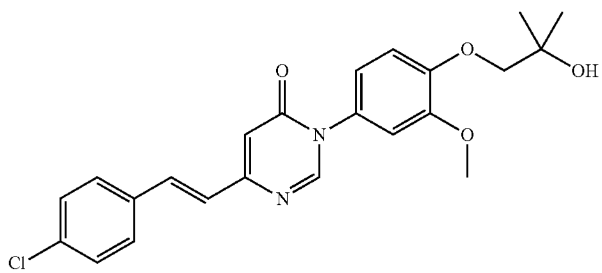 | # 12 | # 5 0.97 min | 427 | $^1$H NMR (400 MHz, Chloroform-d) δ 8.15 (1 H, s), 7.76 (1 H, d, J = 15.56 Hz), 7.53 (2 H, d, J = 8.28 Hz), 7.38 (2 H, d, J = 8.28 Hz), 7.01 (1 H, d, J = 8.03 Hz), 6.82-6.98 (3 H, m), 6.46 (1 H, s), 3.89 (5 H, br. s.), 1.37 (6 H, s). |
| J-2 | 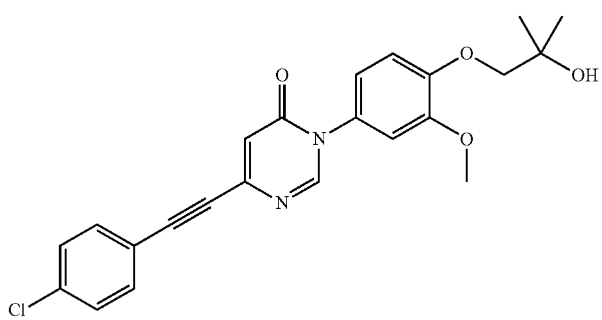 | # 13 | # 5 0.95 min | 425 | $^1$H NMR (400 MHz, Chloroform-d) δ 8.14-8.17 (1 H, m), 7.55 (2 H, d), 7.39 (2 H, d), 7.01 (1 H, d), 6.85-6.93 (2 H, m), 6.75 (1 H, s), 3.89 (3 H, s), 3.88 (2 H, s), 1.37 (6 H, s). |
| J-3 | 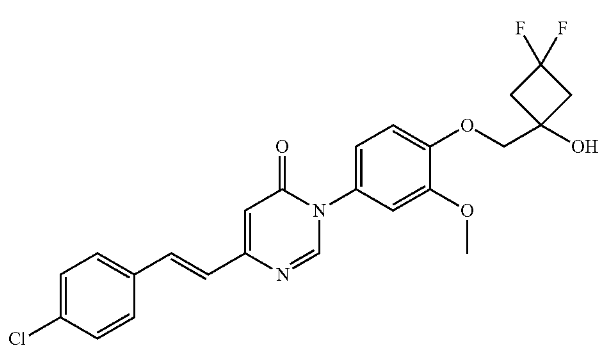 | # 20 | 1.00; method 5 | 475 | $^1$H NMR (400 MHz, Chloroform-d) δ 8.17 (1 H, s), 7.76 (1 H, d), 7.53 (2 H, d), 7.40 (2 H, d), 7.08 (1 H, d), 6.86-6.97 (3 H, m), 6.48 (1 H, s), 4.13 (2 H, s), 3.89 (3 H, s), 2.77-2.87 (4 H, m) |

TABLE K

| Ex. No. | Structure | Experimental Procedure Used | HPLC Method ($t_R$ Min) | MS (M + H) | NMR Data |
|---|---|---|---|---|---|
| K-1 | 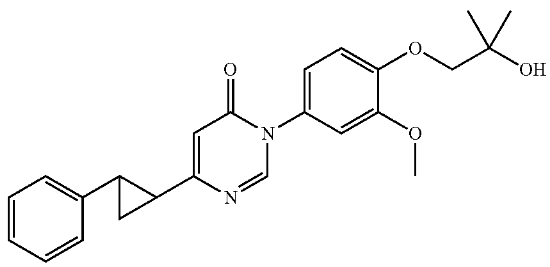 | # 14 | # 5 0.92 min | 407 | $^1$H NMR (400 MHz, Chloroform-d) δ 8.11 (1 H, s), 7.28-7.41 (2 H, m), 7.20-7.26 (1 H, m), 7.13-7.19 (2 H, m), 7.00 (1 H, d), 6.85-6.90 (2 H, m), 6.48 (1 H, s), 3.88 (5 H, br. s.), 2.60-2.66 (1 H, m), 2.08-2.14 (1 H, m), 1.75-1.81 (1 H, m), 1.51-1.57 (1 H, m), 1.37 (6 H, s). |

TABLE L

| Ex. No. | Structure | Experimental Procedure Used | HPLC Method ($t_R$ Min) | MS (M + H) | NMR Data |
|---|---|---|---|---|---|
| L-1 | 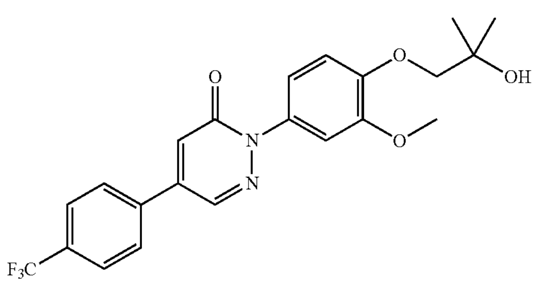 | # 18 | 3 5 0.94 min | 435 | $^1$H NMR (400 MHz, CHLOROFORM-d) δ ppm 8.20 (1 H, d, J = 2.01 Hz), 7.73-7.87 (4 H, m), 7.17-7.26 (3 H, m), 7.02 (1 H, d, J = 8.28 Hz), 3.91 (3 H, s), 3.89 (2 H, s), 1.38 (6 H, s) |

TABLE M

| Ex. No. | Structure | Experimental Procedure Used | HPLC Method ($t_R$ Min) | MS (M + H) | NMR Data |
|---|---|---|---|---|---|
| M-1 | 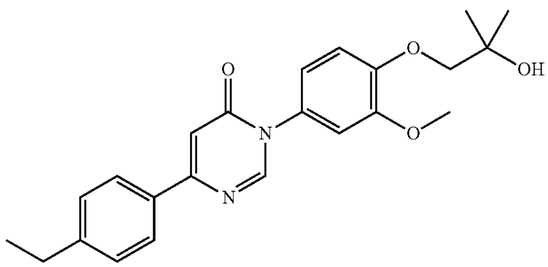 | #19 | #5 0.95 min | 395 | $^1$H NMR (400 MHz, CHLOROFORM-d) δ ppm 8.25 (1 H, s), 7.93 (2 H, d, J = 8.32 Hz), 7.34 (2 H, d, J = 8.32 Hz), 7.02 (1 H, d), 6.91-6.96 (3 H, m), 3.90 (3 H, s), 3.89 (2 H, s), 2.74 (2 H, q), 1.38 (6 H, s), 1.30 (3 H, t, J = 7.63 Hz) |
| M-2 | 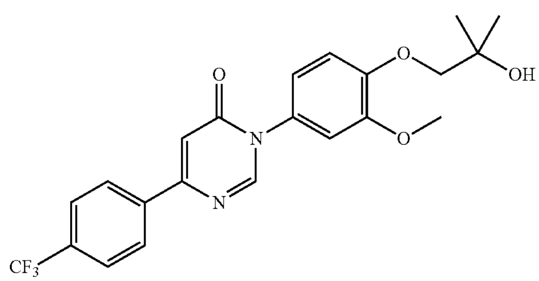 | #19 | #5 0.95 min | 435 | 1H NMR (400 MHz, CHLOROFORM-d) δ ppm 8.29 (1 H, s), 8.12 (2 H, d), 7.75-7.80 (2 H, m), 7.00-7.06 (2 H, m), 6.91-6.96 (2 H, m), 3.90 (3 H, s), 3.89 (2 H, s), 1.38 (6 H, s) |

ANALYTICAL HPLC CONDITIONS

Method 1. Phenomenex S5 C18, 4.6×30 mm column; 2 min gradient at 4 mL/min, 10:90:0.1 to 90:10:0.1 MeOH—H$_2$O-TFA with 1 min hold at the end of the gradient.

Method 2. Phenomenex Luna S5 C18, 4.6×30 mm column; 2 min gradient at 4 mL/min, 10 mM ammonium acetate in 90:10 water-acetonitrile to 10 mM ammonium acetate in 10:90 water-acetonitrile with 1 min hold at the end of the gradient.

Method 3. Phenomenex S5 C18, 4.6×30 mm column; 4 min gradient at 4 mL/min, 10:90:0.1 to 90:10:0.1 MeOH—H$_2$O-TFA with 2 mM hold at the end of the gradient.

Method 4. Phenomenex S5 C18, 4.6×30 mm column; 2 min gradient at 4 mL/min, 10:90:0.1 to 90:10:0.1 acetonitrile-H$_2$O-TFA with 1 min hold at the end of the gradient.

Method 5. BEH C18, 2.1×50 mm column; 1 min gradient at 0.8 mL/min, 2:98:0.05 to 98:2:0.05 acetonitrile-H$_2$O-TFA with 0.5 mM hold at the end of the gradient.

Method 6. Zorbax Column SB C18, 4.6×75 mm; Gradient Time: 8 min; Flow Rate: 2.5 mL/min.; Solvent Gradient: 50-100% B; Detector Wavelength: 220 nm. (Solvent A=10% MeOH-90% H$_2$O-0.2% H$_3$PO$_4$; Solvent B=90% MeOH-10% H$_2$O-0.2% H$_3$PO$_4$).

Method 7. Phenomenex Onyx Monolithic C18, 4.6×100 mm column; 4 min gradient at 4 mL/min, 10:90:0.1 to 90:10:0.1 MeOH—H$_2$O—H$_3$PO$_4$ with 1 min hold at the end of the gradient.

SYNTHETIC METHODS

Procedure 1

Example A-1

4-(4-Chlorobenzylthio)-1-(4-(2-hydroxy-2-methyl-propoxy)-3-methoxyphenyl)pyrimidin-2(1H)-one

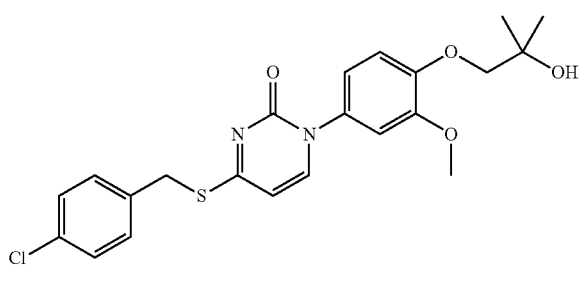

A. 4-(Methylthio)pyrimidin-2(1H)-one

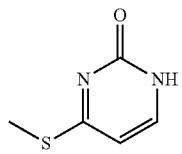

To a freshly prepared solution of NaOMe prepared by addition of sodium (0.177 g, 7.70 mmol) methanol (5 mL) was added 4-thiouracil (0.94 g, 7.34 mmol) and iodomethane (0.482 mL, 7.70 mmol) in methanol (30 mL). After stirring at RT for 8 h, the reaction was concentrated under vacuum. The residue was triturated with cold water to afford (methylthio)pyrimidin-2(1H)-one (0.51 g, 3.59 mmol, 49% yield) as a white solid.

B. 1-(4-Bromo-2-methoxyphenoxy)-2-methylpropan-2-ol

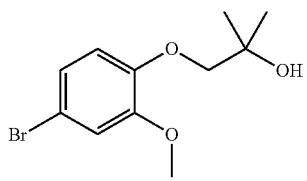

A mixture of 4-bromo-2-methoxyphenol (8 g, 39.4 mmol), 2,2-dimethyloxirane (14 mL, 158 mmol), potassium carbonate (4.3 g, 35.5 mmol), and sodium phosphate, monobasic (4.25 g, 35.5 mmol) in acetonitrile and water (85:15, 100 mL) was stirred in a steel bomb at 150-165° C. for 8 h. The reaction was cooled to RT, diluted with ether and EtOAc (1:1), washed with 1N NaOH, dried (Na$_2$SO$_4$), and concentrated. The crude was passed through a pad of silica gel using EtOAc for elution to afford the desired product 1-(4-bromo-2-methoxyphenoxy)-2-methylpropan-2-ol (10 g, 36.3 mmol, 92% yield) as a brown oil. $^1$H NMR (400 MHz, Chloroform-d) δ 6.95-7.08 (2H, m), 6.77 (1H, d, J=8.28 Hz), 3.85 (3H, s), 3.79 (2H, s), 1.34 (6H, s).

C. 1-(4-(2-Hydroxy-2-methylpropoxy)-3-methoxyphenyl)-4-(methylthio)pyrimidin-2(1H)-one

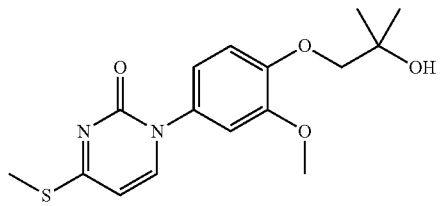

After addition of N,N'-Dimethylethane-1,2-diamine (1.6 g, 18.15 mmol) to a stirred mixture of 4-(methylthio)pyrimidin-2(1H)-one Part A (430 mg, 3.02 mmol), 1-(4-bromo-2-methoxyphenoxy)-2-methylpropan-2-ol Part B (1.0 g, 3.63 mmol), copper(I)iodide (346 mg, 1.82 mmol) and potassium phosphate, tribasic (3.85 g, 18.15 mmol) in 3:1 dioxane-DMF (80 mL), the mixture was stirred at 105° C. for 7 h. The reaction mixture was diluted with CH$_2$Cl$_2$, washed with saturated NaHCO$_3$, dried (MgSO$_4$) and concentrated. The crude product was subjected to flash chromatography (silica gel/hexane-EtOAc 100:0 to 0:100 gradient) to afford 1-(4-(2-hydroxy-2-methylpropoxy)-3-methoxyphenyl)-4-(methylthio)pyrimidin-2(1H)-one 1C (0.375 g, 37% yield). $^1$H NMR (400 MHz, chloroform-D) δ 7.37 (1H, d, J=7.03 Hz), 6.95 (1H, d, J=8.53 Hz), 6.92 (1H, d, J=2.51 Hz), 6.85 (1H, dd, J=8.53, 2.51 Hz), 6.28 (1H, d, J=7.03 Hz), 3.85 (3H, s), 3.84 (2H, s), 2.61 (3H, s), 2.59 (1H, s), 1.35 (6H, s).

D. 4-(4-Chlorobenzylthio)-1-(4-(2-hydroxy-2-methylpropoxy)-3-methoxyphenyl)pyrimidin-2(1H)-one

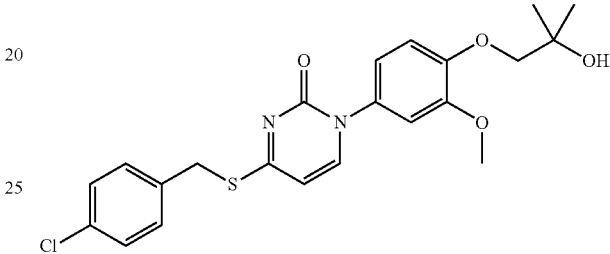

A mixture of 1-(4-(2-hydroxy-2-methylpropoxy)-3-methoxyphenyl)-4-(methylthio)pyrimidin-2(1H)-one (90 mg, 0.268 mmol) and (4-chlorophenyl)methanethiol (707 μl, 5.35 mmol) was heated to 145° C. (neat) for 30 min. The mixture was diluted with methylene chloride, washed with water, dried (Na$_2$SO$_4$) and concentrated. The crude product was subjected to ISCO flash chromatography (silica gel/hexanes:ethyl acetate 100:0 to 0:100 gradient) to afford the title compound 4-(4-chlorobenzylthio)-1-(4-(2-hydroxy-2-methylpropoxy)-3-methoxyphenyl)pyrimidin-2(1H)-one A-1 (83.5 mg, 0.187 mmol, 69.8% yield) as a yellow solid. LC/MS 447 (M+H)$^+$, t$_R$ 0.93 (method 5); $^1$H NMR (400 MHz, chloroform-D) δ 7.33-7.44 (3H, m), 7.24-7.31 (2H, m), 6.91-6.99 (2H, m), 6.86 (1H, dd, J=8.53, 2.51 Hz), 6.24 (1H, d, J=7.03 Hz), 4.48 (2H, s), 3.86 (3H, s), 3.85 (2H, s), 1.35 (6H, s).

Procedure 2

Example A-1

4-(4-Chlorobenzylthio)-1-(4-(2-hydroxy-2-methylpropoxy)-3-methoxyphenyl)pyrimidin-2(1H)-one

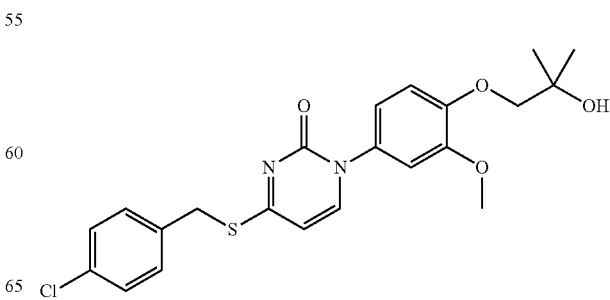

A. 4-(4-Chlorobenzylthio)pyrimidin-2(1H)-one

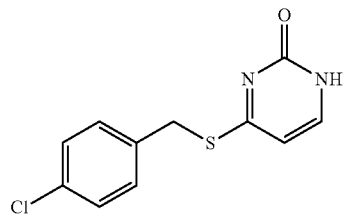

Sodium methoxide (0.057 g, 1.050 mmol) was added to a mixture of 4-thiouracil (0.128 g, 1.0 mmol) and 1-(bromomethyl)-4-chlorobenzene (0.216 g, 1.05 mmol) in 1 mL MeOH. After stirring the reaction at RT overnight, the reaction mixture was concentrated, partitioned between EtOAc and sat. NH$_4$Cl. The organic phase was dried (MgSO$_4$), concentrated and the residue was subjected to ISCO flash chromatography (silica gel/methylene chloride to 80:20 methylene chloride-MeOH gradient) to afford 4-(4-chlorobenzylthio)pyrimidin-2(1H)-one 2A (0.17 g, 0.673 mmol, 67% yield) as a light yellow solid. $^1$H NMR (400 MHz, methanol-D) δ 7.58 (1H, d, J=6.78 Hz), 7.43 (2H, d, J=8.53 Hz), 7.30 (2H, d, J=8.53 Hz), 6.39 (1H, d, J=6.78 Hz), 4.44 (2H, s).

B. 4-(4-Chlorobenzylthio)-1-(4-(2-hydroxy-2-methylpropoxy)-3-methoxyphenyl)pyrimidin-2(1H)-one

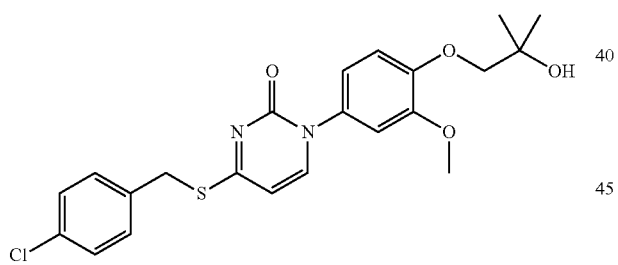

N1,N2-dimethylethane-1,2-diamine (356 mg, 4.04 mmol) was added to a stirred mixture of 1-(4-bromo-2-methoxyphenoxy)-2-methylpropan-2-ol Part 1B of Procedure 1 (222 mg, 0.807 mmol), 4-(4-chlorobenzylthio)pyrimidin-2(1H)-one Part A (170 mg, 0.67 mmol), copper(I) iodide (77 mg, 0.404 mmol) and potassium phosphate, tribasic (857 mg, 4.04 mmol) in dioxane (8 mL). The mixture was stirred at 105° C. for 7 h. The reaction mixture was diluted with methylene chloride, washed with saturated sodium bicarbonate, dried (MgSO$_4$) and concentrated. The crude product was subjected to ISCO flash chromatography (silica gel/hexane-EtOAc 100:0 to 0:100 gradient, used LC/MS to identify fractions containing the desired product) to afford the title compound 4-(4-chlorobenzylthio)-1-(4-(2-hydroxy-2-methylpropoxy)-3-methoxyphenyl)pyrimidin-2(1H)-one A-1 (22 mg, 0.048 mmol, 7% yield, eluted with 100% EtOAc) as a pale gummy solid.

Procedure 3

Example A-8

4-(4-Chlorobenzyloxy)-1-(4-(2-hydroxy-2-methylpropoxy)-3-methoxyphenyl)pyrimidin-2(1H)-one

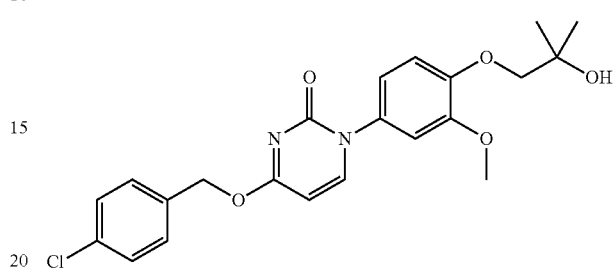

A stirred mixture of 1-(4-(2-hydroxy-2-methylpropoxy)-3-methoxyphenyl)-4-(methylthio)pyrimidin-2(1H)-one Part C of Procedure 1 (10 mg, 0.03 mmol), (4-chlorophenyl)methanol (85 mg, 0.6 mmol) and K$_2$CO$_3$ (12 mg, 0.09 mmol) in NMP (0.1 mL) was heated at 145° C. for 60 min, diluted with CH$_2$Cl$_2$, washed with water, dried (MgSO$_4$), and concentrated. The residue was purified by flash chromatography (silica gel/hexane-EtOAc 100:0:0 to 0:100 gradient) to afford the title compound 4-(4-chlorobenzyloxy)-1-(4-(2-hydroxy-2-methylpropoxy)-2-methylpropoxy)-3-methoxyphenyl)pyrimidin-2(1H)-one A-8 (5 mg, 36% yield) as a white solid. LC/MS 431 (M+H)$^+$, t$_R$ 0.9 min (method 5); $^1$H NMR (400 MHz, chloroform-D) δ 7.53 (1H, d, J=7.03 Hz), 7.40 (2H, d, J=8.53 Hz), 7.37 (2H, d, J=8.78 Hz), 6.96 (1H, d, J=8.53 Hz), 6.91 (1H, d, J=2.26 Hz), 6.85 (1H, dd, J=8.53, 2.51 Hz), 6.00 (1H, d, J=7.03 Hz), 5.45 (2H, s), 3.86 (3H, s), 3.85 (2H, s), 1.35 (6H, s).

Procedure 4

Example B-1

1-(4-(2-Hydroxy-2-methylpropoxy)-3-methoxyphenyl)-4-(phenylethynyl)pyrimidin-2(1H)-one

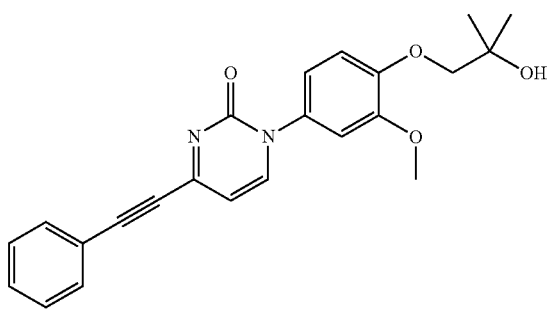

A. 2-Oxo-1-trityl-1,2-dihydropyrimidin-4-yl 2,4,6-triisopropylbenzenesulfonate

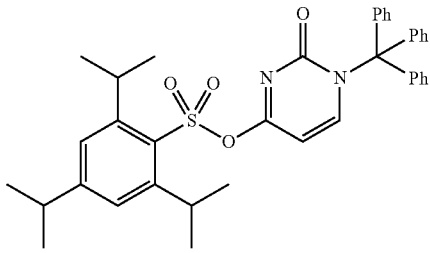

Sodium hydride (0.494 g, 12.3 mmol) was added to a stirred solution of 1-tritylpyrimidine-2,4(1H,3H)-dione (1.75 g, 4.9 mmol) in dry THF (75 mL) at RT. After stirring the mixture at RT for 45 min, 2,4,6-triisopropylbenzene-1-sulfonyl chloride (2.99 g, 9.9 mmol) was added and stirring continued at RT for 2 h. The reaction mixture was poured into a stirred mixture of EtOAc and saturated ammonium chloride solution. The organic layer was dried (MgSO₄), concentrated and the residue was subjected to flash chromatography (silica gel/hexane-EtOAc 100:0 to 0:100 gradient) to afford 2-oxo-1-trityl-1,2-dihydropyrimidin-4-yl 2,4,6-triisopropylbenzenesulfonate 4A (1.6 g, 52% yield) as a white solid.

B. 4-(Phenylethynyl)pyrimidin-2(1H)-one

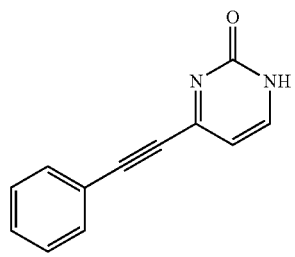

Tributyl(phenylethynyl)stannane (315 mg, 0.8 mmol) was added to a stirred solution of 2-oxo-1-trityl-1,2-dihydropyrimidin-4-yl 2,4,6-triisopropylbenzenesulfonate Part A (200 mg, 0.3 mmol), copper (I) iodide (18.4 mg, 0.1 mmol) and palladium tetrakis (55.8 mg, 0.05 mmol) in 5 mL DMF under nitrogen. The reaction mixture was heated at 55° C. for 16 h, concentrated and subjected to flash chromatography (silica gel/methylene chloride to 15% MeOH-methylene chloride gradient to afford 4-(phenylethynyl)pyrimidin-2(1H)-one 4B (66 mg) as a brownish solid.

C. 1-(2-Methoxy-4-(4,4,5,5-tetramethyl-1,3,2-dioxaborolan-2-yl)phenoxy)-2-methylpropan-2-ol

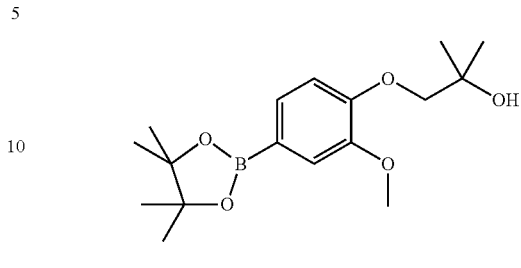

1-(4-Bromo-2-methoxyphenoxy)-2-methylpropan-2-ol (1 g, 3.63 mmol) was dissolved in DMF (10 mL) under N₂ and potassium acetate (1 g, 10.90 mmol), bis(pinacolato)diboron (1 g, 3.82 mmol), and PdCl₂(dppf)-CH₂Cl₂ (0.15 g, 0.182 mmol) were added. The reaction mixture was heated at 90° C. for 1 h. (Terranova, Eric; Pascal, Jean Claude. (Galderma Research & Development, Fr.). WO 2004-FR3192; US 2007/001593). The reaction was diluted with EtOAc, washed sat NH₄Cl, brine, dried (MgSO₄), and concentrated to afford the crude product. The residue was purified using ISCO flash chromatography (silica gel/hexanes/ethyl acetate 100:0 to 0:100 gradient) to afford the desired product 1-(2-methoxy-4-(4,4,5,5-tetramethyl-1,3,2-dioxaborolan-2-yl)phenoxy)-2-methylpropan-2-ol 4C (1.05 g, 3.26 mmol, 90% yield) as a yellow oil.

D. 4-(2-Hydroxy-2-methylpropoxy)-3-methoxyphenylboronic acid

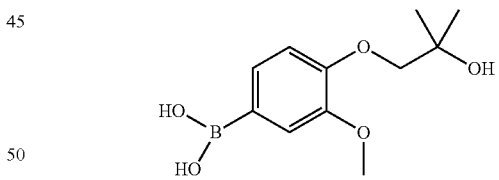

To a solution of 1-(2-methoxy-4-(4,4,5,5-tetramethyl-1,3,2-dioxaborolan-2-yl)phenoxy)-2-methylpropan-2-ol Part C (0.880 g, 2.73 mmol) in acetone (20 mL) and water (20 mL) was added sodium periodate (2.3 g, 10.92 mmol) and ammonium acetate (0.84 g, 10.92 mmol). The mixture stirred at RT overnight. Filtered the white solids, washed the filter cake with acetone and removed the acetone. The product was then extracted with EtOAc, and brine, and, dried (MgSO₄), concentrated to afford the crude product. Residue was purified using ISCO flash chromatography (silica gel/methylene chloride-methanol 100:0 to 85:15 gradient) to afford the desired product 4-(2-hydroxy-2-methylpropoxy)-3-methoxyphenylboronic acid 4D (0.443 g, 1.845 mmol, 67.6% yield) as a light brown solid.

E. 1-(4-(2-Hydroxy-2-methylpropoxy)-3-methoxyphenyl)-4-(phenylethynyl)pyrimidin-2(1H)-one

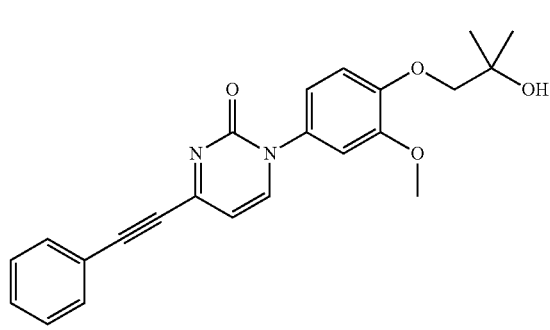

To a stirred mixture of 4-(phenylethynyl)pyrimidin-2(1H)-one Part B (20 mg, 0.1 mmol), 4-(2-hydroxy-2-methylpropoxy)-3-methoxyphenylboronic acid Part D (48.9 mg, 0.2 mmol), and copper (II) acetate (18.5 mg, 0.1 mmol) in MeOH (2 mL) and H$_2$O (0.5 mL) was added N1,N1,N2,N2-tetramethylethane-1,2-diamine (24 mg, 0.2 mmol) at RT. The reaction mixture was stirred at RT for 45 min under oxygen, diluted with CH$_2$Cl$_2$, washed sequentially with 5% aq. H$_2$SO$_4$ and sat. NaHCO$_3$. The organic phase was dried (MgSO$_4$), concentrated, and the residue was subjected to flash chromatography (silica gel/hexane-EtOAc 100:0 to 0:100 gradient) to afford impure product. Trituration with methyl t-butyl ether yielded the title compound B-1 (15 mg, 0.038 mmol, 37% yield) as a pure solid. LC/MS 391 (M+H)$^+$, t$_R$ 0.82 min (method 5); $^1$H NMR (400 MHz, chloroform-D) δ 7.70 (1H, d, J=6.78 Hz), 7.51-7.66 (2H, m), 7.37-7.47 (3H, m), 6.95-7.12 (2H, m), 6.90 (1H, dd, J=8.53, 2.51 Hz), 6.54 (1H, d, J=6.78 Hz), 3.88 (3H, s), 3.85 (2H, s), 1.36 (6H, s).

Procedure 5

Example B-6

(E)-4-(4-Chlorostyryl)-1-(4-(2-hydroxy-2-methylpropoxy)-3-methoxyphenyl)pyrimidin-2(1H)-one

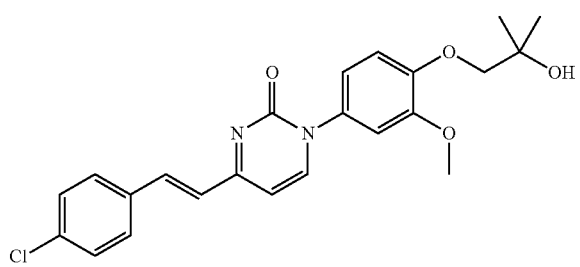

A. (E)-4-(4-Chlorostyryl)pyrimidin-2(1H)-one

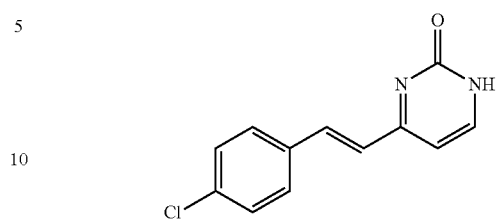

A mixture of 2-oxo-1-trityl-1,2-dihydropyrimidin-4-yl 2,4,6-triisopropylbenzenesulfonate Part A of Procedure 4 (100 mg, 0.16 mmol), (E)-4-chlorostyrylboronic acid (73.5 mg, 0.4 mmol), potassium phosphate, tribasic (103 mg, 0.48 mmol) and palladium tetrakis (9.3 mg, 8.0 μmol) in DMF (2.5 mL) was stirred at 48° C. for 14 h, diluted with CH$_2$Cl$_2$ and washed with saturated sodium bicarbonate solution. The organic phase was dried (MgSO$_4$) and concentrated under vacuum. The residue was sonicated with MeOH and filtered. The MeOH soluble fraction was subjected to preparative HPLC (ODS column/water-MeOH-TFA 90:10:0.1 to 10:90:0.1 gradient) to afford the desired product 5A as a yellow solid (8 mg). $^1$H NMR (400 MHz, CD$_3$OD) δ 8.29 (1H, d, J=6.02 Hz), 8.07 (1H, d, J=16.31 Hz), 7.73 (2H, d, J=8.28 Hz), 7.50 (2H, d, J=8.53 Hz), 7.08 (1H, d, J=16.31 Hz), 7.06 (1H, d, J=6.27 Hz). The MeOH insoluble fraction was triturated with MTBE to afford 13 mg of slightly less pure product (56% combined yield).

B. (E)-4-(4-Chlorostyryl)-1-(4-(2-hydroxy-2-methylpropoxy)-3-methoxyphenyl)pyrimidin-2(1H)-one

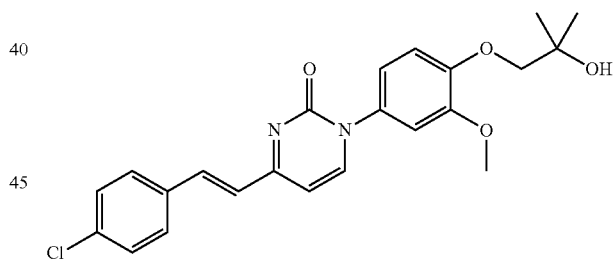

To a stirred mixture of (E)-4-(4-chlorostyryl)pyrimidin-2(1H)-one Part A (21 mg, 0.09 mmol), 4-(2-hydroxy-2-methylpropoxy)-3-methoxyphenylboronic acid Part D of Procedure 4 (43 mg, 0.18 mmol) and copper (II) acetate (16.39 mg, 0.090 mmol) in MeOH (2 mL) and H$_2$O (0.5 mL) was added N1,N1,N2,N2-tetramethylethane-1,2-diamine (21 mg, 0.18 mmol) at RT. After stirring at RT for 45 min under oxygen, the reaction diluted with CH$_2$Cl$_2$ and washed sequentially with 5% aq. sulfuric acid and sat. NaHCO$_3$. The organic phase was dried (MgSO$_4$) and concentrated. LC/MS showed incomplete reaction (starting pyrimidinone:desired product=ca. 4:1). The crude product mixture was resubjected to the above reaction conditions using another 2 equivalents of the boronic acid, copper salt and N1,N1,N2,N2-tetramethylethane-1,2-diamine After the above described workup, the crude product mixture was subjected to preparative HPLC (ODS column/water-MeOH-TFA 90:10:0.1 to 10:90:0.1 gradient) to afford a brown solid. Further purification was achieved by dissolution of this solid in a few drops of MeOH followed by addition of MTBE (ca. 1 mL) which upon standing at RT induced the formation of a yellow precipitate. The precipitated yellow solid was isolated to afford the title compound (E)-4-(4-chlorostyryl)-1-(4-(2-hydroxy-2-methylpropoxy)-3-methoxyphenyl)pyrimidin-2(1H)-one B-6 (8 mg, 0.018 mmol, 20% yield) as a yellow solid. LC/MS 427 (M+H)$^+$, $t_R$ 0.84 min (method 5); $^1$H NMR (400 MHz, chloroform-D) δ 7.91 (1H, d, J=16.06 Hz), 7.69 (1H, d, J=6.78 Hz), 7.54 (2H, d, J=8.28 Hz), 7.39 (2H, d, J=8.53 Hz), 6.87-7.01 (4H, m), 6.49 (1H, d, J=6.78 Hz), 3.87 (3H, s), 3.85 (2H, s), 1.36 (6H, s).

Procedure 6

Example C-1

4-((4-Chlorophenoxy)methyl)-1-(4-(2-hydroxy-2-methylpropoxy)-3-methoxyphenyl)pyrimidin-2(1H)-one

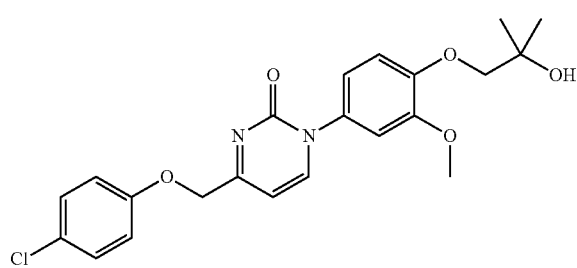

A. 4-((4-Chlorophenoxy)methyl)-2-(methylthio)pyrimidine

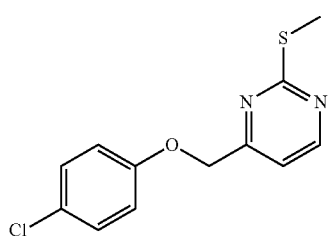

To a solution of (2-(methylthio)pyrimidin-4-yl)methanol (US 2005/0148610) (0.515 g, 3.30 mmol), 4-chlorophenol (0.466 g, 3.63 mmol), and triphenylphosphine (1.297 g, 4.95 mmol) in THF (10 mL) was added a solution of 1,1'-(azodicarbonyl)dipiperidine (1.248 g, 4.95 mmol) in THF (10 mL) dropwise. After stirring the reaction at RT overnight, the solids were filtered. The filtrate was diluted with EtOAc (30 mL), washed with water (20 mL) and by brine. The organic phase was dried (Na$_2$SO$_4$) and concentrated to afford the crude product. The crude product was purified using flash chromatography (silica gel/hexanes-ethyl acetate 100:0 to 0:100 gradient) to afford the desired product 4-((4-chlorophenoxy)methyl)-2-(methylthio)pyrimidine 6A (0.825 g, 3.09 mmol, 94% yield) as a light yellow solid. $^1$H NMR (400 MHz, Chloroform-D) δ 8.45 (1H, d, J=5.02 Hz), 7.18 (2H, d, J=8.78 Hz), 7.07-7.13 (1H, m), 6.80 (2H, d, J=8.78 Hz), 4.99 (2H, s), 2.51 (3H, s).

B. 4-((4-Chlorophenoxy)methyl)-2-(methylsulfonyl)pyrimidine

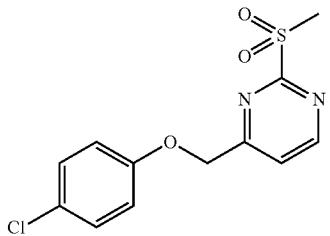

To a 0° C. solution of 4-((4-chlorophenoxy)methyl)-2-(methylthio)pyrimidine Part A (0.825 g, 3.09 mmol) in CH$_2$Cl$_2$ (30 mL) was added 70% mCPBA (3.4 g, 13.92 mmol). The mixture was warmed to RT and stirred for 5 hours before dilution with CH$_2$Cl$_2$ (20 mL), washing with 5% sodium thiosulfate, drying (Na$_2$SO$_4$), and concentration. The crude product was purified using flash chromatography (silica gel/CH$_2$Cl$_2$-MeOH 100:0 to 90:10 gradient) to afford the desired product 4-((4-chlorophenoxy)methyl)-2-(methylsulfonyl)pyrimidine 6B (1.01 g, 2.87 mmol, 93% yield) as a light yellow solid. $^1$H NMR (400 MHz, Chloroform-D) δ 8.95 (1H, d, J=5.27 Hz), 7.83 (1H, d, J=5.02 Hz), 7.27-7.36 (2H, m), 6.89-6.97 (2H, m), 5.28 (2H, s), 3.41 (3H, s).

C.

4-((4-Chlorophenoxy)methyl)pyrimidin-2(1H)-one

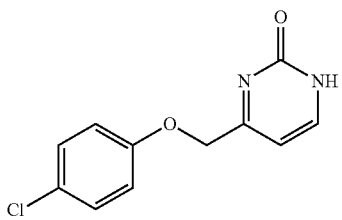

4-((4-Chlorophenoxy)methyl)-2-(methylsulfonyl)pyrimidine Part B (0.8 g, 2.68 mmol) was stirred in 1N NaOH (5 mL, 5.36 mmol) and THF (13 mL) at 80° C. for 30 min. The solution was cooled to RT, acidified to pH 3 using 10% aqueous HCl. The precipitated product after isolation by filtration, was washed with CH$_2$Cl$_2$ to afford the desired product 4-((4-chlorophenoxy)methyl)pyrimidin-2(1H)-one 6C (0.344 g, 1.45 mmol, 54% yield) as a light brown solid. $^1$H NMR (400 MHz, DMSO-d$_6$) δ 7.93 (1H, d, J=5.27 Hz), 7.28-7.36 (2H, m), 6.94-7.02 (2H, m), 6.10 (1H, d, J=5.27 Hz), 4.78 (2H, s).

D. 4-((4-Chlorophenoxy)methyl)-1-(4-(2-hydroxy-2-methylpropoxy)-3-methoxyphenyl)pyrimidin-2(1H)-one

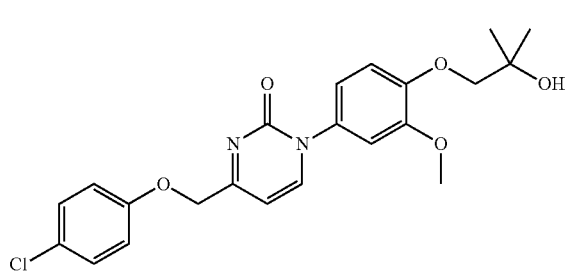

To a mixture of 4-((4-chlorophenoxy)methyl)pyrimidin-2(1H)-one Part C (0.2 g, 0.845 mmol), 4-(2-hydroxy-2-methylpropoxy)-3-methoxyphenylboronic acid Part D of Procedure 4 (0.304 g, 1.268 mmol), and copper (II) acetate monohydrate (0.169 g, 0.845 mmol) in MeOH (45 mL) and H₂O (11 mL) was added N,N,N',N'-tetramethylethylenediamine (0.26 mL, 1.690 mmol). After stirring at RT for 45 minutes in the presence of air, the mixture was extracted with CH₂Cl₂ (200 mL). The organic phase was dried (Na₂SO₄) and concentrated. The residue was purified by flash chromatography (silica gel/100:0 to 0:100 hexanes-ethyl acetate to 95:5 CH₂Cl₂/MeOH gradient). The product thus obtained was re-purified using prep HPLC (Phen Luna Axia C18 5μ 10:90 to 90:10 MeOH/H₂O) to afford the desired product 4-((4-chlorophenoxy)methyl)-1-(4-(2-hydroxy-2-methylpropoxy)-3-methoxyphenyl)pyrimidin-2(1H)-one C-1 (16.9 mg, 0.036 mmol, 4.32% yield) as a yellow solid. 100 mg of starting material 4-((4-chlorophenoxy)methyl)pyrimidin-2(1H)-one was also recovered. LC/MS 431 (M+H)$^+$, $t_R$ 0.81 min (method 5); $^1$H NMR (400 MHz, Chloroform-D) δ 7.73 (1H, d, J=6.78 Hz), 7.28-7.31 (2H, m), 6.94-7.03 (2H, m), 6.86-6.94 (3H, m), 6.66 (1H, d, J=7.03 Hz), 5.02 (2H, s), 3.87 (3H, s), 3.86 (2H, s), 1.36 (6H, s).

Procedure 7

Example E-1

5-((4-Chlorophenylthio)methyl)-2-(4-(2-hydroxy-2-methylpropoxy)-3-methoxyphenyl)pyridazin-3(2H)-one

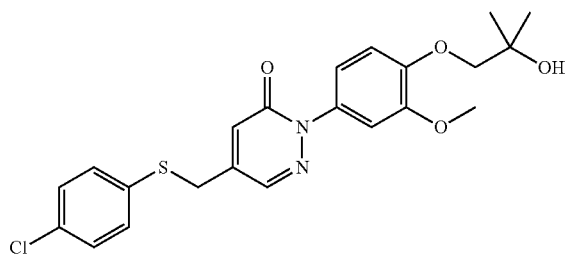

A. t-Butyl 6-oxo-4-vinylpyridazine-1(6H)-carboxylate

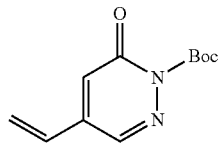

A mixture of vinyl tri-n-butyl tin (1.62 g, 5.12 mmol), tert-butyl 4-iodo-6-oxopyridazine-1(6H)-carboxylate (Coelho, A. et al., *Tetrahedron*, 60:12177 (2004), 12177) (1.50 g, 4.66 mmol) and bis(triphenylphosphine)palladium(II)chloride (0.16 g, 0.23 mmol) in toluene (20 mL) under nitrogen in a sealed tube was stirred at 110° C. for 2 hours. After filtration of the precipitate, the filtrate was concentrated. The crude product was subjected to flash chromatography (silica gel/hexane-EtOAc 100:0 to 0:100 gradient, using LC-MS to identify fractions containing the desire product) to afford tert-butyl 6-oxo-4-vinylpyridazine-1(6H)-carboxylate 7A (680 mg, 62% yield).

B. tert-Butyl 4-(hydroxymethyl)-6-oxopyridazine-1(6H)-carboxylate

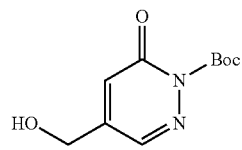

Ozone was bubbled through a solution of tert-butyl 6-oxo-4-vinylpyridazine-1(6H)-carboxylate Part A (680 mg, 3.06 mmol) in DCM (30 mL) at −78° C. until the mixture turned to light blue. The mixture was flushed with nitrogen to remove excess ozone. After addition of Me₂S (2.0 mL, 27.0 mmol), the reaction was stirred at RT for 2 hours. Following dilution with water (50 mL), the mixture was extracted with CH₂Cl₂ (2×40 mL). The CH₂Cl₂ layer was dried over Na₂SO₄ and concentrated to give light brown gum. After dissolution of this material in THF (30 mL), NaBH₄ (174 mg, 4.59 mmol) in MeOH (10 mL) was added. The mixture was stirred at RT for 30 min prior to dilution with CH₂Cl₂ (50 mL) and washing with 1.0 N aqueous HCl (50 mL). The CH₂Cl₂ layer was dried over Na₂SO₄ and concentrated. The crude product was subjected to flash chromatography (silica gel/hexane-EtOAc 100:0 to 0:100 gradient, using LC-MS to identify fractions containing the desired product) to afford tert-butyl 4-(hydroxymethyl)-6-oxopyridazine-1(6H)-carboxylate 7B (185 mg, 27% yield).

C. t-Butyl 4-((4-chlorophenylthio)methyl)-6-oxopyridazine-1(6H)-carboxylate

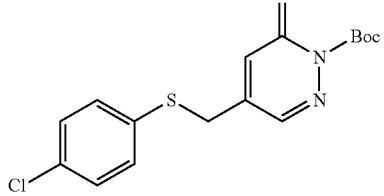

To a solution of tert-butyl 4-(hydroxymethyl)-6-oxopyridazine-1(6H)-carboxylate Part B (185 mg, 0.82 mmol) and Et$_3$N (0.34 mL, 2.45 mmol) in CH$_2$Cl$_2$ (5 mL) under nitrogen at −10° C. was added a solution of methanesulfonyl chloride (0.076 mL, 0.98 mmol) in CH$_2$Cl$_2$ (2 mL). After stirring at RT for 15 min, 4-chlorobenzenethiol (355 mg, 2.45 mmol) was added to the reaction and the stirring at RT continued for 3 days. Following removal of the volatiles under vacuum, the crude product was purified by flash chromatography (silica gel/hexane-EtOAc 100:0 to 50:50 gradient, using LC-MS to identify fractions containing the desired product) to afford tert-butyl 4-((4-chlorophenylthio)methyl)-6-oxopyridazine-1(6H)-carboxylate 7C (137 mg, 47% yield).

D. 5-((4-Chlorophenylthio)methyl)pyridazin-3(2H)-one

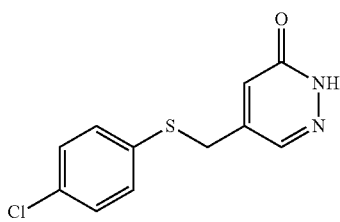

To a solution of tert-butyl 4-((4-chlorophenylthio)methyl)-6-oxopyridazine-1(6H)-carboxylate Part C (137 mg, 0.34 mmol) in CH$_2$Cl$_2$ (5 mL) was added TFA (1.50 mL, 19.41 mmol). The mixture was stirred at RT for 15 min before being concentrated. The crude product was subjected to flash chromatography (silica gel/hexane-EtOAc 100:0 to 0:100 gradient, using LC-MS to identify fractions containing the desired product) to afford 5-((4-chlorophenylthio)methyl)pyridazin-3(2H)-one 7D (81 mg, 81% yield). $^1$H NMR (400 MHz, Chloroform-D) δ ppm 7.76 (1H, d, J=2.01 Hz), 7.27 (4H, s), 6.56 (1H, s), 3.82 (2H, s).

E. 5-((4-Chlorophenylthio)methyl)-2-(4-(2-hydroxy-2-methylpropoxy)-3-methoxyphenyl)pyridazin-3(2H)-one

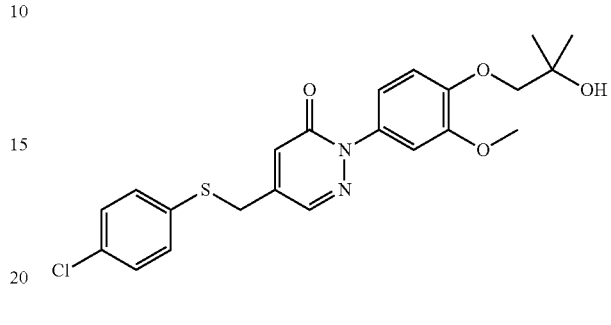

To a mixture of 5-((4-chlorophenylthio)methyl)pyridazin-3(2H)-one Part D (60 mg, 0.24 mmol), copper(II) acetate (95 mg, 0.48 mmol), and 4-(2-hydroxy-2-methylpropoxy)-3-methoxyphenylboronic acid Part D of Procedure 4 (114 mg, 0.48 mmol) in CH$_2$Cl$_2$ (20 mL) stirring at RT open to air was added pyridine (1.92 mL, 23.74 mmol) in portions over 4 hours. The mixture was poured into 3.0 N aqueous HCl (100 mL) and extracted with CH$_2$Cl$_2$. The CH$_2$Cl$_2$ layer was dried over Na$_2$SO$_4$ and concentrated. The crude product was subjected to flash chromatography (silica gel/hexane-EtOAc 100:0 to 0:100 gradient, using LC-MS to identify fractions containing the desired product). This material was further purified by preparative HPLC (C18 column/Water:MeOH:TFA 90:10:0.1 to 10:90:0.1 gradient). The clean fractions were lyophilized using MeCN/H$_2$O (1:1, 10 mL) to obtain the title compound 5-((4-chlorophenylthio)methyl)-2-(4-(2-hydroxy-2-methylpropoxy)-3-methoxyphenyl)pyridazin-3(2H)-one E-1 (57 mg, 53% yield) as white solid. LC/MS 447 (M+H)$^+$, t$_R$ 0.95 min (method 5); $^1$H NMR (400 MHz, Chloroform-D) δ ppm 7.85 (1H, d, J=2.26 Hz), 7.30 (4H, s), 7.09-7.14 (2H, m), 6.96 (1H, d, J=9.29 Hz), 6.68-6.72 (1H, m), 3.87 (7H, t, J=5.40 Hz), 1.35 (6H, s).

Procedure 8

Example E-2

5-((4-Chlorophenoxy)methyl)-2-(4-(2-hydroxy-2-methylpropoxy)-3-methoxyphenyl)pyridazin-3(2H)-one

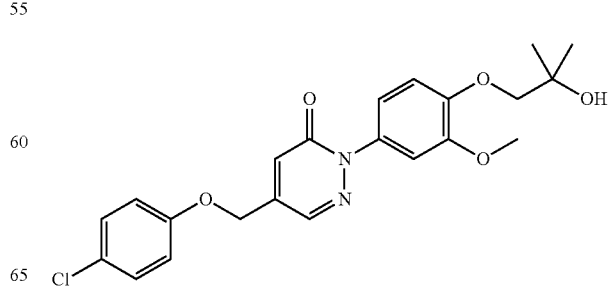

A. ((4-Chlorophenoxy)methyl)trimethylstannane

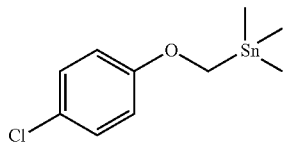

To a suspension of NaH (140 mg, 5.83 mmol) in anhydrous THF (150 mL) under $N_2$ at RT was added dropwise 4-chlorophenol (738 mg, 5.74 mmol). After stirring the mixture at RT for 15 min, (chloromethyl)trimethylstannane (350 mg, 1.64 mmol) in anhydrous THF (5 mL) was added and the reaction was stirred at RT for 18 hours. The mixture was diluted with EtOAc (50 mL) and was washed with aqueous 1.0 N NaOH (3×60 mL). The EtOAc layer was dried over $Na_2SO_4$ and concentrated. The crude product was purified by flash chromatography (silica gel/hexane, using LC-MS to identify fractions containing the desire product) to afford ((4-chlorophenoxy)methyl)-trimethylstannane 8A (457 mg, 87% yield). $^1$H NMR (400 MHz, Chloroform-D) δ ppm 7.03 (2H, d, J=8.78 Hz), 6.67 (2H, d, J=9.03 Hz), 3.94 (2H, s), 0.00 (9H, s).

B. 5-((4-Chlorophenoxy)methyl)pyridazin-3(2H)-one

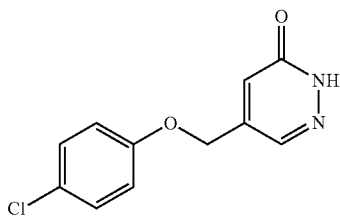

A mixture of tributyl((4-chlorophenoxy)methyl)stannane (29.5 mg, 0.068 mmol), tert-butyl 4-iodo-6-oxopyridazine-1(6H)-carboxylate (20 mg, 0.062 mmol) and bis(triphenylphosphine)palladium(II)chloride (2.18 mg, 3.10 μmol) in toluene (1.0 mL) under nitrogen in a sealed tube was stirred at 110° C. for 2 hours. After removal of the precipitate, the filtrate was concentrated and dissolved in $CH_2Cl_2$ (3.0 mL). After addition of TFA (1.0 mL, 12.98 mmol), the solution was stirred at RT for 15 min before being concentrated. The crude product was purified by prep-HPLC (C18 column/Water:MeOH:TFA 90:10:0.1 to 10:90:0.1 gradient) to give 5-((4-chlorophenoxy)methyl)pyridazin-3(2H)-one 8B (5.0 mg, 33% yield). $^1$H NMR (400 MHz, THF-D8) δ ppm 5.99 (1H, d, J=1.76 Hz), 5.55 (2H, d, J=8.78 Hz), 5.27 (2H, d, J=9.03 Hz), 5.08 (1H, d, J=1.51 Hz), 3.24 (2H, s).

C. 5-((4-Chlorophenoxy)methyl)-2-(4-(2-hydroxy-2-methylpropoxy)-3-methoxyphenyl)pyridazin-3(2H)-one

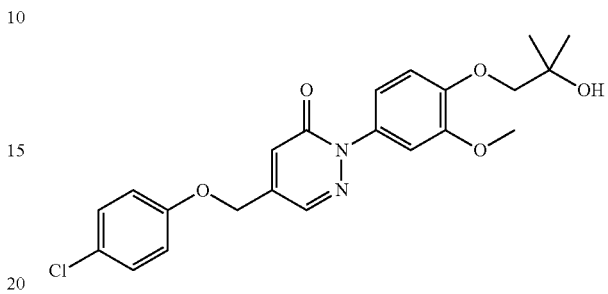

Pyridine (0.123 mL, 1.52 mmol) was added in portions over 4 hr to a stirred mixture of 5-((4-chlorophenoxy)methyl)pyridazin-3(2H)-one Part B (36 mg, 0.15 mmol), copper(II) acetate (91 mg, 0.46 mmol), and 4-(2-hydroxy-2-methylpropoxy)-3-methoxyphenylboronic acid Part D of Procedure 4 (73.0 mg, 0.30 mmol) in $CH_2Cl_2$ (15 mL) at RT (flask left open to air). The mixture was poured into 3.0 N aqueous HCl (100 mL) and extracted with $CH_2Cl_2$. The $CH_2Cl_2$ layer was dried over $Na_2SO_4$ and concentrated. The crude product was purified by prep-HPLC (C18 column/$H_2O$:MeOH:TFA 90:10:0.1 to 10:90:0.1 gradient) giving the title compound 5-((4-chlorophenoxy)methyl)-2-(4-(2-hydroxy-2-methylpropoxy)-3-methoxyphenyl)pyridazin-3(2H)-one E-2 (25 mg, 38% yield) as an off-white solid. LC/MS 431 (M+H)$^+$, $t_R$ 0.93 min (method 5); $^1$H NMR (500 MHz, Chloroform-D) δ ppm 7.94 (1H, d, J=1.92 Hz), 7.30 (2H, d), 7.12-7.17 (2H, m), 7.09 (1H, br. s.), 6.98 (1H, d, J=8.25 Hz), 6.91 (2H, d), 4.97 (2H, s), 3.82-3.92 (5H, m), 1.35 (6H, s).

Procedure 9

Example F-1

5-(4-Chlorobenzylthio)-2-(4-(2-hydroxy-2-methylpropoxy)-3-methoxyphenyl)pyridazin-3(2H)-one

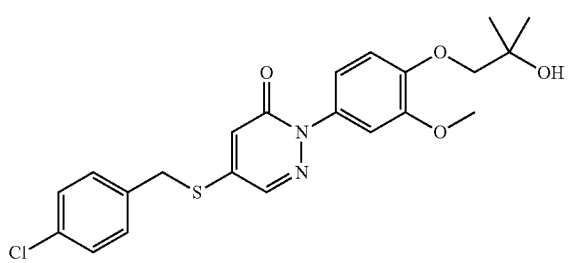

A. 5-(4-Chlorobenzylthio)pyridazin-3(2H)-one

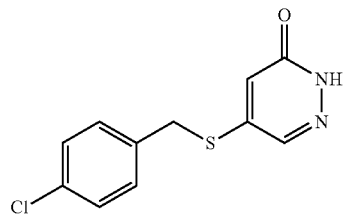

A mixture of K₂CO₃ (65.4 mg, 0.47 mmol), (4-chlorophenyl)methanethiol (250 mg, 1.58 mmol), and 5-iodopyridazin-3(2H)-one (35 mg, 0.16 mmol) was stirred at 100° C. for 18 hours. After removal of the precipitate by filtration and concentration of the filtrate, the crude product was purified by prep-HPLC (C18 column/H₂O:MeOH:TFA 90:10:0.1 to 10:90:0.1 gradient) to yield 5-(4-chlorobenzylthio)pyridazin-3(2H)-one 9A (21 mg, 51.6% yield). $^1$H NMR (400 MHz, Chloroform-D) δ ppm 11.08 (1H, br. s.), 7.57 (1H, d, J=2.01 Hz), 7.33 (4H, s), 6.57 (1H, d, J=2.01 Hz), 4.12 (2H, s).

B. 5-(4-Chlorobenzylthio)-2-(4-(2-hydroxy-2-methylpropoxy)-3-methoxyphenyl)pyridazin-3(2H)-one

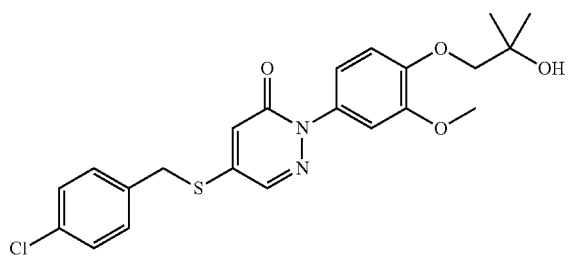

A solution of 5-(4-chlorobenzylthio)pyridazin-3(2H)-one Part A (21 mg, 0.083 mmol), 4-(2-hydroxy-2-methylpropoxy)-3-methoxyphenylboronic acid Part D of Procedure 4 (39.9 mg, 0.17 mmol), pyridine (0.067 mL, 0.83 mmol) and Cu(OAc)₂ (45.3 mg, 0.25 mmol) in CH₂Cl₂ (13.0 mL) and MeOH (2.0 mL) was stirred at RT open to air for 4 hours. The mixture was poured into 1.0 N aqueous HCl (100 mL) and extracted with CH₂Cl₂. The CH₂Cl₂ layer was dried over Na₂SO₄ and concentrated. The crude product was purified by prep-HPLC (C18 column/Water:MeOH:TFA 90:10:0.1 to 10:90:0.1 gradient) giving the title compound 5-(4-chlorobenzylthio)-2-(4-(2-hydroxy-2-methylpropoxy)-3-methoxyphenyl)pyridazin-3(2H)-one F-1 (23 mg, 61% yield) as white solid. LC/MS 447 (M+H)⁺, $t_R$ 4.14 min (method 3); $^1$H NMR (500 MHz, Chloroform-D) δ ppm 7.65 (1H, d, J=2.20 Hz), 7.35 (4H, s), 7.07-7.13 (2H, m), 6.96 (1H, d, J=8.80 Hz), 6.66 (1H, d, J=2.20 Hz), 4.15 (2H, s), 3.81-3.91 (5H, m), 1.35 (6H, s).

Procedure 10

Example G-1

6-((4-Chlorophenylthio)methyl)-3-(4-(2-hydroxy-2-methylpropoxy)-3-methoxyphenyl)pyrimidin-4(3H)-one

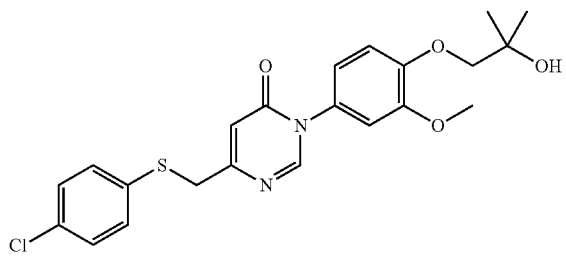

A. Ethyl 4-(4-chlorophenylthio)-3-oxobutanoate

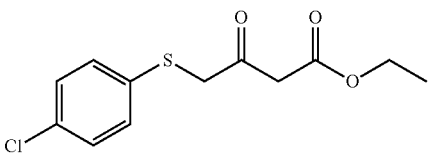

To a mixture of 4-chlorobenzenethiol (1.75 g, 12.15 mmol) and K₂CO₃ (3.36 g, 24.30 mmol) in DMF (40 mL) was added ethyl 4-chloro-3-oxobutanoate (2.0 g, 12.15 mmol). The mixture was stirred at RT for 18 hours, diluted with saturated NaHCO₃ (40 mL) and extracted with EtOAc (50 mL). The EtOAc layer was dried over Na₂SO₄ and concentrated. The crude product was purified by flash chromatography (silica gel/hexane-EtOAc 100:0 to 0:100 gradient, using LC-MS to identify fractions containing the desired product) to afford ethyl 4-(4-chlorophenylthio)-3-oxobutanoate 10A (2.07 g, 59% yield). $^1$H NMR (500 MHz, Chloroform-D) δ ppm 7.22-7.32 (4H, m), 4.18 (2H, q, J=7.15 Hz), 3.79 (2H, s), 3.62 (2H, s), 1.27 (3H, t, J=7.01 Hz).

B. 6-((4-Chlorophenylthio)methyl)pyrimidin-4(3H)-one

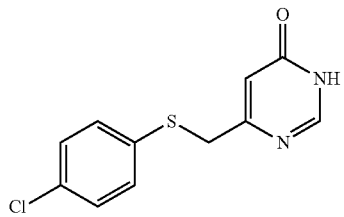

A mixture of formamidine acetate (1508 mg, 14.48 mmol), ethyl 4-(4-chlorophenylthio)-3-oxobutanoate Part A (790 mg, 2.90 mmol) and phenol (8178 mg, 87 mmol) was stirred at 140° C. for 18 hours. After the reaction cooled to RT, the mixture was diluted with saturated NaHCO₃ (65 mL) and extracted with EtOAc (80 mL). The EtOAc layer was dried over Na₂SO₄ and concentrated. The crude product was purified by flash chromatography (silica gel/hexane-EtOAc 100:0 to 0:100 gradient, using LC-MS to identify fractions containing the desired product) to afford 6-((4-chlorophenylthio)methyl)pyrimidin-4(3H)-one 10B (169 mg, 22% yield). $^1$H NMR (400 MHz, CD$_3$OD) δ ppm 7.97 (1H, s), 7.07-7.25 (4H, m), 6.06 (1H, s), 3.80 (2H, s).

C. 6-((4-Chlorophenylthio)methyl)-3-(4-(2-hydroxy-2-methylpropoxy)-3-methoxyphenyl)pyrimidin-4(3H)-one

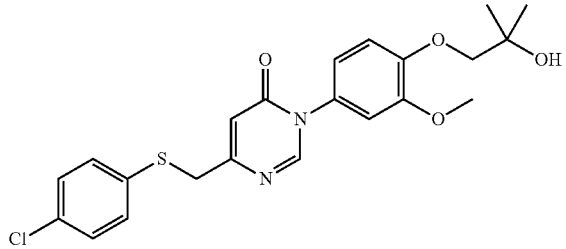

A mixture of 6-((4-chlorophenylthio)methyl)pyrimidin-4(3H)-one Part B (25 mg, 0.10 mmol), 1-(4-bromo-2-methoxyphenoxy)-2-methylpropan-2-ol Part B of Procedure 1 (32.7 mg, 0.12 mmol), N1,N2-dimethylethane-1,2-diamine (26.2 mg, 0.30 mmol), potassium phosphate tribasic (63.0 mg, 0.30 mmol) and copper (I) iodide (18.84 mg, 0.10 mmol) in dioxane (4.0 mL) was stirred in a sealed tube at 110° C. for 60 min. After the mixture had cooled to RT, the precipitate removed by filtration and the filtrate was concentrated. The crude product was purified by flash chromatography (silica gel/CH$_2$Cl$_2$-10% MeOH/CH$_2$Cl$_2$ 100:0 to 0:100 gradient, using LC-MS to identify fractions containing the desired product). The pure fractions were lyophilized with MeCN/H$_2$O (1:1, 4 mL) to afford the title compound 6-((4-chlorophenylthio)methyl)-3-(4-(2-hydroxy-2-methylpropoxy)-3-methoxyphenyl)pyrimidin-4(3H)-one G-1 as an off-white solid (1.40 mg, 3.01% yield). LC/MS 447 (M+H)$^+$, t$_R$ 0.92 min (method 5); $^1$H NMR (500 MHz, Chloroform-D) δ ppm 8.14 (1H, br. s.), 7.27-7.36 (4H, m), 6.99 (1H, d, J=8.25 Hz), 6.79-6.88 (2H, m), 6.45 (1H, s), 3.96 (2H, s), 3.82-3.90 (5H, m), 1.36 (6H, s).

Procedure 11

Example H-1

6-(4-Chlorobenzyloxy)-3-(4-(2-hydroxy-2-methylpropoxy)-3-methoxyphenyl)pyrimidin-4(3H)-one

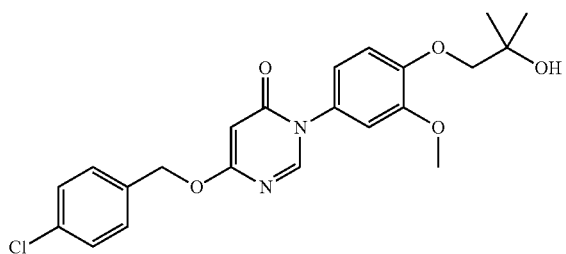

A. 6-Chloro-3-(4-(2-hydroxy-2-methylpropoxy)-3-methoxyphenyl)pyrimidin-4(3H)-one

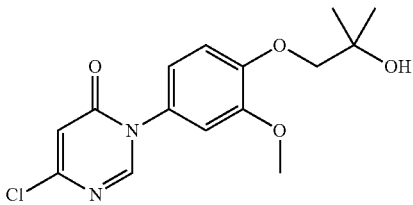

A mixture of 6-chloropyrimidin-4(3H)-one (50 mg, 0.383 mmol), 4-(2-hydroxy-2-methylpropoxy)-3-methoxyphenylboronic acid Part D of Procedure 4 (184 mg, 0.766 mmol), copper (II) acetate, monohydrate (84 mg, 0.421 mmol), and pyridine (1.5 mL, 19.15 mmol) in DCM (4 mL) was stirred at RT under the presence of air overnight (21 hours). Pyridine (0.5 mL) and MeOH (0.5 mL) were added and continued to stir for 2 hours. The reaction was diluted with DCM, washed with 1N HCl, sat NaHCO$_3$, dried (Na$_2$SO$_4$), and concentrated to afford crude product. The crude was purified using ISCO flash chromatography (silica gel/hexanes-ethyl acetate 100:0 to 0:100 gradient) to afford the desired product 6-chloro-3-(4-(2-hydroxy-2-methylpropoxy)-3-methoxyphenyl)-pyrimidin-4(3H)-one 11A (57.4 mg, 0.177 mmol, 46% yield) as a light brown solid.

B. 6-(4-Chlorobenzyloxy)-3-(4-(2-hydroxy-2-methylpropoxy)-3-methoxyphenyl)pyrimidin-4(3H)-one

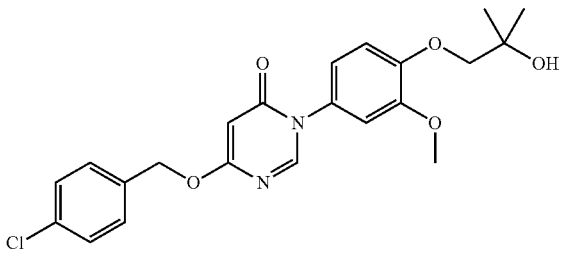

Sodium hydride (13 mg, 0.32 mmol) was added to a solution of (4-chlorophenyl)methanol (46 mg, 0.32 mmol) in THF (1 mL) under nitrogen. The mixture was stirred at RT for 1 hour, then 6-chloro-3-(4-(2-hydroxy-2-methylpropoxy)-3-methoxyphenyl)pyrimidin-4(3H)-one Part A (35 mg, 0.108 mmol) was added and stirred for 45 min at RT. The reaction was quenched with MeOH (0.5 mL), diluted with EtOAc, washed with saturated NH$_4$Cl, dried (Na$_2$SO$_4$), and concentrated. The residue was subjected to ISCO flash chromatography (silica gel/hexane-EtOAc 100:0 to 0:100 gradient). The product was then re-purified using HPLC (C18 column/10:90 to 90:10 MeOH—H$_2$O) to afford the title compound 6-(4-chlorobenzyloxy)-3-(4-(2-hydroxy-2-methyl-propoxy)-3-methoxyphenyl)pyrimidin-4(3H)-one H-1 (2.5 mg, 5.2% yield). LC/MS 431 (M+H)$^+$, t$_R$ 0.91 min (method 5); $^1$H NMR (400 MHz, chloroform-d) δ 6.04 (1H, s), 7.38 (4H, s), 7.00

(1H, d), 6.79-6.89 (2H, m), 5.85 (1H, s), 5.27 (2H, s), 3.87 (3H, s), 3.86 (2H, s), 1.36 (6H, s).

Procedure 12

Example J-1

(E)-6-(4-Chlorostyryl)-3-(4-(2-hydroxy-2-methyl-propoxy)-3-methoxyphenyl)pyrimidin-4(3H)-one

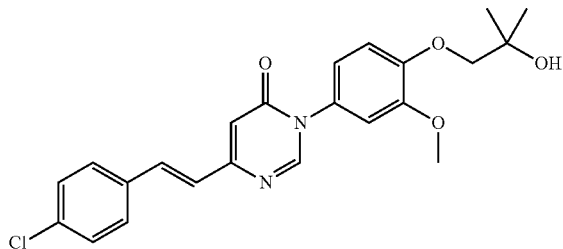

A mixture of 6-chloro-3-(4-(2-hydroxy-2-methylpropoxy)-3-methoxyphenyl)pyrimidin-4(3H)-one Part A of Procedure 11 (40 mg, 0.12 mmol), (E)-4-chlorostyrylboronic acid (56 mg, 0.30 mmol), potassium phosphate, tribasic (78 mg, 0.37 mmol), and palladiumtetrakis (7 mg, 6.16 µmol) in DMF (1 mL) was stirred under nitrogen at 55° C. for 1 hour. The mixture was diluted with DCM, washed with water, sat. NaHCO$_3$ and brine, then dried (Na$_2$SO$_4$) and concentrated to afford the crude product. The crude product was purified using ISCO flash chromatography (silica gel/hexanes-ethyl acetate 100:0 to 0:100 gradient). The product was re-purified using HPLC (C18 column/10:90 to 90:10 MeOH—H$_2$O) to afford the desired product (E)-6-(4-chlorostyryl)-3-(4-(2-hydroxy-2-methylpropoxy)-3-methoxyphenyl)pyrimidin-4(3H)-one J-1 (16.8 mg, 0.039 mmol, 31% yield) as a light yellow solid. LC/MS 427 (M+H)$^+$, $t_R$ 0.97 min (method 5); $^1$H NMR (400 MHz, CHLOROFORM-d) δ 8.15 (1H, s), 7.76 (1H, d, J=15.56 Hz), 7.53 (2H, d, J=8.28 Hz), 7.38 (2H, d, J=8.28 Hz), 7.01 (1H, d, J=8.03 Hz), 6.82-6.98 (3H, m), 6.46 (1H, s), 3.89 (5H, br. s.), 1.37 (6H, s).

Procedure 13

Example J-2

6-((4-Chlorophenyl)ethynyl)-3-(4-(2-hydroxy-2-methylpropoxy)-3-methoxyphenyl)pyrimidin-4(3H)-one

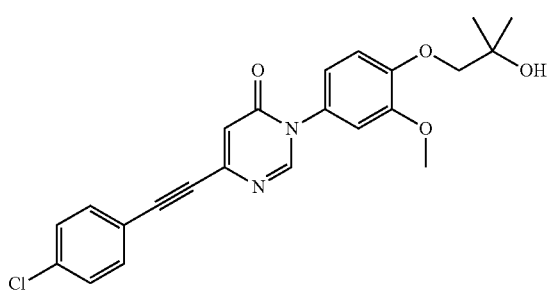

A mixture of 6-chloro-3-(4-(2-hydroxy-2-methylpropoxy)-3-methoxyphenyl)pyrimidin-4(3H)-one Part A of Procedure 11 (30 mg, 0.092 mmol), tributyl((4-chlorophenyl)ethynyl)stannane (79 mg, 0.185 mmol), copper (I) iodide (5.28 mg, 0.028 mmol), and palladiumtetrakis (16 mg, 0.014 mmol) in DMF (1 mL) was stirred under nitrogen at 55° C. for 3 hours. The reaction was cooled to RT, diluted with CH$_2$Cl$_2$, washed with water, sat. NaHCO$_3$, dried (Na$_2$SO$_4$), and concentrated to afford the crude product. The residue was purified using ISCO flash chromatography (silica gel/hexanes-ethyl acetate 100:0 to 0:100 gradient). The product was re-purified using HPLC (C18 column/10:90 to 90:10 MeOH—H$_2$O) to afford the desired product 6-((4-chlorophenyl)ethynyl)-3-(4-(2-hydroxy-2-methylpropoxy)-3-methoxyphenyl)pyrimidin-4(3H)-one J-2 (12.4 mg, 0.028 mmol, 30.0% yield) as a yellow solid. LC/MS 425 (M+H)$^+$, $t_R$ 0.95 min (method 5); $^1$H NMR (400 MHz, CDCl$_3$) δ 8.14-8.17 (1H, m), 7.55 (2H, d), 7.39 (2H, d), 7.01 (1H, d), 6.85-6.93 (2H, m), 6.75 (1H, s), 3.89 (3H, s), 3.88 (2H, s), 1.37 (6H, s).

Procedure 14

Example K-1

3-(4-(2-Hydroxy-2-methylpropoxy)-3-methoxyphenyl)-6-(2-phenylcyclopropyl)pyrimidin-4(3H)-one

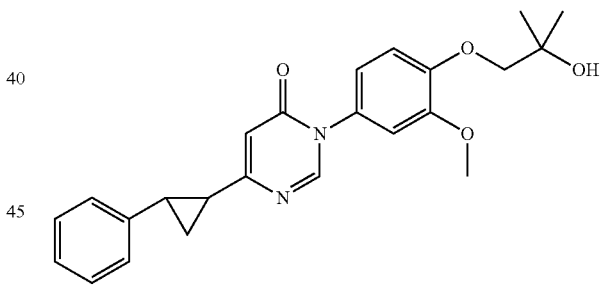

Tricyclohexyl phosphine (10 µL, 9.24 µmol) was added under nitrogen to a mixture of 6-chloro-3-(4-(2-hydroxy-2-methylpropoxy)-3-methoxyphenyl)-pyrimidin-4(3H)-one Part A of Procedure 11 (10 mg, 0.031 mmol), 2-phenylcyclopropylboronic acid (5.5 mg, 0.034 mmol), palladium (II) acetate (2 mg, 6.16 µmol), and potassium phosphate, tribasic (20 mg, 0.09 mmol) in toluene (0.16 mL), and water (0.07 mL). The reaction stirred at 100° C. for 2 hours. The reaction mixture was filtered and concentrated to afford the crude product. The crude was purified using HPLC (C18 column/10:90:0.1 to 90:10:0.1 MeOH—H$_2$O-TFA) to afford the desired product 3-(4-(2-hydroxy-2-methylpropoxy)-3-methoxyphenyl)-6-(2-phenylcyclopropyl)pyrimidin-4(3H)-one K-1 (3 mg, 7.23 µmol, 23.49% yield) as a light yellow solid. LC/MS 407 (M+H)$^+$, $t_R$ 0.92 min (method 5); $^1$H NMR (400 MHz, CHLOROFORM-d) δ 8.11 (1H, s), 7.28-7.41 (2H, m), 7.20-7.26 (1H, m), 7.13-7.19 (2H, m), 7.00 (1H, d), 6.85-6.90

(2H, m), 6.48 (1H, s), 3.88 (5H, br. s.), 2.60-2.66 (1H, m), 2.08-2.14 (1H, m), 1.75-1.81 (1H, m), 1.51-1.57 (1H, m), 1.37 (6H, s).

Procedure 15

Example D-8

5-(2-(4-Chlorophenyl)cyclopropyl)-2-(4-(2-hydroxy-2-methylpropoxy)-3-methoxyphenyl)pyridazin-3(2H)-one

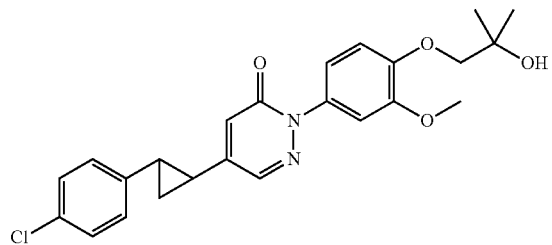

A. 5-(2-(4-Chlorophenyl)cyclopropyl)pyridazin-3(2H)-one

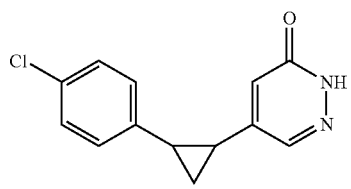

To a mixture of 2-(2-(4-chlorophenyl)cyclopropyl)-6-methyl-1,3,6,2-dioxazaborocane-4,8-dione (95 mg, 0.310 mmol), tert-butyl 4-iodo-6-oxopyridazine-1(6H)-carboxylate (100 mg, 0.310 mmol), potassium phosphate tribasic (330 mg, 1.552 mmol), and 30% wt tricyclohexyl phosphine in toluene (29.0 mg, 0.031 mmol) in toluene (4.0 mL) and water (0.200 mL) under nitrogen was added palladium(II) acetate (3.49 mg, 0.016 mmol). After the mixture had stirred at 100° C. for 18 hours, the precipitate was removed by filtration prior to removal of the volatiles under vacuum. The crude product was purified by prep-HPLC (Phenomenex, Luna 5 micron 30×250 mm, flow rate=30 ml/min., gradient=20% A to 100% B in 30 min., A=H$_2$O/MeOH/TFA (90:10:0.1), B=H$_2$O/MeOH/TFA (10:90:0.1)) to afford 5-(2-(4-chlorophenyl)cyclopropyl)pyridazin-3(2H)-one 15A (9.5 mg, 12.16% yield) as off-white solid. LC/MS 247 (M+H)$^+$, t$_R$ 0.83 min (method 5). $^1$H NMR (400 MHz, CHLOROFORM-d) δ ppm 11.13 (1H, br. s.), 7.65 (1H, d, J=2.01 Hz), 7.29 (2H, d, J=8.53 Hz), 7.06 (2H, d, J=8.53 Hz), 6.56 (1H, d, J=1.51 Hz), 2.19-2.34 (1H, m), 1.86-2.02 (1H, m), 1.47-1.69 (2H, m).

B. 5-(2-(4-Chlorophenyl)cyclopropyl)-2-(4-(2-hydroxy-2-methylpropoxy)-3-methoxyphenyl)pyridazin-3(2H)-one

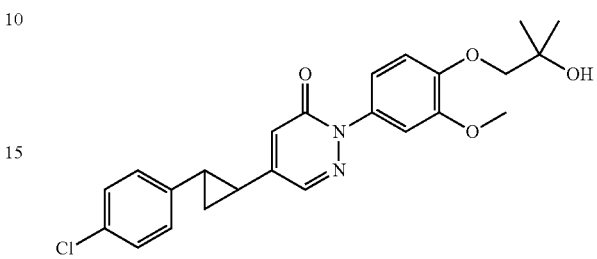

A mixture of potassium phosphate tribasic (24.52 mg, 0.116 mmol), N1,N2-dimethylcyclohexane-1,2-diamine (5.48 mg, 0.039 mmol), copper(I) iodide (7.33 mg, 0.039 mmol), 1-(4-bromo-2-methoxyphenoxy)-2-methylpropan-2-ol Part B of Procedure 1 (12.71 mg, 0.046 mmol) and 5-(2-(4-chlorophenyl)cyclopropyl)pyridazin-3(2H)-one Part A (9.5 mg, 0.039 mmol) in dioxane (30 mL) was stirred in a seal tube at 110° C. for 1 hours. After removal of the precipitate by filtration, the reaction was concentrated under vacuum. The crude product was purified by prep-HPLC (Phenomenex Axia, Luna 5 micron 30×100 mm, flow rate=40 ml/min., gradient=0% A to 100% B in 10 min., A=H$_2$O/MeOH/TFA (90:10:0.1), B=H$_2$O/MeOH/TFA (10:90:0.1)) to afford the title compound 5-(2-(4-chlorophenyl)cyclopropyl)-2-(4-(2-hydroxy-2-methylpropoxy)-3-methoxyphenyl)pyridazin-3(2H)-one D-8 (8.80 mg, 51.8% yield) as off white powder. LC/MS 441 (M+H)$^+$, t$_R$ 0.98 min (method 5). 1H NMR (400 MHz, CHLOROFORM-d) δ ppm 7.78 (1H, d, J=2.26 Hz), 7.30 (2H, d, J=8.53 Hz), 7.05-7.16 (4H, m), 6.97 (1H, d, J=9.03 Hz), 6.72 (1H, d, J=2.26 Hz), 3.87 (5H, d, J=2.26 Hz), 2.33 (1H, ddd, J=8.91, 6.15, 4.52 Hz), 1.91-2.08 (1H, m), 1.53-1.71 (2H, m), 1.35 (6H, s).

Procedure 16

Example G-2

6-((4-Chlorophenylthio)methyl)-3-(4-(2-cyclopropyl-2-hydroxyethoxy)-3-methoxyphenyl)pyrimidin-4(3H)-one

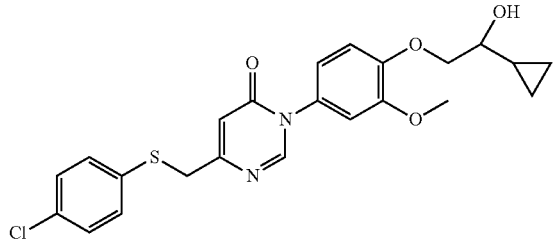

A. 2-(4-Bromo-2-methoxyphenoxy)-N-methoxy-N-methylacetamide

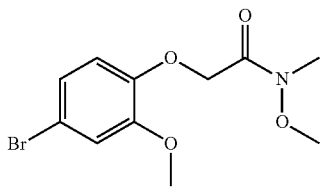

A mixture of 2-chloro-N-methoxy-N-methylacetamide (2.7 g, 19.63 mmol), 4-bromo-2-methoxyphenol (3.98 g, 19.63 mmol), and potassium carbonate (5.43 g, 39.3 mmol) in DMF (20 mL) was heated at 60° C. for 1 hour and stirred at RT overnight (16 hours). The reaction mixture was diluted with $CH_2Cl_2$, washed with sat $NaHCO_3$, brine and dried ($Na_2SO_4$). After concentration, the crude product was purified by ISCO flash chromatography (silica gel/hexanes-ethyl acetate 100:0 to 0:100 gradient) to afford 2-(4-bromo-2-methoxyphenoxy)-N-methoxy-N-methylacetamide 16A (4.86 g, 15.98 mmol, 81% yield) as a yellow solid. $^1$H NMR (400 MHz, chloroform-d) δ 6.97-7.04 (2H, m), 6.76 (1H, d, J=8.03 Hz), 4.86 (2H, s), 3.87 (3H, s), 3.75 (3H, s), 3.23 (3H, s).

B. 2-(4-Bromo-2-methoxyphenoxy)-1-cyclopropylethanone

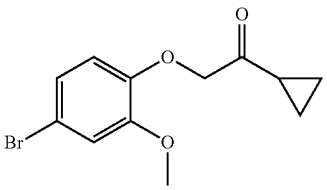

To a solution of 2-(4-bromo-2-methoxyphenoxy)-N-methoxy-N-methylacetamide Part A (2 g, 6.58 mmol) in THF (25 mL) was slowly added cyclopropylmagnesium bromide (39.5 mL, 19.73 mmol). After stirring for 1 hour at RT, the reaction mixture was added to a sat. $NH_4Cl$ solution which was subsequently extracted with EtOAc, dried ($Na_2SO_4$), and concentrated. The crude product was purified using ISCO flash chromatography (silica gel/hexanes-ethyl acetate 100:0 to 50:50 gradient) to afford the desired product 2-(4-bromo-2-methoxyphenoxy)-1-cyclopropylethanone 16B (1.72 g, 6.03 mmol, 92% yield) as a yellow oil. $^1$H NMR (400 MHz, chloroform-d) δ 7.01 (2H, dddd), 6.65 (1H, d, J=8.53 Hz), 4.72 (2H, s), 3.89 (3H, s), 2.24-2.35 (1H, m), 1.15 (2H, quin, J=3.83 Hz), 0.98 (2H, dq, J=7.56, 3.67 Hz).

C. 2-(4-Bromo-2-methoxyphenoxy)-1-cyclopropylethanol

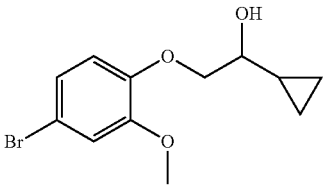

To a solution of 2-(4-bromo-2-methoxyphenoxy)-1-cyclopropylethanone Part B (1.7 g, 5.96 mmol) in THF (12 mL) and MeOH (12 mL) was slowly added sodium borohydride (0.226 g, 5.96 mmol). After stirring at RT for 30 min, the mixture was concentrated, diluted with EtOAc, washed with sat $NaHCO_3$, 1N HCl, brine, dried ($Na_2SO_4$) and concentrated. The crude product was purified using ISCO flash chromatography (silica gel/hexanes-ethyl acetate 100:0 to 50:50 gradient) to afford the desired product 2-(4-bromo-2-methoxyphenoxy)-1-cyclopropylethanol 16C (1.53 g, 5.33 mmol, 89% yield) as a clear oil. $^1$H NMR (400 MHz, chloroform-d) δ 6.97-7.07 (2H, m), 6.81 (1H, d, J=8.53 Hz), 4.14 (1H, dd, J=9.79, 2.76 Hz), 3.90-3.98 (1H, m), 3.85 (3H, s), 3.31 (1H, t, J=2.51 Hz), 2.78 (1H, s), 0.88-1.01 (1H, m), 0.49-0.67 (2H, m), 0.44 (1H, dd, J=9.41, 4.64 Hz), 0.25-0.33 (1H, m).

D. 6-((4-Chlorophenylthio)methyl)-3-(4-(2-cyclopropyl-2-hydroxyethoxy)-3-methoxyphenyl)pyrimidin-4(3H)-one

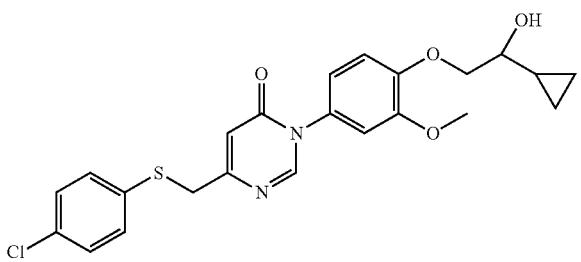

N-arylation of 6-((4-chlorophenylthio)methyl)pyrimidin-4(3H)-one Part B of Procedure 10 with 2-(4-bromo-2-methoxyphenoxy)-1-cyclopropylethanol Part C to generate G-2 was achieved using the procedure described in Part C of Procedure 10. LC/MS 459 (M+H)$^+$, $t_R$ 0.97 min (method 5). $^1$H NMR (400 MHz, Chloroform-D) δ ppm 8.14 (1H, s), 7.26-7.40 (4H, m), 7.03 (1H, d), 6.80-6.91 (2H, m), 6.45 (1H, s), 4.20 (1H, dd, J=9.54, 2.76 Hz), 4.03 (1H, t, J=8.91 Hz), 3.96 (2H, s), 3.87 (3H, s), 3.36 (1H, td, J=8.34, 2.64 Hz), 0.91-1.06 (1H, m), 0.51-0.67 (2H, m), 0.40-0.50 (1H, m), 0.26-0.37 (1H, m).

Procedure 17

Example H-3

6-(4-fluorobenzylthio)-3-(4-(2-hydroxy-2-methylpropoxy)-3-methoxyphenyl)pyrimidin-4(3H)-one

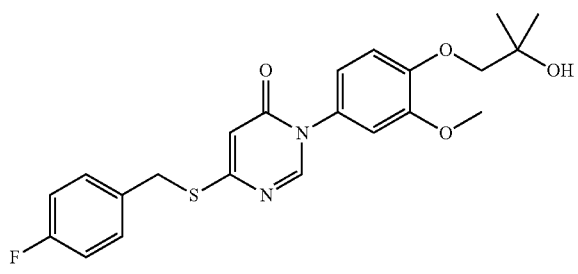

A mixture of 6-chloro-3-(4-(2-hydroxy-2-methylpropoxy)-3-methoxyphenyl)pyrimidin-4(3H)-one Part A of procedure 11 (20 mg, 0.06 mmol), (4-fluorophenyl)methanethiol (26 mg, 0.18 mmol), and potassium carbonate (25.5 mg, 0.185 mmol) in THF (0.5 mL) was stirred at 70° C. overnight. The reaction was diluted with $CH_2Cl_2$, filtered, and concentrated. The crude product was purified using HPLC (Phen Luna Axia C18 5μ 10:90:0.1 to 90:10:0.1 MeOH—H₂O-TFA) to afford the desired product 6-(4-fluorobenzylthio)-3-(4-(2-hydroxy-2-methylpropoxy)-3-methoxyphenyl)pyrimidin-4(3H)-one H-3 (17.25 mg, 0.038 mmol, 61.8% yield) as off-white solid. LC/MS 431 (M+H)⁺, $t_R$ 0.91 min (method 5). ¹H NMR (400 MHz, CHLOROFORM-d) δ ppm 8.14 (1H, s), 7.35-7.45 (2H, m), 6.95-7.09 (3H, m), 6.80-6.90 (2H, m), 6.49 (1H, s), 4.28 (2H, s), 3.88 (5H, s), 1.39 (6H, s)

Procedure 18

Example L-1

2-(4-(2-hydroxy-2-methylpropoxy)-3-methoxyphenyl)-5-(4-(trifluoromethyl)phenyl)pyridazin-3(2H)-one

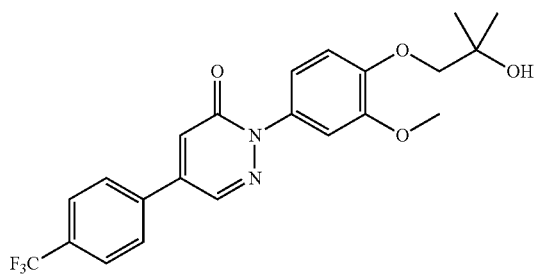

A. 5-(4-(trifluoromethyl)phenyl)pyridazin-3(2H)-one

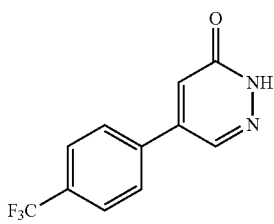

Tricyclohexyl phosphine (16.6 μL, 0.02 mmol) was added to a mixture of 5-iodopyridazin-3(2H)-one (35 mg, 0.16 mmol), 4-(trifluoromethyl)phenylboronic acid (30 mg, 0.16 mmol), potassium phosphate tribasic (117 mg, 0.55 mmol), and palladium (II) acetate (3.5 mg, 0.02 mmol) in Toluene (0.8 mL) and Water (0.3 mL). The mixture was stirred at 100° C. for 22 hours. The reaction was diluted with CH₂Cl₂, filtered and concentrated. The crude was purified using HPLC (Phen Luna Axia C18 5μ 10:90:0.1 to 90:10:0.1 MeOH—H₂O-TFA) to afford the desired product 5-(4-(trifluoromethyl)phenyl)pyridazin-3(2H)-one 18A (14.8 mg, 0.06 mmol, 39.1% yield) as a white solid. LC/MS 282 (M+H)⁺, $t_R$ 0.77 min (method 5).

B. 2-(4-(2-hydroxy-2-methylpropoxy)-3-methoxyphenyl)-5-(4-(trifluoromethyl)phenyl)pyridazin-3(2H)-one

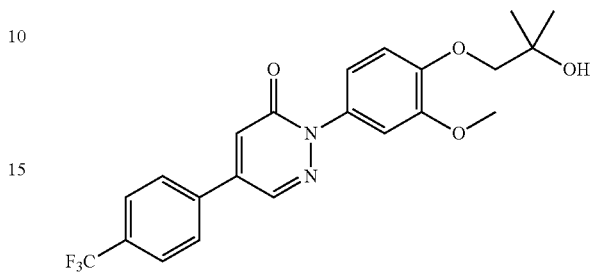

N1,N2-dimethylethane-1,2-diamine (10 μL, 0.09 mmol) was added to a mixture of 5-(4-(trifluoromethyl)phenyl)pyridazin-3(2H)-one Part A (15 mg, 0.06 mmol), 1-(4-bromo-2-methoxyphenoxy)-2-methylpropan-2-ol Part B of Procedure 1 (20.6 mg, 0.08 mmol), potassium phosphate tribasic (39.8 mg, 0.19 mmol), and copper (I) iodide (17.8 mg, 0.09 mmol) in DMF (0.8 mL). After stirring at 110° C. overnight, the reaction mixture was diluted with CH₂Cl₂, filtered, washed with sat NaHCO₃, brine, dried (MgSO₄), and concentrated. The crude product was purified using HPLC (Phen Luna Axia C18 5μ 10:90:0.1 to 90:10:0.1 MeOH—H₂O-TFA) to afford the desired product 2-(4-(2-hydroxy-2-methylpropoxy)-3-methoxyphenyl)-5-(4-(trifluoromethyl)-phenyl)pyridazin-3(2H)-one L-1 (11.7 mg, 0.03 mmol, 41.0% yield) as a yellow solid. LC/MS 435 (M+H)⁺, $t_R$ 0.94 min (method 5). ¹H NMR (400 MHz, CHLOROFORM-d) δ ppm 8.20 (1H, d, J=2.01 Hz), 7.73-7.87 (4H, m), 7.17-7.26 (3H, m), 7.02 (1H, d, J=8.28 Hz), 3.91 (3H, s), 3.89 (2H, s), 1.38 (6H, s)

Procedure 19

Example M-1

6-(4-ethylphenyl)-3-(4-(2-hydroxy-2-methylpropoxy)-3-methoxyphenyl)pyrimidin-4(3H)-one

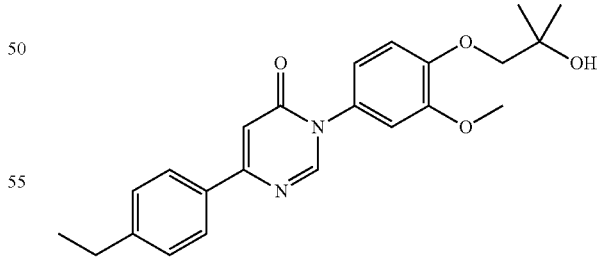

A mixture of 6-chloro-3-(4-(2-hydroxy-2-methylpropoxy)-3-methoxyphenyl)-pyrimidin-4(3H)-one Part A of Procedure 11 (11 mg, 0.03 mmol), 4-ethylphenylboronic acid (7.6 mg, 0.05 mmol), potassium phosphate tribasic (21.57 mg, 0.102 mmol), and PalladiumTetrakis (4 mg, 3.39 μmol) in DMF (0.5 mL) was stirred at 90° C. overnight. The reaction was diluted with CH₂Cl₂, filtered, and concentrated. The crude was purified using HPLC (Phen Luna Axia C18 5μ

10:90:0.1 to 90:10:0.1 MeOH—H$_2$O-TFA) to afford the desired product 6-(4-ethylphenyl)-3-(4-(2-hydroxy-2-methylpropoxy)-3-methoxyphenyl)pyrimidin-4(3H)-one M-1 (9.93 mg, 0.02 mmol, 69.1% yield) as a light yellow solid. LC/MS 395 (M+H)$^+$, t$_R$ 0.95 min (method 5). $^1$H NMR (500 MHz, CHLOROFORM-d) d ppm 8.25 (1H, s), 7.93 (2H, d, J=8.32 Hz), 7.34 (2H, d, J=8.32 Hz), 7.02 (1H, d), 6.91-6.96 (3H, m), 3.90 (3H, s), 3.89 (2H, s), 2.74 (2H, q), 1.38 (6H, s), 1.30 (3H, t, J=7.63 Hz)

Procedure 20

Example J-3

(E)-6-(4-chlorostyryl)-3-(4-((3,3-difluoro-1-hydroxycyclobutyl)methoxy)-3-methoxyphenyl)pyrimidin-4(3H)-one

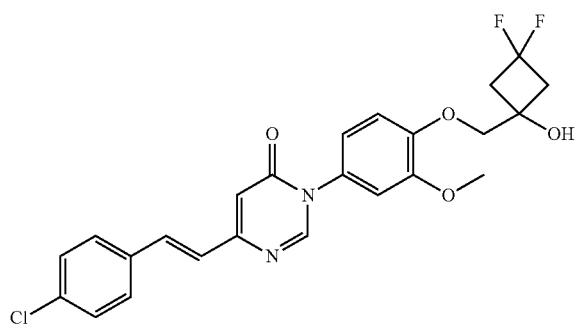

A. (E)-4-chloro-6-(4-chlorostyryl)pyrimidine

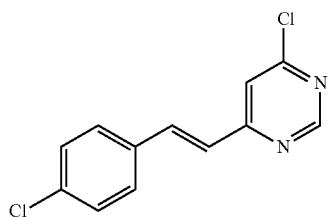

A mixture of commercially available 4,6-dichloropyrimidine (300 mg, 2.01 mmol), (E)-4-chlorostyrylboronic acid (441 mg, 2.41 mmol), potassium phosphate (1282 mg, 6.04 mmol), and PalladiumTetrakis (116 mg, 0.10 mmol) in DMF (1 mL) was stirred under nitrogen at 40° C. for 2 days. The reaction was filtered, diluted with CH$_2$Cl$_2$, washed with water, brine, dried (MgSO$_4$), and concentrated. The crude product was purified using ISCO flash chromatography (silica gel/hexanes/ethyl acetate 100:0 to 50:50 gradient) to afford the desired product (E)-4-chloro-6-(4-chlorostyryl)pyrimidine 20A (120 mg, 0.49 mmol, 23.73% yield) as a light yellow solid. LC/MS 252 (M+H)$^+$, t$_R$ 1.07 min (method 5).

B. (E)-6-(4-chlorostyryl)pyrimidin-4(3H)-one

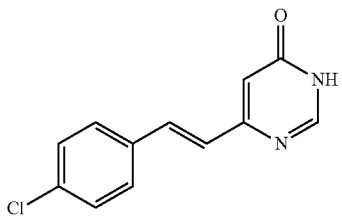

A mixture of (E)-4-chloro-6-(4-chlorostyryl)pyrimidine Part A (120 mg, 0.48 mmol), DABCO (107 mg, 0.96 mmol), and potassium carbonate (660 mg, 4.78 mmol) in Dioxane (0.4 mL) and Water (4 mL) was stirred at 60° C. overnight. The reaction was cooled to RT, acidified with 10% HCl, extracted with EtOAC, dried (Na$_2$SO$_4$), and concentrated. The product was triturated with DCM to afford the desired product (E)-6-(4-chlorostyryl)pyrimidin-4(3H)-one 20B (108 mg, 0.46 mmol, 97% yield) as a light yellow solid.

C. (E)-6-(4-chlorostyryl)-3-(4-((3,3-difluoro-1-hydroxycyclobutyl)methoxy)-3-methoxyphenyl)pyrimidin-4(3H)-one

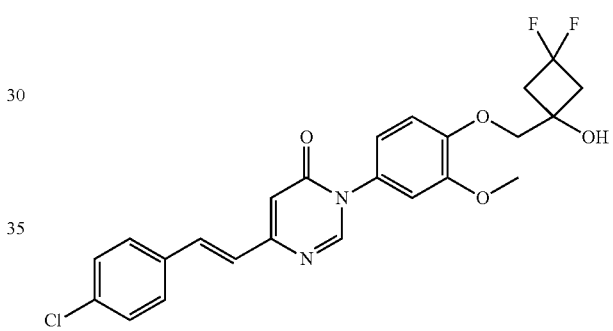

N1,N2-dimethylethane-1,2-diamine (12 nL, 0.11 mmol) was added to a mixture of (E)-6-(4-chlorostyryl)pyrimidin-4(3H)-one Part B (25 mg, 0.11 mmol), 1-((4-bromo-2-methoxyphenoxy)methyl)-3,3-difluorocyclobutanol (38 mg, 0.12 mmol), potassium phosphate tribasic (68.4 mg, 0.322 mmol), and copper (I) iodide (20.5 mg, 0.11 mmol) in DMF (1 mL) and stirred at 100° C. overnight. The reaction was filtered and concentrated. The residue was purified using HPLC (Phen Luna Axia C18 5μ 10:90:0.1 to 90:10:0.1 MeOH—H$_2$O-TFA) to afford the desired product (E)-6-(4-chlorostyryl)-3-(4-((3,3-difluoro-1-hydroxycyclobutyl)methoxy)-3-methoxyphenyl)pyrimidin-4(3H)-one J-3 (5.69 mg, 0.01 mmol, 10.93% yield) as a brown solid. LC/MS 475 (M+H)$^+$, t$_R$ 1.00 min (method 5). $^1$H NMR (400 MHz, CHLOROFORM-d) δ ppm 8.17 (1H, s), 7.76 (1H, d), 7.53 (2H, d), 7.40 (2H, d), 7.08 (1H, d), 6.86-6.97 (3H, m), 6.48 (1H, s), 4.13 (2H, s), 3.89 (3H, s), 2.77-2.87 (4H, m)

Prodrug Examples P-1 to P-4

Prodrugs were prepared of selected secondary and tertiary alcohols to improve solubility and exposure. Preparation of the glycine ester of the tertiary alcohols is exemplified below. Examples P-2-P-4 were prepared in a similar manner to that described for P-1 using the appropriate alcohol and BOC glycine followed by TFA removal of the BOC group.

TABLE P

Prodrug Esters

| Ex. No. | Ester of Ex. No. | Structure | HPLC (Met1) | LC MS | $^1$H-NMR (CDCl$_3$) |
|---|---|---|---|---|---|
| P-1 | H-2 | 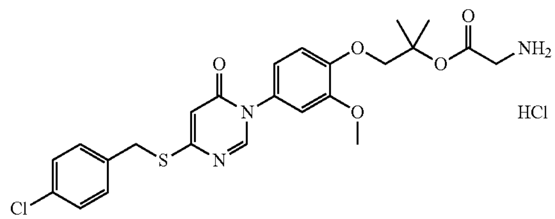 | 0.85; method 5 | 504 | $^1$H NMR (400 MHz, MeOD) δ 8.28 (1 H, s), 7.45 (2 H, d), 7.33 (2 H, d), 7.05-7.12 (2 H, m), 6.93 (1 H, dd), 6.37 (1 H, s), 4.37 (2 H, s), 4.29 (2 H, s), 3.86 (3 H, s), 3.69 (2 H, s), 1.64 (6 H, s) |
| P-2 | J-2 | 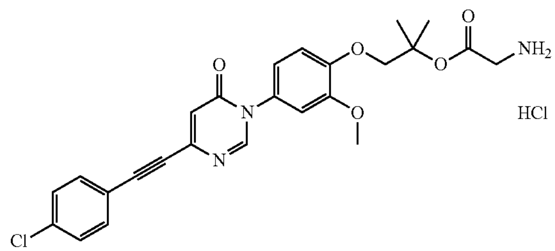 | 0.84; method 5 | 482 | $^1$H NMR (400 MHz, MeOD) δ 8.41 (1 H, s), 7.62 (2 H, d), 7.48 (2 H, d), 7.09-7.17 (2 H, m), 6.96-7.02 (1 H, m), 6.79 (1 H, s), 4.30 (2 H, s), 3.88 (3 H, s), 3.72 (2 H, s), 1.65 (6 H, s) |
| P-3 | J-1 | 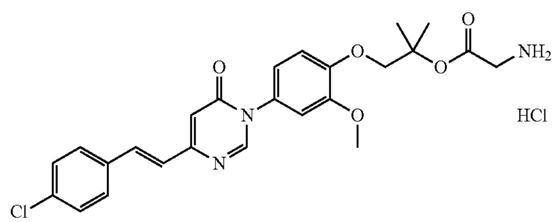 | 0.86; method 5 | 484 | $^1$H NMR (400 MHz, MeOD) δ 8.44 (1 H, s), 7.82 (1 H, d), 7.64 (2 H, d), 7.43 (2 H, d), 7.09-7.18 (3 H, m), 6.98 (1 H, d), 6.58 (1 H, s), 4.30 (2 H, s), 3.88 (3 H, s), 3.72 (2 H, s), 1.66 (6 H, s) |
| P-4 | F-4 | 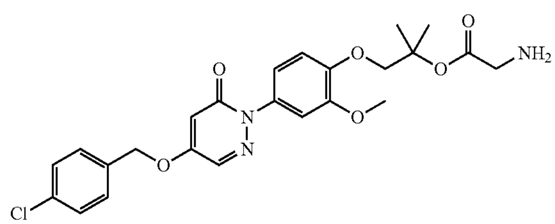 | 0.83; method 5 | 488 | $^1$H NMR (400 MHz, MeOD) δ ppm 7.80 (1 H, d, J = 2.76 Hz), 7.29-7.46 (4 H, m), 6.87-7.06 (3 H, m), 6.35 (1 H, d, J = 2.76 Hz), 5.10 (2 H, s), 4.18 (2 H, s), 3.76 (3 H, s), 3.61 (2 H, s), 1.55 (6 H, s) |
| P-5 | H-3 | 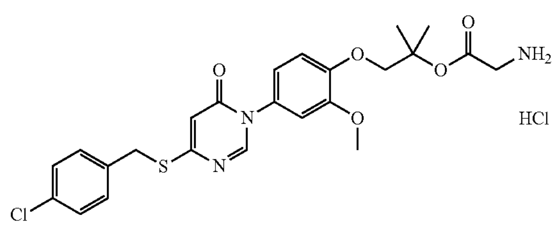 | 0.94 min method 5 | 435 | $^1$H NMR (400 MHz, CHLOROFORM-d) δ ppm 8.20 (1 H, d, J = 2.01 Hz), 7.73-7.87 (4 H, m), 7.17-7.26 (3 H, m), 7.02 (1 H, d, J = 8.28 Hz), 3.91 (3 H, s), 3.89 (2 H, s), 1.38 (6 H, s) |

Example P-1

1-(4-(4-(4-Chlorobenzylthio)-6-oxopyrimidin-1(6H)-yl)-2-methoxyphenoxy)-2-methylpropan-2-yl 2-aminoacetate hydrochloride

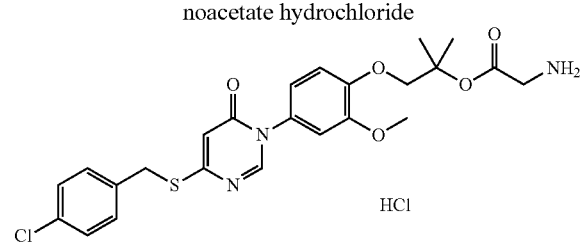

A. 1-(4-(4-(4-Chlorobenzylthio)-6-oxopyrimidin-1(6H)-yl)-2-methoxyphenoxy)-2-methylpropan-2-yl 2-(tert-butoxycarbonylamino)acetate To a stirred suspension of the alcohol H-2 (33 mg, 0.07 mmol), 4-pyrrolidinopyridine (11 mg, 0.07 mmol) and BOC-glycine (65 mg, 0.37 mmol) in CH$_2$Cl$_2$ (3.5 mL) was added N,N'-diisopropylcarbodiimide (0.06 mL, 0.37 mmol). The reaction was stirred at 45° C. for 3 hours. The reaction was allowed to cool to RT and hydrazine (0.04 mL, 1.3 mmol) was added and stirred for 30 min. The reaction mixture was diluted with methylene chloride, washed with water and sat. NaHCO$_3$, prior to drying over Na$_2$SO$_4$ and concentrating under vacuum. Chromatography (silica gel/hexanes/ethyl acetate 100:0 to 0:100 gradient) afforded the desired ester (35 mg, 0.06 mmol, 79% yield). LC MS (M+1=604; also observed M-BOC=504), $t_R$ 1.10 min (method 5).

B. 1-(4-(4-(4-Chlorobenzylthio)-6-oxopyrimidin-1(6H)-yl)-2-methoxyphenoxy)-2-methylpropan-2-yl 2-aminoacetate hydrochloride To a stirred solution of BOC glycinate ester described in Part A (30 mg, 0.05 mmol) in dioxane (0.2 mL) was treated with 1M HCl in diethyl ether (2.5 mL) at RT for 2 hours. The volatiles were removed under vacuum. The resulting solid was triturated with ether followed by trituration with methylene chloride to give the amine hydrochloride salt P-1 (21 mg, 0.04 mmol, 79% yield) as a white solid. LC MS (M+1=504), $t_R$ 0.85 min (method 5): $^1$H NMR (400 MHz, MeOD) δ 8.28 (1H, s), 7.45 (2H, d), 7.33 (2H, d), 7.05-7.12 (2H, m), 6.93 (1H, dd), 6.37 (1H, s), 4.37 (2H, s), 4.29 (2H, s), 3.86 (3H, s), 3.69 (2H, s), 1.64 (6H, s).

BIOLOGICAL ASSAYS

Radioligand Binding Assay for Assessment of MCHR1 Activity

Assay and Biological Evaluation

Compounds of Formula I were initially characterized in an in vitro binding assay to determine their Ki or ability to antagonize binding of a peptide agonist to the human melanin concentrating hormone receptor (MCHR1).

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl$_2$, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100. Filters were dried; 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

| Example No. | Ki (nM) |
|---|---|
| A1 | 41 |
| A13 | 1153 |
| A17 | 458 |
| B1 | 39 |
| C5 | 2199 |
| D2 | 37 |
| E1 | 1065 |
| H1 | 35 |
| H2 | 7 |
| H6 | 11 |
| G3 | 378 |
| J1 | 23 |

EVALUATION OF PRODRUGS

The relative ability of the prodrug to enhance exposure (bioavailability) was assessed in an eight hour PK study using cannulated SPRAGUE DAWLEY® (CD, Charles River Breeding Laboratory) rats. The compounds (parent and prodrug esters) were administered p.o. at 2.0 ml/kg as a suspension in 0.5% methyl cellulose, 0.1% Tween 80 in water at 10 mg/kg p.o. Blood samples were taken at 1, 2, 4 and 8 hr. After determination of parent concentration, an AUC was calculated for the eight hour study.

Assessment of in Vivo MCHR1 Activity

Male SPRAGUE DAWLEY® (CD, Charles River Breeding Laboratory) rats weighing approximately 240 grams were placed in individual plastic cages with ALPHADRI® bedding. The room was maintained at 72° F. and 50% humidity, and a 12/12 light dark cycle with lights out at 1600 hours. The rats were conditioned for 5 days prior to the start of the study to having a choice of foods. A normal chow (Harlan Teklad, 2018) that contains 18% protein, 5% fat and 73% carbohydrate and a high fat high sugar diet (Research Diets (D2327) that contains 20% protein, 40% fat and 40% carbohydrate where the carbohydrate is entirely sucrose and the fat is soybean and coconut oil. Studies have revealed that rats exhibit a high preference for the high fat/high sucrose diet (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

The assessment of activity of the compounds of Formula I of the invention in treating intestinal inflammation such as caused by inflammatory bowel disease, colitis and/or Crohn's disease, as described above, may be carried out employing the various assays as disclosed in Kokkotou, E. et al., "Melanin-concentrating hormone as a mediator of intestinal inflammation", *PNAS*, 105(30):10613-10618 (Jul. 29, 2008).

What is claimed is:

1. A compound having the following Formula I, or pharmaceutically acceptable salt thereof:

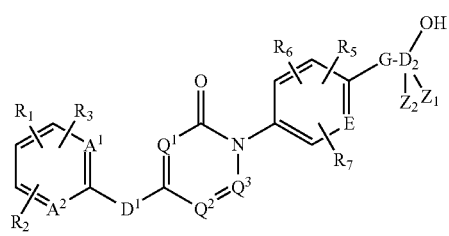

wherein,
$A^1$ and $A^2$ are independently C or N;
E is C or N;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, —$CR^8R^9X$—, —$XCR^8R^9$—, —$CHR^8CHR^9$—, —$CR^{10}$=$CR^{10'}$—, —C≡C—, or 1,2-cyclopropyl;

X is O, S or $NR^{11}$;

$R^1$, $R^2$, and $R^3$ are independently selected from the group consisting of hydrogen, halogen, substituted or unsubstituted $C_1$ to $C_4$ alkyl, substituted or unsubstituted $C_3$ to $C_5$ cycloalkyl, —$CF_3$, —$OCF_3$, —$OR^{12}$, substituted or unsubstituted phenyl, substituted or unsubstituted cycloalkoxy, and —$SR^{12}$; G is O, S or —$NR^{15}$;

$D^2$ is substituted or unsubstituted $C_2$ to $C_4$ alkyl, substituted or unsubstituted substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-substituted or unsubstituted $C_3$ to $C_5$ cycloalkoxy or when G is —$NR^{15}$, G and $D^2$ together may optionally form an azetidine, pyrrolidine or piperidine ring;

$Z_1$ and $Z_2$ are independently hydrogen, substituted or unsubstituted $C_1$ to $C_3$ alkyl, substituted or unsubstituted $C_3$ to $C_5$ cycloalkyl, —$OCH_3$, substituted or unsubstituted $C_3$ to $C_5$ cycloalkoxy, halo, —$CF_3$, —$OCONR^{14}R^{14'}$, —CN, —$CONR^{14}R^{14'}$, —$SOR^{12}$, —$SO_2R^{12}$, —$NR^{14}COR^{14'}$, —$NR^{14}CO_2R^{14'}$, —$CO_2R^{12}$, $NR^{14}SO_2R^{12}$ or —$COR^{12}$;

$R^5$, $R^6$, and $R^7$ are independently selected from the group consisting of hydrogen, halogen, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, —$CF_3$, —$SR^{12}$, —$OCH_3$, —$OCH_2CH_3$, —CN, —$CONR^{14}R^{14'}$, $SOR^{12}$, $SO_2R^{12}$, $NR^{14}COR^{14'}$, $NR^{14}CO_2R^{12}$. $CO_2R^{12}$, $NR^{14}SO_2R^{12}$ and —$COR^{12}$;

$R^8$, $R^9$, $R^{10}$, $R^{10'}$, $R^{11}$ are independently hydrogen or —$CH_3$;

$R^{12}$ is substituted or unsubstituted $C_1$ to $C_4$ alkyl or substituted or unsubstituted $C_3$ to $C_5$ cycloalkyl;

$R^{14}$ and $R^{14'}$ are independently H, substituted or unsubstituted $C_1$ to $C_3$ alkyl, substituted or unsubstituted $C_3$ to $C_5$ cycloalkyl or $R^{14}$ and $R^{14'}$ together with the N to which they are attached form a ring having 4 to 7 atoms; and $R^{15}$ is hydrogen or substituted or unsubstituted $C_1$ to $C_4$ alkyl.

2. The compound according to claim 1 wherein $R^1$, $R^2$, and $R^3$ are each independently H, halo, substituted or unsubstituted $C_3$ to $C_5$ cycloalkoxy, or —$CF_3$.

3. The compound according to claim 1 wherein G is O.

4. The compound according to claim 1 wherein $D^2$ is —$CH_2C$—.

5. The compound according to claim 1 wherein $Z_1$ and $Z_2$ are both —$CH_3$ or $Z_1$ is H and $Z_2$ is $C_3$ to $C_5$ cycloalkyl.

6. The compound according to claim 1 wherein $D^1$ is a bond, —$CR^8R^9X$—, —$XCR^8R^9$—, —$CR^{10}$=$CR^{10}$—, or —C≡C— and X is O, S, —$SO_2$ or —$NR^{11}$.

7. The compound according to claim 1 wherein $Z^1$ and $Z^2$ are —$CH_3$ or $Z^1$ is H and $Z^2$ is cyclopropyl.

8. The compound according to claim 1 having the following Formula Ia:

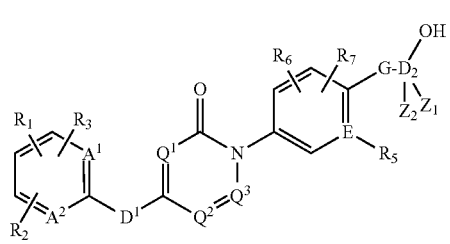

wherein $R_1$, $R_2$, and $R_3$ are independently H, halo, $C_1$ to $C_6$ alkyl, or $CF_3$;

$A^1$ is C or N;

$A^2$ is C;

$Q^1$, $Q^2$, and $Q^3$ are independently C or N provided that at least one of $Q^1$, $Q^2$, and $Q^3$ is N but not more than one of $Q^1$, $Q^2$, and $Q^3$ is N;

$D^1$ is a bond, —$CR^8R^9X$—, —$XCR^8R^9$—, 1,2 cylcopropyl, —$CR^{10}$=$CR^{10'}$— or —C≡C—;

X is O, S, —$NR^{11}$;

$R^8$, $R^9$, $R^{10}$, $R^{10'}$, and $R^{11}$ are each independently H or $C_1$ to $C_6$ alkyl;

$R^5$ is —$CH_3$ or —$OCH_3$, and $R^6$ and $R^7$ are H;

G is O or S;

$D^2$ is —$CH_2C$— or —$CH_2$-cyclobutyl;

$Z^1$ and $Z^2$ are both —$CH_3$, halo, or $Z^1$ is H and $Z^2$ is cyclopropyl.

9. The compound according to claim 8 wherein $Q^1$ is N and $Q^2$ and $Q^3$ are C.

10. The compound according to claim 8 wherein $Q^2$ is N and $Q^1$ and $Q^3$ are C.

11. The compound according to claim 8 wherein $Q^3$ is N and $Q^2$ and $Q^3$ are C.

12. The compound according to claim 8 wherein $D^1$ is —$CH_2X$— and X is O, S, or NH.

13. A compound selected from the group consisting of:

115
-continued
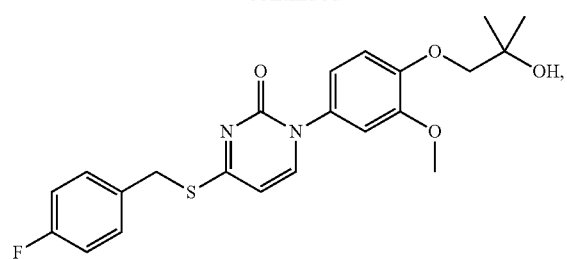
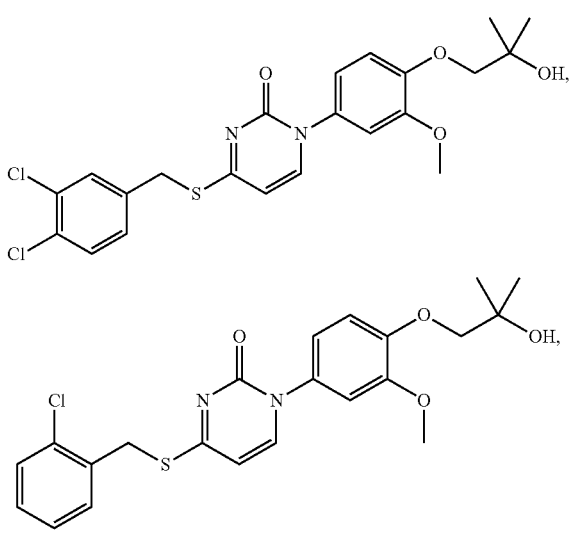
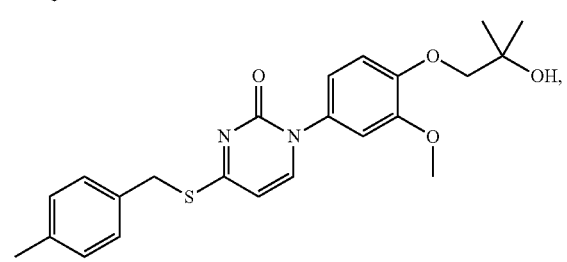
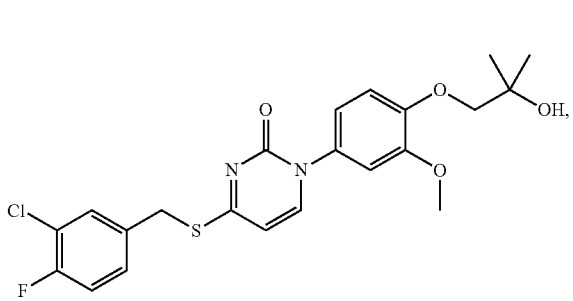
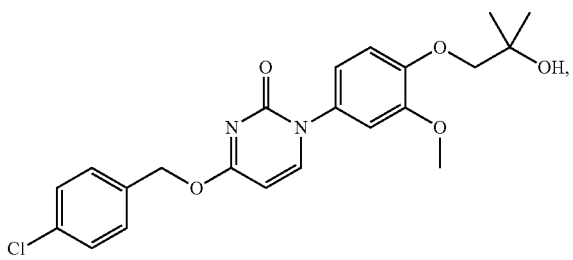
116
-continued
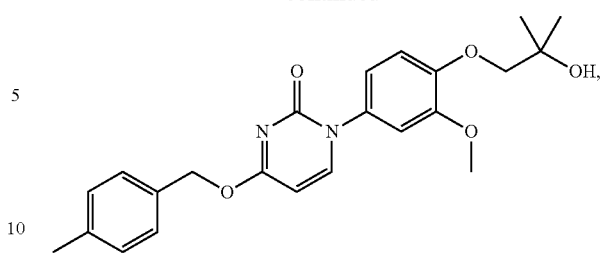
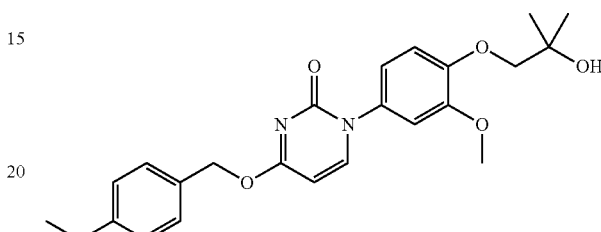
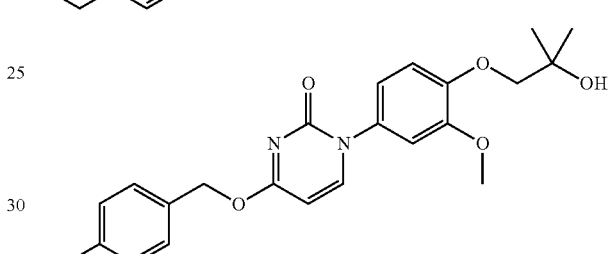
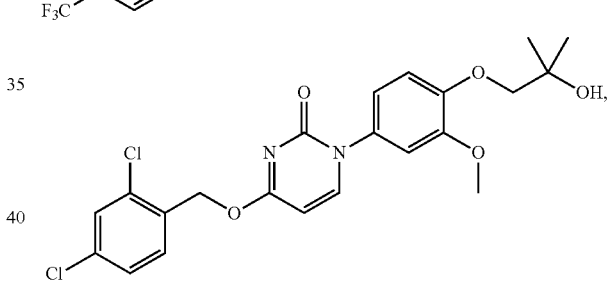
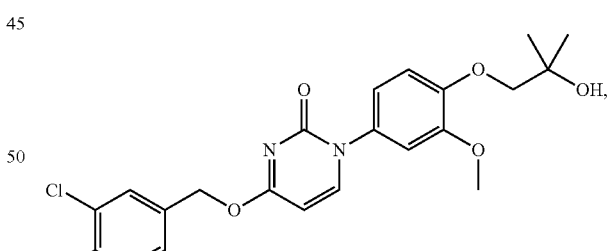
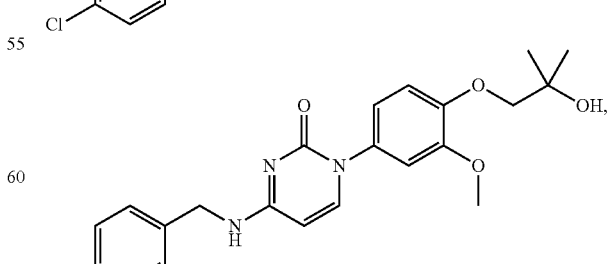

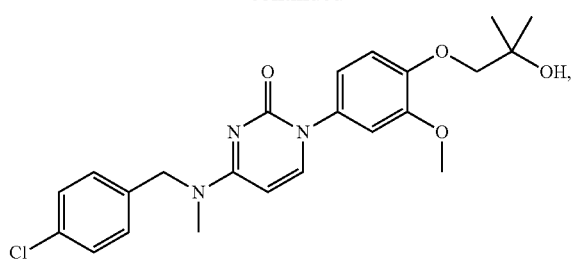
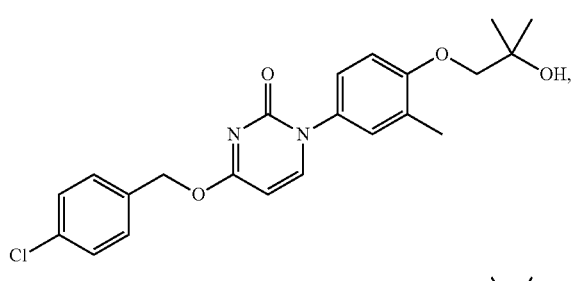
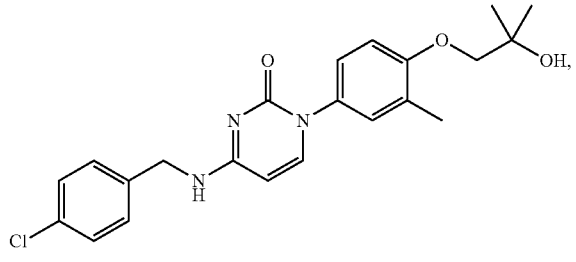
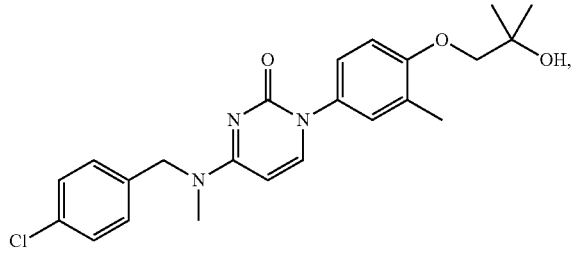
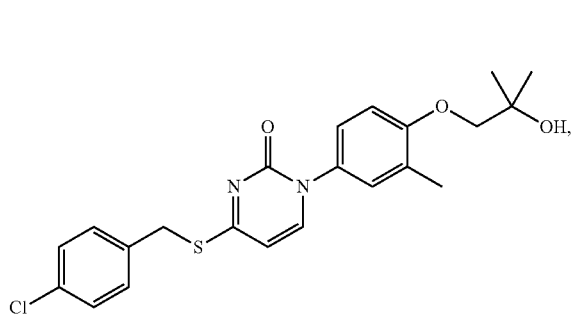
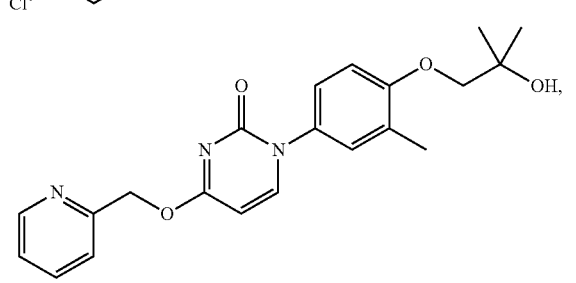
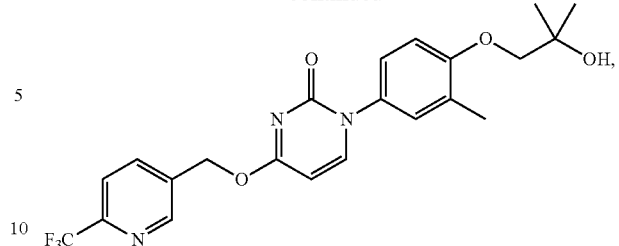
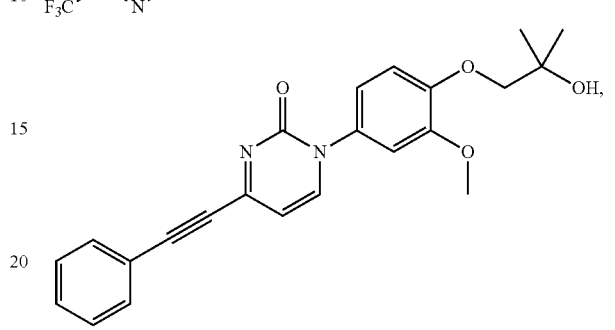
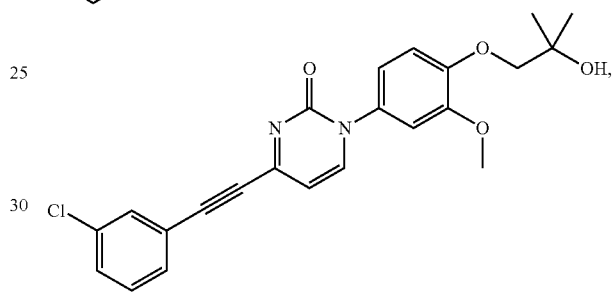
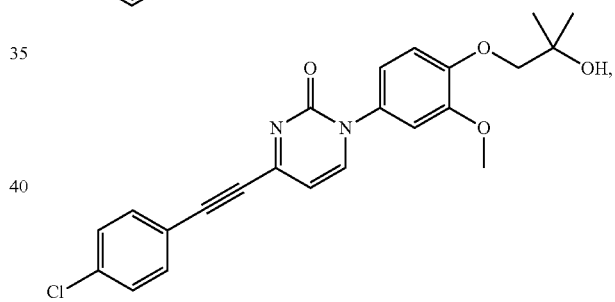
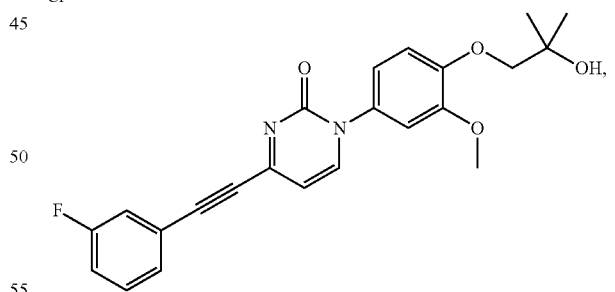
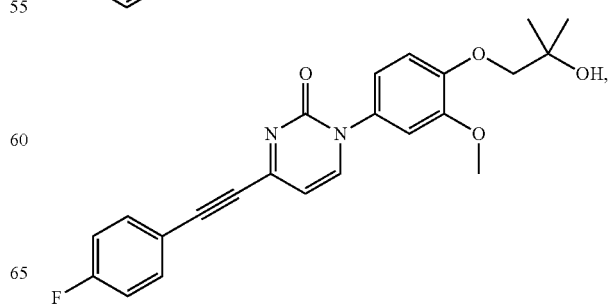

119
-continued
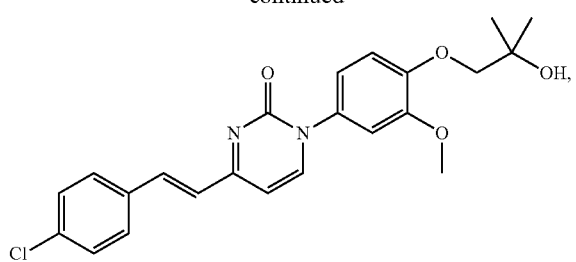
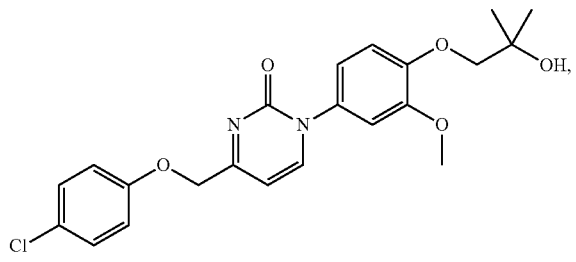
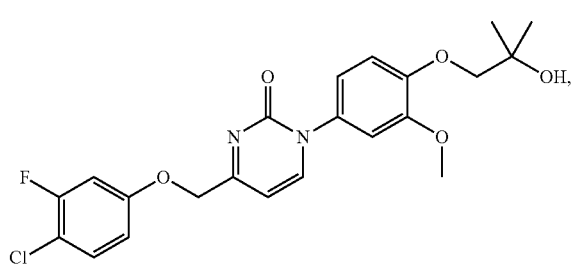
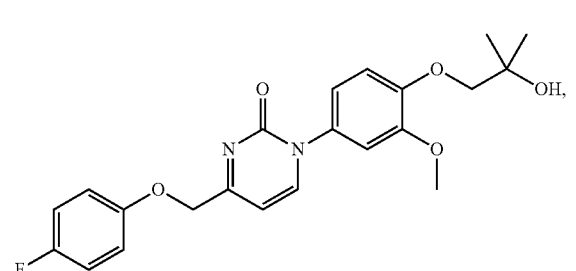
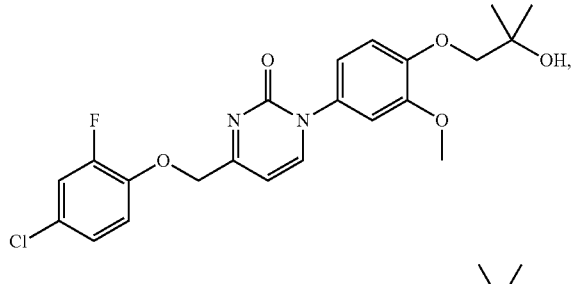
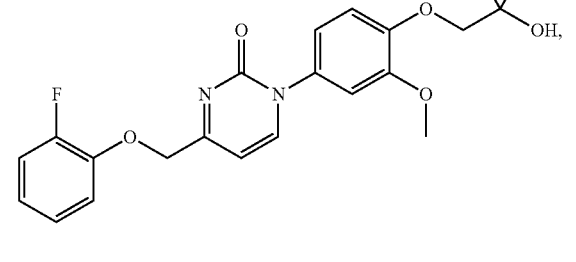
120
-continued
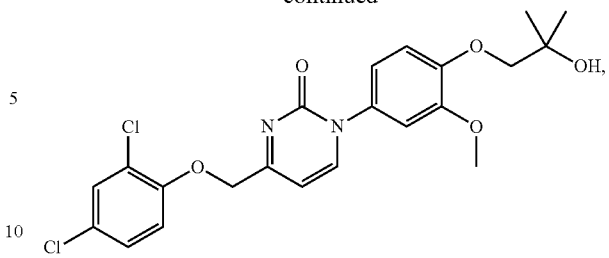
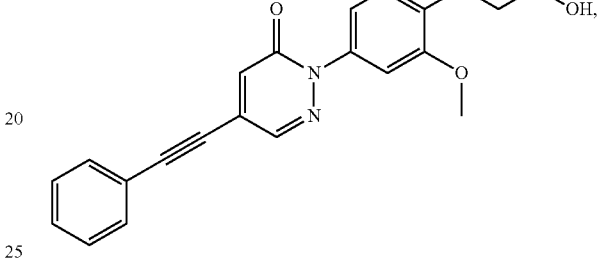
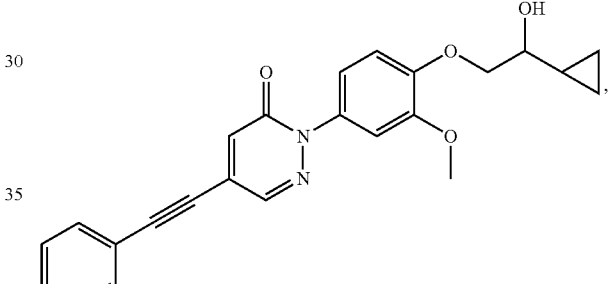
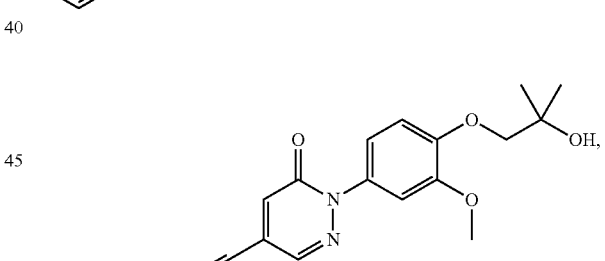
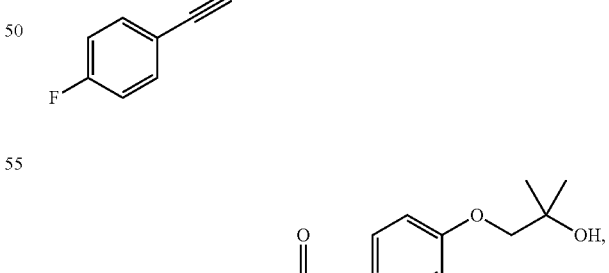
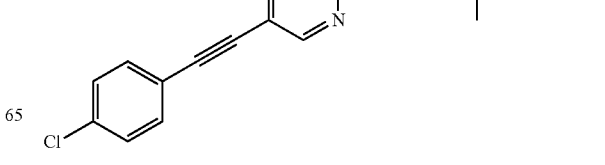

121
-continued
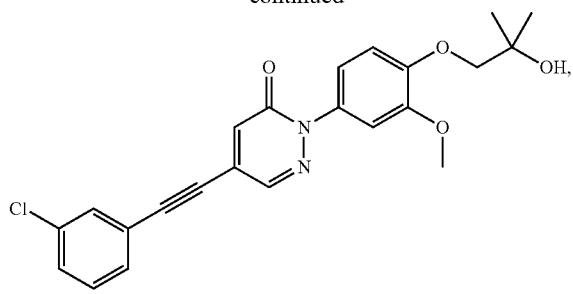
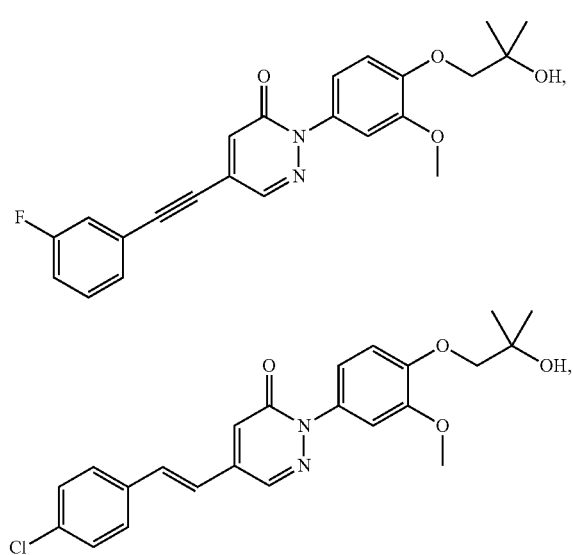
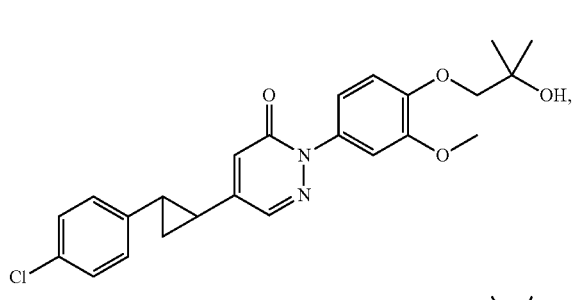
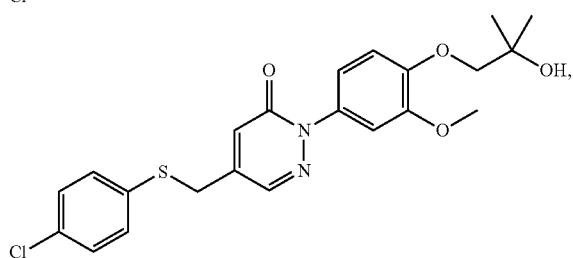
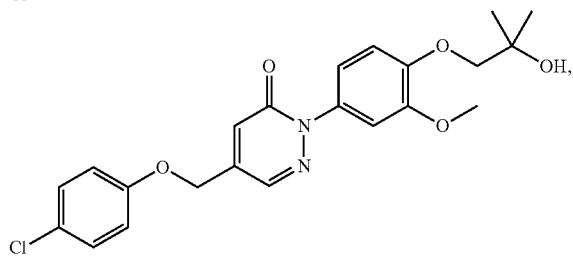
122
-continued
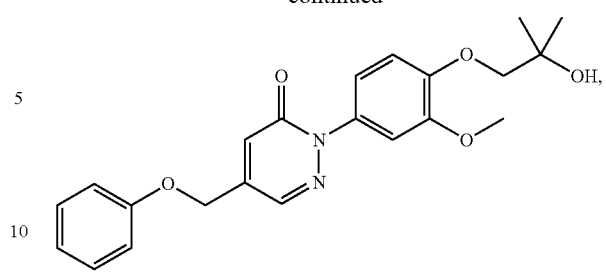
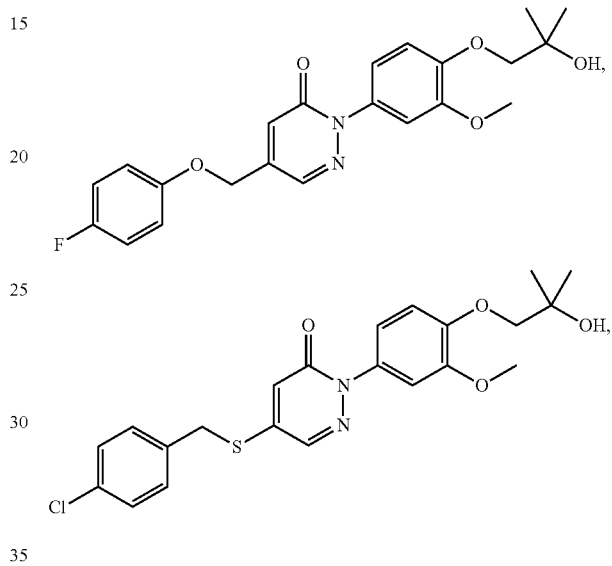
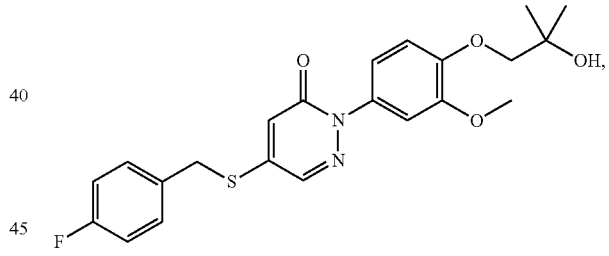
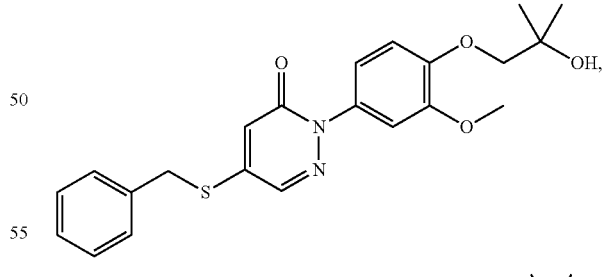
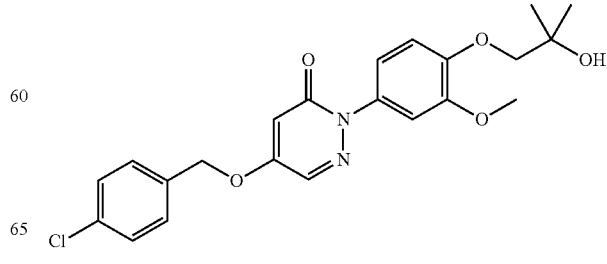

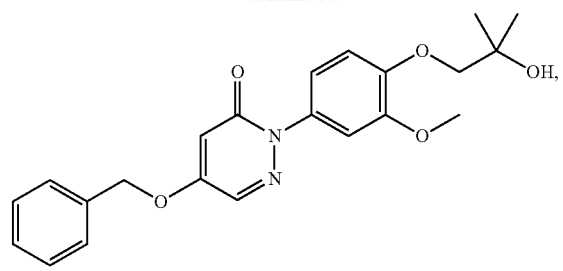
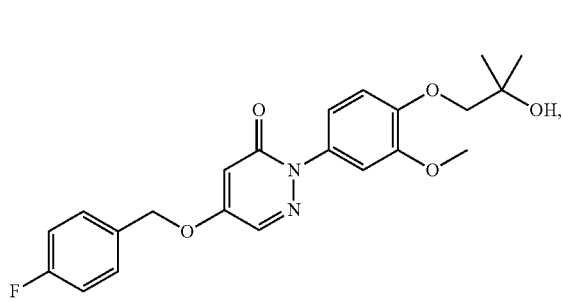
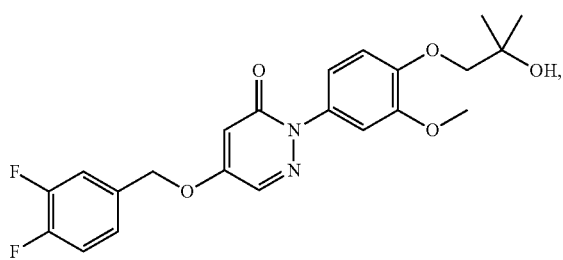
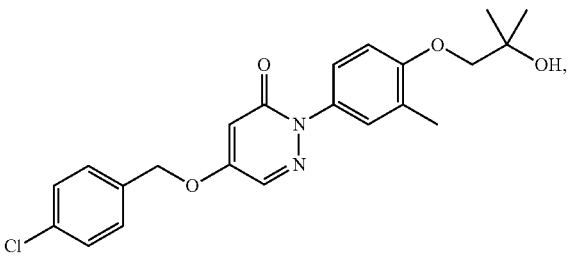
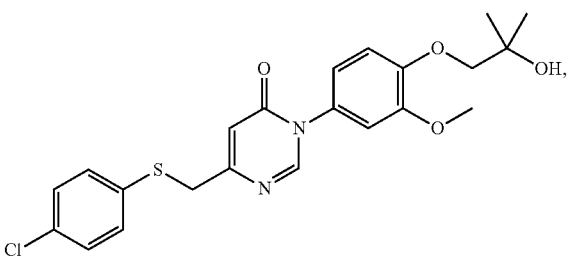
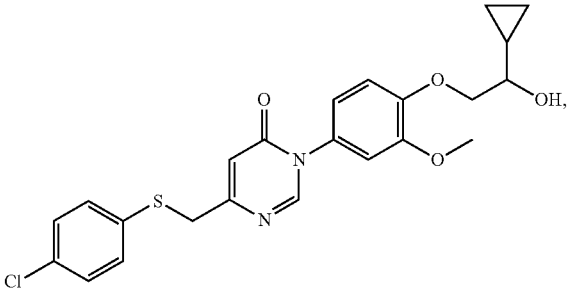
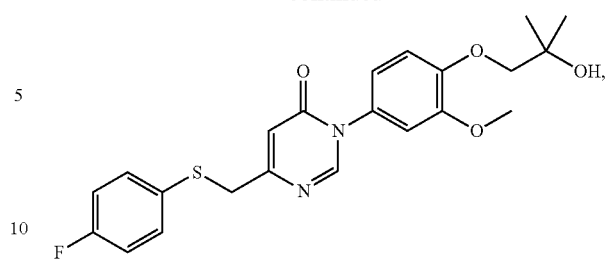
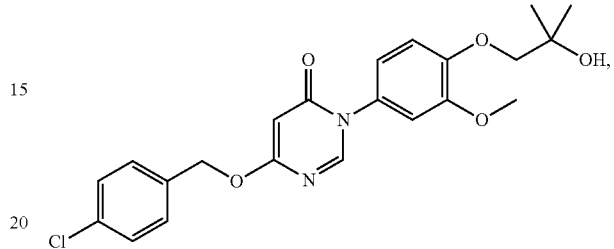
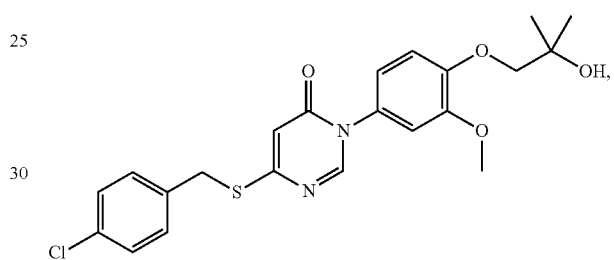
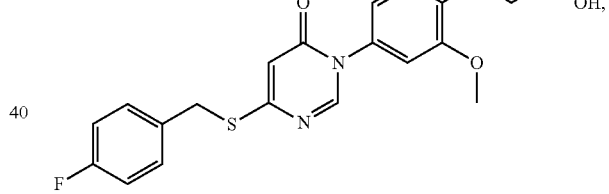
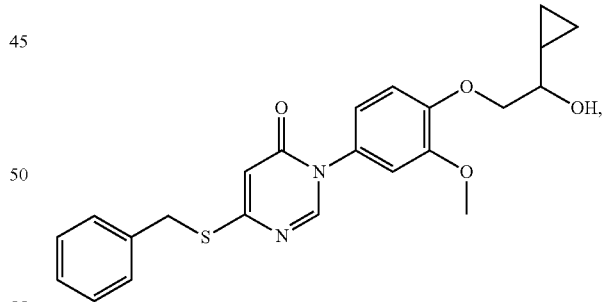
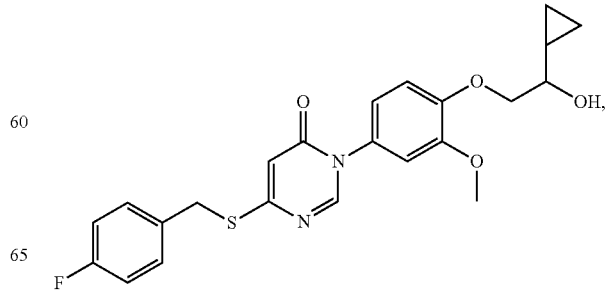

-continued

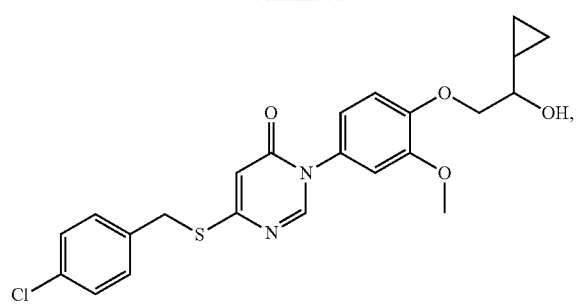
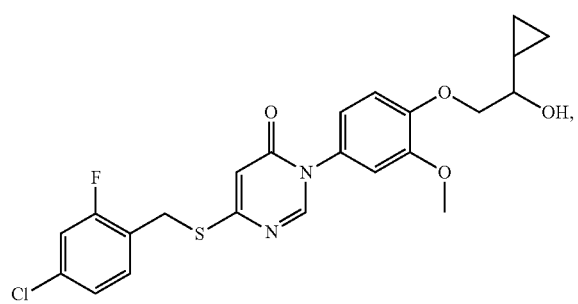
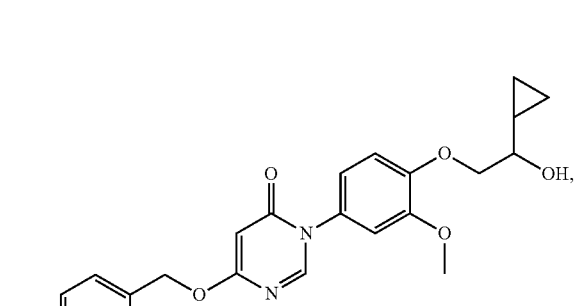
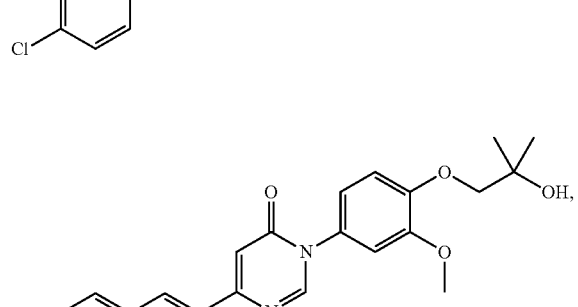
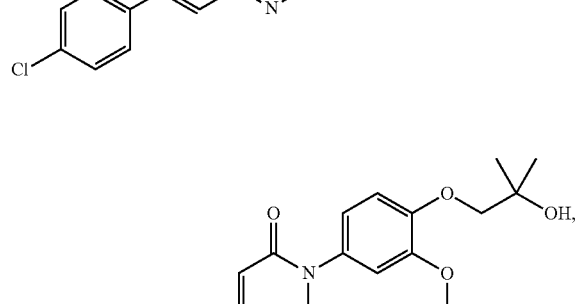

-continued

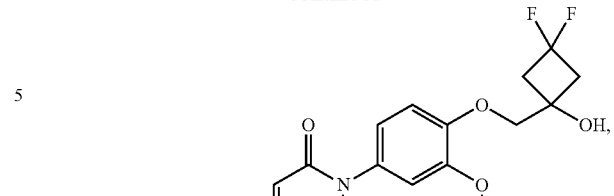
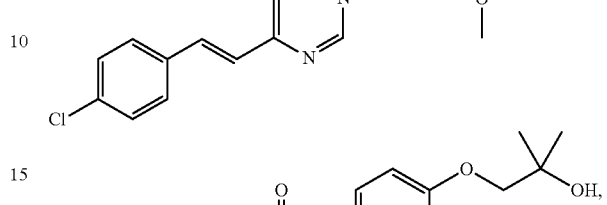
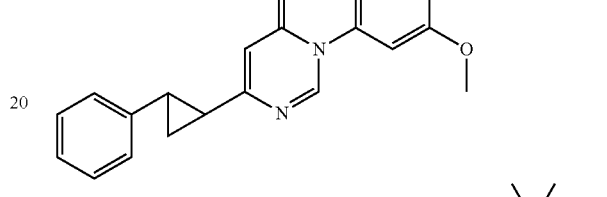
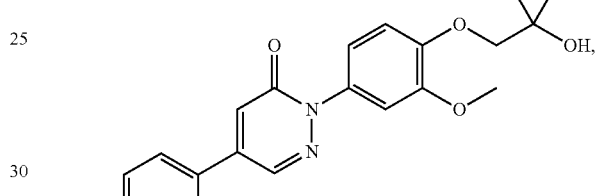
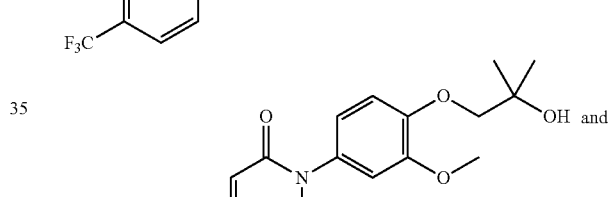

and

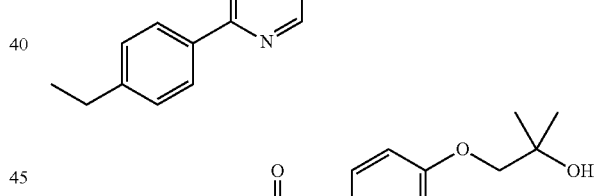
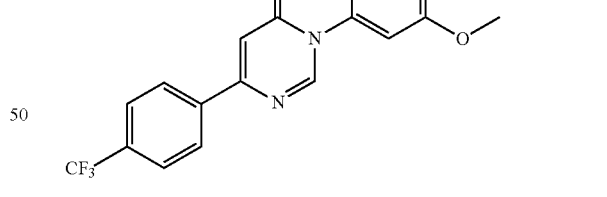

or a pharmaceutically acceptable salt of any of the preceding compounds.

14. A pharmaceutical composition comprising a compound according to claim 1 in an amount effective to treat obesity in a patient in need of such treatment together with a pharmaceutically acceptable carrier or diluent.

15. A pharmaceutical combination comprising a compound according to claim 1 and at least one additional therapeutic agent selected from the group consisting of an anti-obesity agent, an anti-diabetes agent, an anti-anxiety agent, an anti-inflammatory agent or an anti-depressant.

* * * * *

UNITED STATES PATENT AND TRADEMARK OFFICE
CERTIFICATE OF CORRECTION

PATENT NO. : 8,278,316 B2
APPLICATION NO. : 13/255170
DATED : October 2, 2012
INVENTOR(S) : Saleem Ahmad Page 1 of 1

It is certified that error appears in the above-identified patent and that said Letters Patent is hereby corrected as shown below:

Column 113
Line 39, "$NR^{14}CO_2R^{12}$" should read -- $NR^{14}CO_2R^{12}$, --.

Column 114
Line 23-24, "cylcopropyl," should read -- cyclopropyl, --.

Signed and Sealed this
Eighth Day of January, 2013

David J. Kappos
*Director of the United States Patent and Trademark Office*